US012788266B2

(12) United States Patent
Traverso et al.

(10) Patent No.: US 12,788,266 B2
(45) Date of Patent: Nov. 10, 2026

(54) SYSTEM AND METHOD FOR A FLEXIBLE PRESSURE SENSOR FOR GASTROINTESTINAL MANOMETRY

(71) Applicants: MASSACHUSETTS INSTITUTE OF TECHNOLOGY, Cambridge, MA (US); The Brigham and Women's Hospital, Inc., Boston, MA (US)

(72) Inventors: Giovanni Traverso, Cambridge, MA (US); Kewang Nan, Cambridge, MA (US)

(73) Assignees: MASSACHUSETTS INSTITUTE OF TECHNOLOGY, Cambridge, MA (US); The Brigham and Women's Hospital, Inc., Boston, MA (US)

( * ) Notice: Subject to any disclaimer, the term of this patent is extended or adjusted under 35 U.S.C. 154(b) by 281 days.

(21) Appl. No.: 18/730,223

(22) PCT Filed: Jan. 18, 2023

(86) PCT No.: PCT/US2023/011013
§ 371 (c)(1),
(2) Date: Jul. 18, 2024

(87) PCT Pub. No.: WO2023/141134
PCT Pub. Date: Jul. 27, 2023

(65) Prior Publication Data

US 2025/0114005 A1 Apr. 10, 2025

Related U.S. Application Data

(60) Provisional application No. 63/301,491, filed on Jan. 20, 2022.

(51) Int. Cl.
*A61B 5/03* (2006.01)
*A61B 1/273* (2006.01)
(Continued)

(52) U.S. Cl.
CPC ............ *A61B 5/037* (2013.01); *A61B 5/6852* (2013.01); *G01L 1/20* (2013.01); *A61B 2562/0247* (2013.01); *A61M 2025/0001* (2013.01)

(58) Field of Classification Search
CPC .................. A61B 5/037; A61B 5/6852; A61B 2562/0247; A61B 5/0215; A61B 1/273;
(Continued)

(56) References Cited

U.S. PATENT DOCUMENTS 5,609,060 A 3/1997 Dent
8,441,530 B2 5/2013 Radeva et al.
(Continued)

OTHER PUBLICATIONS

Aas, IH Monrad. "Organizational decentralization in radiology." Journal of telemedicine and telecare 12.1_suppl (2006): 1-3.
(Continued)

*Primary Examiner* — Justin Xu
(74) *Attorney, Agent, or Firm* — Quarles & Brady, LLP

(57) ABSTRACT

A system for assessing a pressure profile of a gastrointestinal (GI) tract is provided. The system includes a flexible tube defining a first lumen and an electrically-conductive liquid contained within the first lumen. At least one restriction is restriction formed on the flexible tube to constrict but not completely occlude the first lumen. The system further includes a sensor system configured to monitor an electrical property of the electrically-conductive fluid over time and to generate a report of pressure changes in the GI tract by correlating changes in the electrical property with the pressure changes in the GI tract.

19 Claims, 56 Drawing Sheets

(51) Int. Cl.
*A61B 5/00* (2006.01)
*A61B 5/0215* (2006.01)
*A61B 5/0538* (2021.01)
*A61M 25/00* (2006.01)
*G01L 1/20* (2006.01)

(58) Field of Classification Search
CPC .......... A61B 5/0538; A61B 5/03; G01L 1/20; A61M 2025/0001
See application file for complete search history.

(56) References Cited

U.S. PATENT DOCUMENTS

| | | | |
|---|---|---|---|
| 9,814,408 B2 | 11/2017 | Mabary et al. |
| 2009/0082698 A1 | 3/2009 | Kassab |
| 2015/0297110 A1 | 10/2015 | Kassab |
| 2018/0008156 A1 | 1/2018 | Pandolfino et al. |
| 2018/0029290 A1 | 2/2018 | Bottiglio et al. |
| 2021/0322769 A1 | 10/2021 | Kim |

OTHER PUBLICATIONS

Al-Alusi, Mostafa A., et al. "Wearing your heart on your sleeve: The future of cardiac rhythm monitoring." Current cardiology reports 21.12 (2019): 1-11.

Anderson, P., et al. "Survey of digestive health across Europe: Final report. Part 2: The economic impact and burden of digestive disorders." United European gastroenterology journal 2.6 (2014): 544-546.

Araromi, Oluwaseun A., et al. "Ultra-sensitive and resilient compliant strain gauges for soft machines." Nature 587.7833 (2020): 219-224.

Arkwright, J. W., et al. "In-vivo demonstration of a high resolution optical fiber manometry catheter for diagnosis of gastrointestinal motility disorders." Optics express 17.6 (2009): 4500-4508.

Arkwright, John W., et al. "Design of a high-sensor count fibre optic manometry catheter for in-vivo colonic diagnostics." Optics Express 17.25 (2009): 22423-22431.

Ascher, Marcia. "The logical-numerical system of Inca quipus." Annals of the History of Computing 5.3 (1983): 268-278.

Attari, Ali, et al. "Comparison of anorectal function measured using wearable digital manometry and a high resolution manometry system." Plos one 15.9 (2020): e0228761.

Bellinger, Andrew M., et al. "Oral, ultra-long-lasting drug delivery: application toward malaria elimination goals." Science Translational Medicine 8.365 (2016): 365ra157-365ra157.

Bredenoord, Albert J., et al. "Chicago classification criteria of esophageal motility disorders defined in high resolution esophageal pressure topography 1." Neurogastroenterology & Motility 24 (2012): 57-65.

Cheeney, G., et al. "Topographic and manometric characterization of the recto anal inhibitory reflex." Neurogastroenterology & Motility 24.3 (2012): e147-e154.

Chen, Lie, et al. "Icing performance of superhydrophobic silicone rubber surfaces by laser texturing." Materials Research Express 6.12 (2020): 1250e2.

Cooper, Christopher B., et al. "Stretchable capacitive sensors of torsion, strain, and touch using double helix liquid metal fibers." Advanced Functional Materials 27.20 (2017): 1605630.

Corsetti, Maura, et al. "Pan-colonic pressurizations associated with relaxation of the anal sphincter in health and disease: a new colonic motor pattern identified using high-resolution manometry." American Journal of Gastroenterology 112.3 (2017): 479-489.

De Leon, Alex, Sven-Egron Thorn, and Magnus Wattwil. "High-resolution solid-state manometry of the upper and lower esophageal sphincters during anesthesia induction: a comparison between obese and non-obese patients." Anesthesia & Analgesia 111.1 (2010): 149-153.

De Schepper, H. U., et al. "Impact of spatial resolution on results of esophageal high-resolution manometry." Neurogastroenterology & Motility 26.7 (2014): 922-928.

Dickey, Michael D., et al. "Eutectic gallium-indium (EGaIn): a liquid metal alloy for the formation of stable structures in microchannels at room temperature." Advanced functional materials 18.7 (2008): 1097-1104.

Dinning, P. G., et al. "Low-resolution colonic manometry leads to a gross misinterpretation of the frequency and polarity of propagating sequences: initial results from fiber-optic high-resolution manometry studies." Neurogastroenterology & Motility 25.10 (2013): e640-e649.

Dinning, P. G., et al. "Quantification of in vivo colonic motor patterns in healthy humans before and after a meal revealed by high-resolution fiber-optic manometry." Neurogastroenterology & Motility 26.10 (2014): 1443-1457.

Florisson, J. M. G., et al. "A novel model used to compare water-perfused and solid-state anorectal manometry." Techniques in Coloproctology 10.1 (2006):17-20.

Fox, Mark R., et al. "Clinical measurement of gastrointestinal motility and function: who, when and which test ?." Nature Reviews Gastroenterology & Hepatology 15.9 (2018): 568-579.

Gao, Yuji, et al. "Wearable microfluidic diaphragm pressure sensor for health and tactile touch monitoring." Advanced Materials 29.39 (2017): 1701985.

Gourcerol, G., et al. "Do endoflip assessments of anal sphincter distensibility provide more information on patients with fecal incontinence than high-resolution anal manometry ?." Neurogastroenterology & Motility 28.3 (2016): 399-409.

Han, Mengdi, et al. "Catheter-integrated soft multilayer electronic arrays for multiplexed sensing and actuation during cardiac surgery." Nature Biomedical Engineering 4.10 (2020): 997-1009.

Hansen, M. B. "Small intestinal manometry." Physiological Research 51.6 (2002): 541-556.

Holloway, Richard H. "Esophageal manometry." GI Motility online (2006).

Hosotsubo et al., Fabrication of artificial food bolus for evaluation of swallowing, Public Library of Science ONE (Dec. 15, 2016), doi:10.1371/journal.pone.0168378.

International Search Report and Written Opinion for corresponding PCT Application No. PCT/US2023/011013, mailed May 1, 2023.

Isakadze, Nino, and Seth S. Martin. "How useful is the smartwatch ECG ?." Trends in cardiovascular medicine 30.7 (2020): 442-448.

Kessing, Boudewijn F, et al. "Water-perfused esophageal high-resolution manometry: normal values and validation." American Journal of Physiology-Gastrointestinal and Liver Physiology 306.6 (2014): G491-G495.

Kim, Kyuyoung, et al. "Highly Sensitive and Wearable Liquid Metal-Based Pressure Sensor for Health Monitoring Applications: Integration of a 3D-Printed Microbump Array with the Microchannel." Advanced Healthcare Materials 8.22 (2019): 1900978.

Koppen, I. J. N., et al. "Motility of the left colon in children and adolescents with functional constipation; a retrospective comparison between solid-state and waterperfused colonic manometry." Neurogastroenterology & Motility 30.9 (2018): e13401.

Leber, Andreas, et al. "Soft and stretchable liquid metal transmission lines as distributed probes of multimodal deformations." Nature Electronics 3.6 (2020): 316-326.

Lee, Tae Hee, and Adil E. Bharucha. "How to perform and interpret a high resolution anorectal manometry test." Journal of neurogastroenterology and motility 22.1 (2016): 46.

Liem, O., et al. "Solid-state vs water-perfused catheters to measure colonic high amplitude propagating contractions." Neurogastroenterology & Motility 24.4 (2012): 345-e167.

Lu, Yue, et al. "Transformable liquid-metal nanomedicine." Nature communications 6.1 (2015): 1-10.

Luo, Yiyue, et al. "Learning human-environment interactions using conformal tactile textiles." Nature Electronics 4.3 (2021): 193-201.

Ma, Zhijun, et al. "Permeable superelastic liquid-metal fibre mat enables biocompatible and monolithic stretchable electronics." Nature Materials (2021): 1-10.

(56) References Cited

OTHER PUBLICATIONS

Miller, Larry, et al. "Use of endoluminal ultrasound to evaluate gastrointestinal motility." Digestive Diseases 24.3-4 (2006): 319-341.

Paterson, William G. "Esophageal peristalsis." GI Motility online (2006).

Peery, Anne F., et al. "Burden and cost of gastrointestinal, liver, and pancreatic diseases in the United States: update 2018." Gastroenterology 156.1 (2019): 254-272.

Pfeifer, Johann, and Lucia Oliveira. "Anorectal manometry and the rectoanal inhibitory reflex." Constipation. Springer, London, 2006. 71-83.

Quipu, Smithsonian snapshot, Smithsonian Institute, Nov. 8, 2011, https://.si.edu/newsdesk/snapshot/quipu.

Rasijeff, Annika MP, et al. "High-resolution anorectal manometry: A comparison of solid-state and water-perfused catheters." Neurogastroenterology & Motility 29.11 (2017): e13124.

Roriz, Paulo, et al. "Review of fiber-optic pressure sensors for biomedical and biomechanical applications." Journal of Biomedical Optics 18.5 (2013):050903.

Sadowski, Daniel C., and Linda Broenink. "High-resolution esophageal manometry: a time motion study." Canadian Journal of Gastroenterology 22.4 (2008): 365-368.

Shaker, Anisa, et al. "Multiple rapid swallow responses during esophageal high resolution manometry reflect esophageal body peristaltic reserve." The American journal of gastroenterology 108.11 (2013): 1706.

Sundaram, Subramanian, et al. "Learning the signatures of the human grasp using a scalable tactile glove." Nature 569.7758 (2019): 698-702.

Wang, Kun, et al. "A comparative study of 22-channel water-perfusion system and solid-state system with 36-sensors in esophageal manometery." BMC Gastroenterology 12.1 (2012): 157.

Xi, Wang, et al. "Soft tubular microfluidics for 2D and 3D applications." Proceedings of the National Academy of Sciences 114.40 (2017): 10590-10595.

Yeo, Joo Chuan, et al. "Wearable tactile sensor based on flexible microfluidics." Lab on a Chip 16.17 (2016): 3244-3250.

Yi, Liting, and Jing Liu. "Liquid metal biomaterials: a newly emerging area to tackle modern biomedical challenges." International Materials Reviews 62.7 (2017): 415-440.

Yu, Xinge, et al. "Skin-integrated wireless haptic interfaces for virtual and augmented reality." Nature 575.7783 (2019): 473-479.

Zifan, Ali, et al. "Endoflip vs high-definition manometry in the assessment of fecal incontinence: A data—driven unsupervised comparison." Neurogastroenterology & Motility 30.12 (2018): e13462.

SYSTEM AND METHOD FOR A FLEXIBLE PRESSURE SENSOR FOR GASTROINTESTINAL MANOMETRY

CROSS REFERENCE TO RELATED APPLICATIONS

This application represents the U.S. national stage entry of International Application No. PCT/US2023/011013 filed Jan. 18, 2023, which is based on, claims priority to, and incorporates hereby reference in its entirety for all purposes, U.S. Provisional Application Ser. No. 63/301,491, filed Jan. 20, 2022, and entitled, "SYSTEM AND METHOD FOR A FLEXIBLE PRESSURE SENSOR FOR GASTROINTESTINAL MANOMETRY."

STATEMENT REGARDING FEDERALLY SPONSORED RESEARCH

N/A

BACKGROUND

The present disclosure relates generally to pressure sensors and pressure sensing systems for use in gastrointestinal (GI) manometry, and more specifically, for the diagnosis and monitoring of GI motility disorders. GI dysmotility can affect any part of the alimentary tract and may manifest in or contribute to digestive conditions including gastroesophageal reflux disease, gastroparesis, intestinal pseudo-obstruction, irritable bowel syndrome, chronic constipation, and fecal incontinence. Not only do these symptoms rank among the most common patient presentations, they are also associated with significant morbidity, including malnutrition, feeding tube dependency, need for invasive surgery, frequent hospitalizations, and death.

The current evaluation of patients with these symptoms involves multiple diagnostic elements. In particular, the evaluation of tone and contractile patterns of the GI tract is an essential aspect in the diagnosis of GI motility disorders, with manometry playing one of the most important roles. Manometry involves placing a manometer, which is a catheter-like device containing a series of pressure transducers located in the catheter, endoluminally into the GI tract of a patient to measure real-time pressure changes along the length of the device. The pressure changes that are measured result from the peristaltic contractions of the patient's GI tract and can be used to identify regions with impaired motility and other types of GI motility disorders.

Several forms of manometers for GI manometry have been developed to evaluate the specific segments of the alimentary tract, including esophageal, antroduodenal, colonic, and anorectal manometry. Generally, such clinically-applied manometry techniques have relied on water-perfused (WP) catheters or solid-state (SS) transducers as the pressure-sensing elements. More recently, high-resolution manometry (HRM), which consists of a higher number of pressure transducers or sensors spaced closer together, has emerged in the last decade and considerably enhanced the identification of abnormal findings. Likewise, advances in both hardware and software technology further allow the standardization of clinical interpretation of manometry results using known methods, which has facilitated and expanded the clinical utility of GI manometry.

Nonetheless, current systems for GI manometry suffer from a number of drawbacks. In particular, current systems suffer from high cost, complexity, and bulkiness that limit their use in less developed regions or non-hospital settings, which can limit a physician's ability to assess and diagnose GI dysmotility conditions in resource-constrained settings. In addition, although most manometry catheters can be re-used up to approximately five hundred times, the complexity and cost associated with disassembling and disinfecting place burdens to even the most resource-rich regions or hospitals, leading to not only increased risk for cross-contamination, but also reduced case throughput. Furthermore, the complexity and size of the system, in particular with HRM, which can include, for example, twenty-one to thirty-six pressure sensors and can require up to three wires per pressure sensor, limits the maximum length of the device and, thus, the length of the GI tract that can be evaluated at any one time.

In view of the above, a need exists for an improved GI manometry system. In particular, it would desirable to provide a GI manometry system that can provide for high-resolution and high density pressure measurements, while also being simple and cheap to manufacture from easily accessible and economical materials. Additionally, it would be desirable to provide a GI manometer system that can either be easily disinfected or disposable, and that can measure pressure along a substantial or entire length of a patient's GI tract. The discussion above is merely provided for general background information and is not intended to unduly limit the scope of the claimed subject matter.

SUMMARY

The present disclosure meets the aforementioned needs by providing systems and methods for GI manometry. Aspects of the present disclosure, as generally disclosed herein, can provide for an economical and easy to manufacture GI manometry or other monitoring system that provides pressure measurements of a GI tract of a patient. Such a system can include a sensor configured as a pressure-sensing catheter formed from a sealed flexible tube that is filled with an electrically conductive liquid. A number of restrictions can be formed along the length of the tube. The restriction can act, for example, as piezo-resistive pressure elements, whereby contractions of a GI tract deform the tube at the restriction to cause a measurable change in electrical properties of the conductive fluid. This change in electrical properties can be monitored or measured and correlated with a pressure exerted by the GI tract on the catheter. In some cases, multiple tubes may be used together to form a single catheter or catheter system and the restrictions formed along each of the tubes can be placed relative to one another. A sensor and/or processor can spatially resolve the location of a pressure measurement.

In accordance with one aspect of the present disclosure, a system for assessing a pressure profile of a gastrointestinal (GI) tract is provided. The system can include a flexible tube defining a first lumen and an electrically-conductive liquid contained within the first lumen. At least one restriction can be restriction formed on the flexible tube to constrict but not completely occlude the first lumen. The system can further include a sensor system that can be configured to monitor an electrical property of the electrically-conductive fluid over time and to generate a report of pressure changes in the GI tract by correlating changes in the electrical property with the pressure changes in the GI tract.

In accordance with another aspect of the present disclosure, a manometry system for obtaining a pressure profile of a gastrointestinal (GI) tract is provided. The manometry system can include a catheter configured to be placed endoluminally into the GI tract, a sensor, and a processor. The catheter can include a plurality of sealed flexible tubes. Each of the plurality of sealed flexible tubes can define a (first) lumen that can be filled with an electrically-conductive fluid. Additionally, each sealed flexible tube can define at least one restriction to constrict but not completely occlude the lumen. The restriction can be compressed by the GI tract to induce a change in an electrical resistance of the electrically-conductive fluid within a respective one of the plurality of sealed flexible tubes. The sensor can be configured to acquire electrical measurements of each of the plurality of sealed flexible tubes. The processor can be configured to determine a pressure profile of the GI tract by correlating the electrical measurements of each of the plurality of sealed flexible tubes with a pressure in the GI tract.

In accordance with another aspect of the present disclosure, a method of manufacturing a system for obtaining a pressure profile of a gastrointestinal (GI) tract is provided. The method can include the steps of inserting a first conductor into a first end of a flexible tube defining a first lumen so that the first conductor extends between the first lumen and an exterior of the flexible tube, and sealing the first end of the flexible tube. Additionally, the method can include the steps of filling the flexible tube with a conductive fluid, inserting a second conductor into a second end of the flexible tube to extend the second conductor between the first lumen and the exterior of the flexible tube, and sealing the second end of the flexible tube. Furthermore, the method can include the step of forming at least one restriction on the flexible tube. The at least one restriction can be configured to constrict but not completely occlude the first lumen, and to be compressed by the GI tract to induce a change in an electrical resistance of the conductive fluid within the flexible tube that is correlated with a pressure at the at least one restriction.

According to yet another aspect of the present disclosure, a flexible pressure sensor is provided. The flexible pressure sensor can include a sealed flexible tube, a conductive liquid, first and second conductors, and a restriction. The sealed flexible tube can define a (first) lumen extending between a first end of the sealed flexible tube and a second end of the sealed flexible tube, and the conductive liquid can be contained within the lumen. The first conductor can extend into the lumen at the first end of the sealed flexible tube and the second conductor can extend into the lumen at the second end of the sealed flexible tube. The restriction can be formed on the sealed flexible tube between the first end and the second end to constrict but not completely occlude the lumen. The restriction can be configured to be compressed to induce a change in an electrical resistance of the conductive liquid within the sealed flexible tube that is correlated with a pressure at the restriction.

This Summary and the Abstract are provided to introduce a selection of concepts in a simplified form that are further described below in the Detailed Description. This Summary is not intended to identify key features or essential features of the claimed subject matter, nor are they intended to be used as an aid in determining the scope of the claimed subject matter

BRIEF DESCRIPTION OF THE DRAWINGS

The following drawings are provided to help illustrate various features of non-limiting examples of the disclosure and are not intended to limit the scope of the disclosure or to exclude alternative implementations.

DETAILED DESCRIPTION

Figure 1:
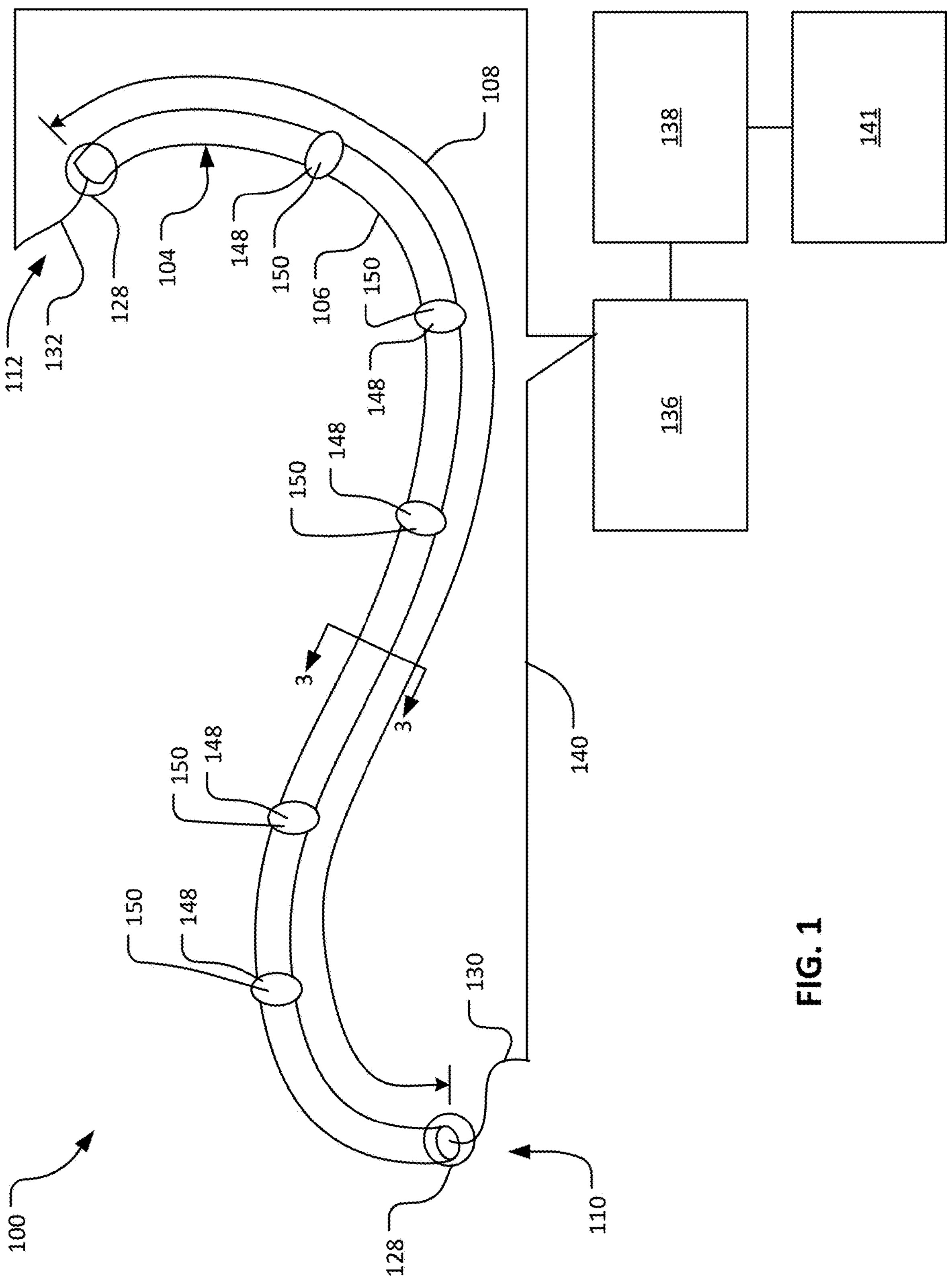
FIG. 1 is a perspective view of an exemplary catheter system according to aspects of the present disclosure.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The term "about," as used herein, refers to variations in the numerical quantity that may occur, for example, through typical measuring and manufacturing procedures. Throughout the disclosure, the terms "about" and "approximately" refer to a range of values ±5% of the numeric value that the term precedes.

The following discussion is presented to enable a person skilled in the art to make and use embodiments of the invention. Various modifications to the illustrated embodiments will be readily apparent to those skilled in the art, and the generic principles herein can be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the invention. Skilled artisans will recognize the examples provided herein have many useful alternatives and fall within the scope of embodiments of the invention.

As mentioned above, pressure sensors and transducers can be incorporated into a pressure sensing catheter, (i.e., a GI manometer) that can be used to obtain a pressure profile of a GI tract, or a portion thereof. For example, a manometer can be inserted into endoluminally into an esophageal tract of a patient to measure contractions at various positions along the esophageal tract to produce a pressure profile. The pressure profile can be used by a physician to observe and diagnose GI motility disorders.

Conventional high-resolution manometers generally use anywhere between 21 and 36 solid state pressure transducers that can be inserted into a GI tract of a patient to measure a pressure profile of the GI tract. Each of these pressure transducers typically measure pressure using a Wheatstone bridge, which requires a multiplicity of electrical connections to each individual transducer. Because of the large number of transducers and associated electrical connections, conventional high-resolution manometers are complex and sensitive diagnostic tools that are expensive, difficult to manufacture, and difficult to disinfect. Additionally, because of the large number of electrical connections, conventional high-resolution manometers are generally limited to lengths ranging between 15 centimeters and 80 centimeters, as greater lengths become too bulky to be used in many patients. Accordingly, while conventional systems can provide high resolution and high accuracy pressure profiles, they can only obtain a pressure profile for a limited portion of a gastrointestinal tract at any one time.

Aspects of the present disclosure can provide for improvements over conventional high resolution manometer systems, including providing a manometer that is both economical and easy to manufacture (e.g., the individual components of the manometer are low in cost, easy to obtain, and easy to assemble). Additionally, aspects of the disclosure provide for a highly customizable manometer system with performance characteristics that are similar to conventional high-resolution manometry system, while also allowing for increased lengths that permit pressure profiles to be obtained for comparatively large portions of a GI tract, and in some cases an entirety (e.g., an entire length) of a GI tract. More specifically, aspects of the invention utilize basic knotting configuration and other types of restrictions to transform otherwise insensitive silicone/eGaIn composites into devices that can detect pressure changes, in particular small pressure changes within a GI tract, which can allow for the use of low-cost, accessible materials and fabrication schemes, while avoiding comparatively complex materials or architectures that require lengthy preparation or expensive equipment, thereby providing a cost-effective, and in some cases, disposable, alternative to conventional manometry systems. Additionally, aspects of the disclosure relate to multiplexing strategies for minimizing the number of channels (e.g., electrical connections) without the need for complex and expensive multiplexer circuits.

A manometry system according to aspects of the present disclosure can provide a system that is configured to be inserted into a GI tract to obtain a pressure profile of the GI tract. A system can generally include at least one flexible tube (e.g., a tube made from silicone, silicone-based rubber, latex, polyvinyl chloride, polyurethane, fluoropolymers, thermoplastic elastomers, other types of elastomeric materials, and other materials that can be used to contain fluids, including biocompatible and non-biocompatible materials) that defines a lumen running along the length of the tube. In some cases, a flexible tube can preferably be an electrically-insulative and liquid-tight elastomeric tube, which is biocompatible and has low mechanical hysteresis and a low elastic modulus, and which is inert with respect to liquid metals (e.g., polydimethylsiloxane (PDMS), styrene-ethylene-butylene-styrene (SEBS), fluoroelastomer, and polyurethane rubber). A size (e.g., a cross-sectional area) of the tube can be selected based on a desired pressure range to be measured (e.g., a typical pressure range associated with a GI tract, such as between 0 mmHg and 250 mmHg). The tube can be a round or other shaped tube defining an inner diameter (a diameter of the lumen), an outer diameter, and a wall thickness therebetween. Accordingly, in one non-limiting example, configured to be inserted into a GI tract to measure pressures ranging between 0 mmHG and approximately 250 mmHG, a tube can be a silicone tube with an external diameter of approximately 0.64 millimeters and a wall thickness of approximately 0.17 millimeters.

A conductive fluid (e.g., an electrically conductive liquid) with high electrical conductivity (e.g., conductivities greater than or equal to approximately $3.3\times10^{6}$ S/m), and low viscosity (e.g., viscosities less than or equal to approximately $2\times10^{-3}$ pascal-seconds, Pa·s and toxicity can be contained within the lumen. In particular, the lumen can contain liquid eutectic gallium-indium (eGaIn). Relatedly, the tube can define a first end and a second end, both of which can be sealed so that the tube is a sealed tube and the lumen is an enclosed lumen. In some cases, a conductor (e.g., an electrical lead) can extend into each end of the tube to provide external electrical connections, which are electrically connected with one another by the conductive fluid contained in the lumen.

At least one restriction can be formed on the flexible tube. The restriction can be configured to constrict the lumen (e.g., to reduce a local cross-sectional area of the lumen), but not to completely occlude the lumen or, if occluded, otherwise facilitate electrical continuity through the occlusion. That is, in one configuration, even with the restriction in place, an electrical path is maintained between the conductors. In some cases, a clip or bracket can be coupled to the tube to produce the restriction. In other cases, a restriction can be formed by tying a knot in the flexible tube, for example, an overhand knot or another type of knot. The knot can be tightened to a predetermined tension. That is, a predetermined tensile force can be applied to form the knot. In one non-limiting example, approximately 0.1 Newtons can be applied to the tube on opposing sides of the knot to constrict the lumen. Additionally or alternatively, the knot or other means of restriction can be formed to a desired cross-sectional area of the lumen. In some cases, the tensile force can be applied for a predetermined amount of time, for example, 30 seconds. The knots can be tied by hand, or by a machine, which may allow for greater consistency and, therefore, reduce the overall error in any obtained pressure measurement. Additionally, in some cases, a sleeve can be formed or placed on a knot to prevent the knot from loosening and tightening during use, which may further reduce any error in an obtained pressure measurement. For example, an adhesive (e.g., a flexible, UV-curing adhesive) can be placed onto the knot.

Due to the flexible nature of the tube, the tube, and thus the restriction, can be compressed by the contractions (e.g., peristaltic contractions) of the GI tract, or another external force, which can cause a change in a cross-sectional area (e.g., a change in shape and/or reduction in area) of the lumen at the restriction. This change in the cross-sectional area results in a change (e.g. an increase or decrease) in an electrical property of the conductive material within the tube. The electrical property may be resistance (or conductance), however, other electrical properties, or inductance or capacitance may be used. In one non-limiting example, a sensor, such as a multimeter or multi-channel measurement device, can be coupled (e.g., electrically coupled) to the tube to measure an electrical property along the tube (e.g., an electrical resistance of the conductive fluid). The electrical property can be interpreted and correlated with a pressure exerted by the GI tract by the sensor or another a processor, which can then be used to determine a pressure profile of the GI tract.

In that regard, to obtain a high-resolution pressure profile, a plurality of tubes can be used together. In some configurations, the plurality of tubes can form a single catheter (e.g., a single manometer) that is inserted into a GI tract. In some cases, the plurality of catheters can be contained within a main sleeve, which can help to maintain the spatial relationship of each tube (e.g., the one or more restrictions of each tube) relative to one another. Accordingly, the at least one restriction of each tube can be arranged along the respective tube to spatially resolve compression by the GI tract, and relative to the at least one restriction of each of the other catheters. That is the restriction(s) of each of the catheters can be configured to be spatially displaced from each other when in the GI tract and multiplexed to spatially resolve compression by the GI tract. Put another way, the restrictions can be multiplexed to spatially resolve compression by the GI tract. Accordingly, the processor in communication with the sensor can be configured to use and resolve (e.g., by decoupling linear combinations of signals) the electrical measurements to identify the point at which the contraction of the GI tract is occurring along the length of the manometer.

FIG. 1 depicts a non-limiting example of a system 100 (e.g., a manometer) for obtaining a pressure or pressure profile of a GI tract according to aspects of the disclosure. The system 100 is configured as a pressure sensing catheter system having a pressure sensing catheter that can be inserted (e.g., placed endoluminally) into a GI tract to measure one or more pressures within (e.g., produced by) the GI tract, which correspond with a pressure profile of the GI tract. In that regard, the system 100 can be used by a physician to obtain a pressure profile along any portion of a GI tract in order to observe and diagnose GI motility disorders. Thus, the system 100 may have a length that corresponds with the portion of the GI tract to be observed and measured. For example, a length of the system 100 can be configured to correspond with a length of an esophageal tract, colon, or other portion of a GI track and any combinations thereof, including the GI tract in its entirety. In some cases, the length of the system 100 can be selected to allow for folding of the system 100.

A catheter system can include one or more pressure sensing catheters that are configured to measure a pressure or pressure profile. As illustrated, the system 100 includes a catheter 104 that can be placed within a GI tract; although other catheter systems may include more than one catheter. As discussed in greater detail below, the catheter 104 can be a piezo-resistive catheter that is configured to be compressed by the GI tract to produce a change in one or more electrical properties of the catheter 104. This change in electrical properties can be used to determine the pressure acting on the catheter 104. For example, when the catheter 104 is inserted into a GI tract, the peristaltic contractions of the GI tract compress the catheter 104, creating a change in electrical properties, such as resistance (e.g., via a piezo-resistive effect), which can be correlated with a pressure produced by the GI tract. More specifically, as will also be discussed in greater detail below, the catheter 104 can include one or more restrictions and the change in electrical resistance can be correlated with the pressure acting on the one or more restrictions.

A catheter is generally formed from one or more flexible tubes. In the illustrated non-limiting example, the catheter 104 includes a flexible tube 106. That is, the catheter 104 is formed from a tube made of a flexible material. For example, the tube 106 can be a silicone tube, or tube formed from another type of elastomeric material, in particular, a medical-grade elastomeric material. The tube 106 is configured as a round (e.g., generally circular) tube, although tubes with differently shaped cross sectional profiles are possible (e.g., ellipsoidal, square, rectangular, etc.) Additionally, the tube 106 defines a length 108 taken along the tube 106 between a first end 110 and a second end 112.

A tube can be configured as a hollow tube that defines one or more lumens that extend along a length of the tube. For example, a lumen may be a central lumen having a shape that generally corresponds with an external profile (e.g., shape) of the tube, or a lumen may have a shape that is different from the tube. With additional reference to FIGS. 2 and 3, in the illustrated non-limiting example, the tube 106 includes a lumen 116 (e.g., a central lumen) extending between the first end 110 and the second end 112. The lumen 116 has a rounded (e.g., generally circular) cross section that corresponds with the external profile fo the tube 106. Accordingly, the tube 106 defines an inner diameter 118 (e.g., a diameter of the lumen 116) and outer diameter 120 of the tube 106, and a wall thickness 122 therebetween (see FIG. 3). The size and material of the tube 106 can be selected to provide an approximately linear relationship between a desired range of pressures to be measured and a change in electrical property of the catheter 104.

A tube of a catheter system, and more specifically, a lumen defined within the tube, can contain (e.g., encapsulate) an electrically conductive fluid. In the illustrated non-limiting example, the tube 106 contains an electrically conductive fluid 124 within the lumen 116. It is preferable that the electrically conductive fluid 124 be a material that is in a liquid state at or above room temperature (e.g., with a melting point at or below approximately 20 degrees Celsius and atmospheric pressure), has low viscosity (approximately $1.99\times10^{-3}$ pascal-seconds, Pa·s), and has high electrical conductivity (approximately $3.4\times10^{6}$ S/m). Additionally, it is preferable, particularly where a catheter system is being placed endoluminally into a GI tract, that the conductive fluid 124 have low cytotoxicity, even though the conductive fluid 124 is enclosed within the lumen 116. Moreover, it is also preferable that the conductive fluid 124 have good moldability. That is, the ability to conform to cavities and enclosures of various geometries, for example, thin tubes having a lumen with a small cross-sectional area. For example, in preferred embodiment, the electrically conductive fluid 124 can be eGaIn. However, in other non-limiting examples, other types of conductive fluids may also be used, for example, Mercury, Cesium, and Gallium.

Accordingly, to ensure that an electrically conductive fluid remains secured within a lumen, a tube can be configured as a sealed tube. For example, both ends of the tube can be sealed shut. For example, with continued reference to FIG. 1, each of the first end 110 and the second end 112 are sealed so as to prevent the conductive fluid 124 from leaking or otherwise flowing out of the tube 106. Thus, the conductive fluid 124 is completely enclosed and retained within the lumen 116, which can help to reduce leakage of the conductive fluid 124 into, for example, a GI tract. The ends 110, 112 of the tube 106 can be sealed in a number of ways. For example, the ends 110, 112 can be sealed with an adhesive 128, such as a UV-curing adhesive. In other non-limiting examples, other known methods of sealing the ends 110, 112 may also be used. In some cases, the method of sealing the ends 110, 112 may be dependent, at least in part, on the material of the tube 106 and the specific use case scenario of the catheter 104.

To measure a pressure acting on a tube of a catheter, an electrical property (e.g., a change in an electrical resistance) of a conductive fluid contained within the tube can be measured. This electrical property can be correlated with the pressure acting on the tube (e.g., via a linear correlation). However, since a tube can be sealed at both ends in order to contain the conductive fluid, conductors (e.g., electrical leads) can be provided, which extend into the tube (e.g., into a lumen of the tube at the sealed ends). Thus, the conductors are in electrical connection with a conductive fluid contained in a lumen of the tube and extend outside of the tube to provide external electrical connections, which allow a property of the conductive fluid to be measured, for example, by a sensor.

As illustrated in FIG. 1, the catheter 104 includes first and second conductors 130, 132 (e.g., a copper wire or other know type of electrical lead) that extend into the lumen 116 at each of the first end 110 and the second end 112, respectively to be in electrical connection with the conductive fluid 124. More specifically, each of the first and second conductors 130, 132 extends from the lumen 116 and through the cured adhesive 128 at each of the ends 110, 112 to provide an external electrical connection (e.g., a wire or other electrical connector), which can be configured to couple to a sensor or other measurement device 136 (e.g., a multimeter or a multi-channel measurement device). In some cases, the measurement device 136 can be in communication with a processor device 138 that can be configured to analyze the changes in an electrical property measured by the measurement device 136, and correlate them with a pressure acting on the catheter 104. An interface 141 may be included for communicating information or reports from the system 100. In some configurations, the interface 141 may include a display and/or user interface to provide reports or display information regarding the pressure acting on the catheter and/or additional or alternative information that maybe needed by the clinician. For example, a screen may display reports, or a printer may generate reports. A user interface may be provided to interact with the system 100. Additionally or alternatively, the interface 141 may include communications interface, in addition to or instead of a user interface. The communications interface may communicate reports, data, or other information to a network or external device, such as a phone, tablet, or other device.

Relatedly, where multiple tubes are provided, each tube may be connected with the measurement device 136 via a separate channel (e.g., an input channel), or multiple tubes may share a single channel). Here, since the catheter 104 includes a single tube, the catheter 104 is coupled at each of the ends 110, 112 with the measurement device 136 via a single corresponding channel 140.

Accordingly, when an electrical property of the conductive fluid 124 is measured, the electrical property may be measured along the entire length of the tube 106. In other non-limiting examples, additional conductors may be provided, which may extend through other portions (e.g., a sidewall) of the tube 106, and which may allow for properties to be measured along only a portion of the catheter 104 (e.g., a portion of the conductive fluid 124). Where multiple conductors are provided, various combinations of conductors may be coupled to common (e.g., shared) channels of a measurement device.

Figure 2:
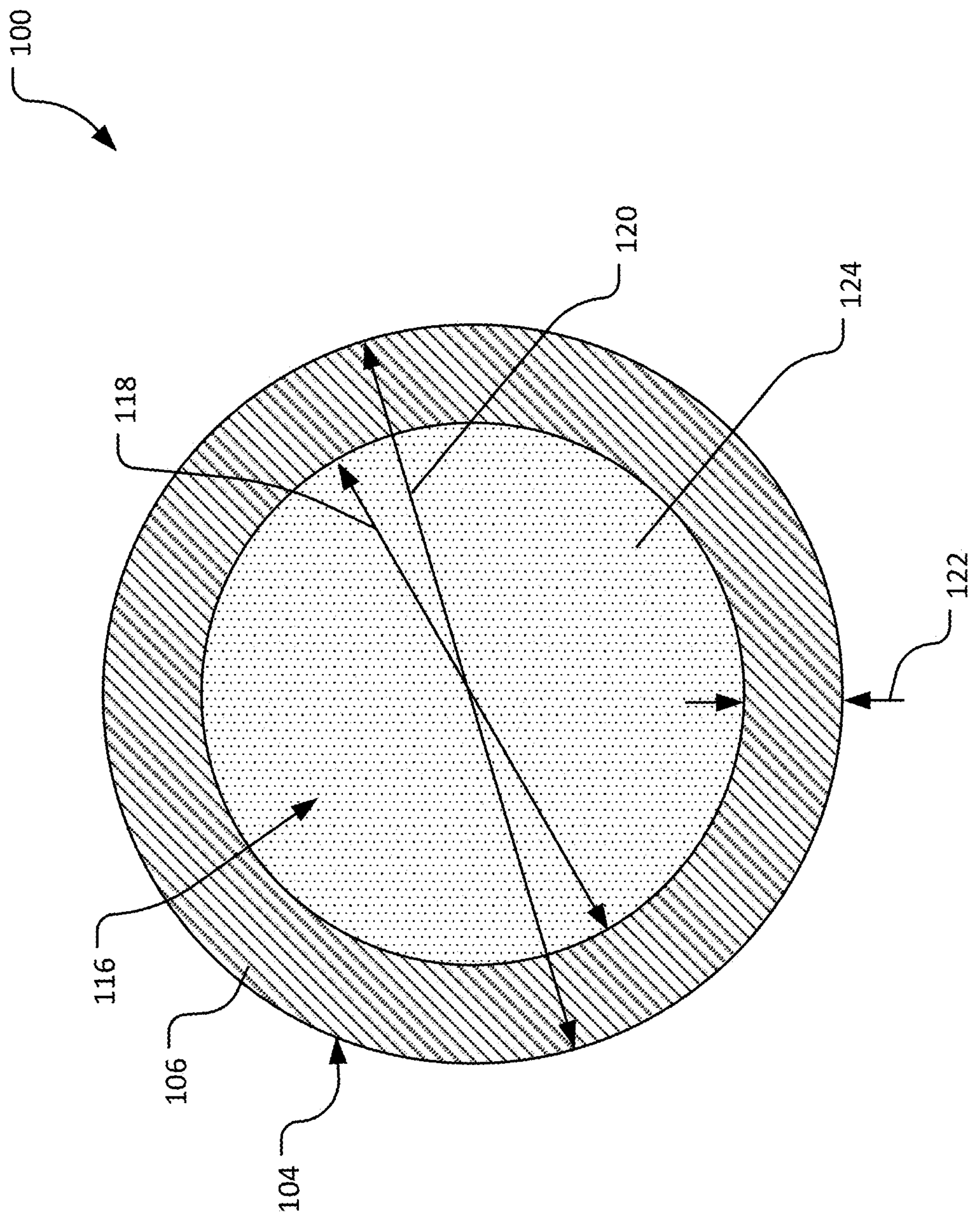
FIG. 2 is a cross-sectional view of a tube of the catheter system of FIG. 1 in an uncompressed configuration, taken along line 3-3.
Figure 3:
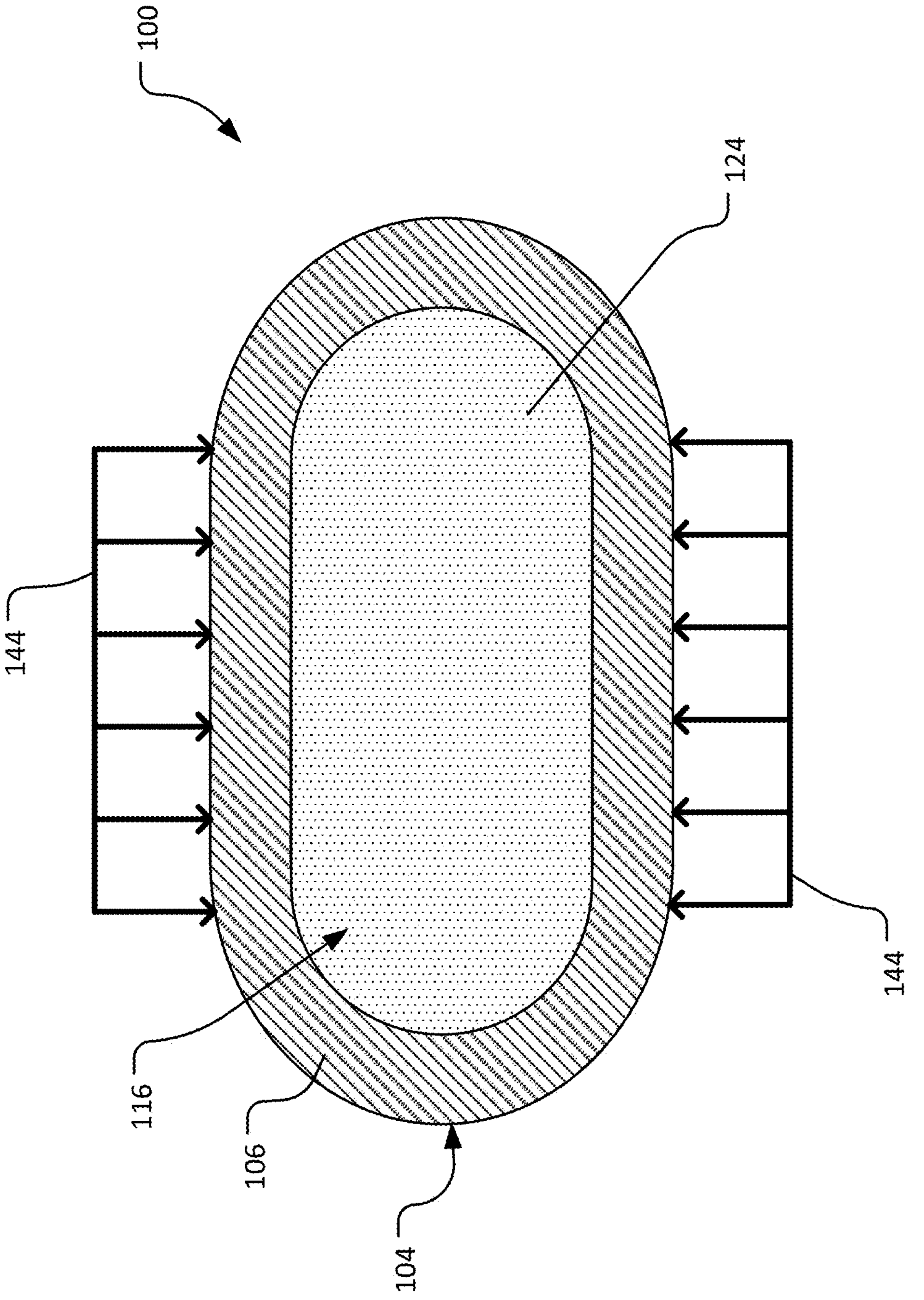
FIG. 3 is a cross-sectional view of the tube of FIG. 2 in a compressed configuration wherein an external pressure is applied to the tube.

In that regard, an electrical property of the conductive fluid 124 can change in response to an external pressure (e.g., force) acting on a tube of a catheter. More specifically, as illustrated in FIGS. 2 and 3, due to the flexible nature of the tube 106, an external force or pressure 144 (e.g., a contraction of a GI tract) can cause a change in a (local) cross-sectional area of the lumen 116. Correspondingly, a (local) cross-sectional area of the conductive fluid 124 contained in the lumen 116 also changes. For example, a local cross-sectional area of the conductive fluid 124 may undergo cross-sectional narrowing, which can change the shape of and reduce the local cross-sectional area of the conductive fluid 124. This change in cross-sectional area, and in particular, the reduction in cross-sectional area, can cause the electrical property of the conductive fluid 124 to increase. The change in electrical property of the conductive fluid 124 can then be correlated with the pressure 144 acting on the tube 106 (e.g., to obtain a pressure profile of a GI tract).

Accordingly, a tube of a catheter can be selected in accordance with a desired pressure range to be measured. That is, for example, the tube 106 must undergo sufficient cross-sectional narrowing in response to the applied pressure 144 to cause a change in electrical property that can be correlated with the applied pressure 144. Thus, where a tube has a comparatively large internal cross-sectional area, the application of a relatively small pressure to the tube may be insufficient to cause a measurable change in electrical property of the conductive fluid, or the change in electrical property may not correlate well with the applied pressure, such that the correlation may be non-linear. However, where a comparatively large pressure is applied, the measured change in property may have a linear correlation with the applied pressure. Correspondingly, a tube with a comparatively small internal diameter may be used to measure smaller pressures.

However, in some cases, in particular where small pressures are concerned, such as the pressures exerted by a GI tract, an internal area of a tube may need to be reduced even further. In such cases, one or more restrictions can be formed on (e.g., formed with) the tube. Such restrictions constrict a tube to reduce a cross-sectional area of the lumen without completely occluding the lumen so that electrical continuity of the conductive fluid is maintained along the entire length of the tube. In that regard, the restrictions effectively preload the tube so that the application of relatively minute pressures results in sufficient cross-sectional narrowing. In particular, a restriction can be configured so that pressures within a desired pressure range exhibit an approximately linear correlation with the associated change in electrical property of the catheter. In the illustrated example, the catheter 104 includes a plurality of restrictions 148 formed on the tube 106. In other non-limiting examples, the number of restrictions formed on a tube can be different. For example, only one restriction may be formed on a tube, or more than one restriction may be formed on a tube.

Figure 4:
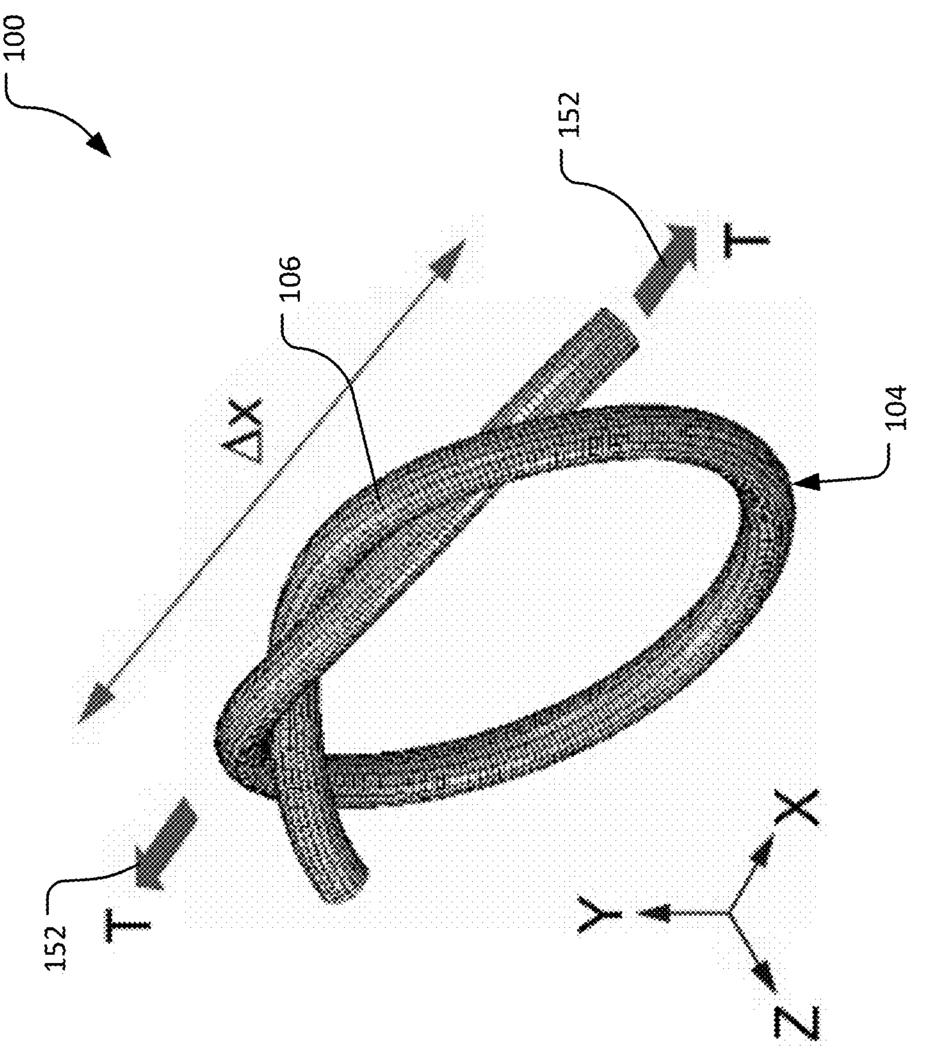
FIG. 4 is a perspective view of a restriction of a catheter system showing a restriction configured as a knot in an untightened configuration.
Figure 5:
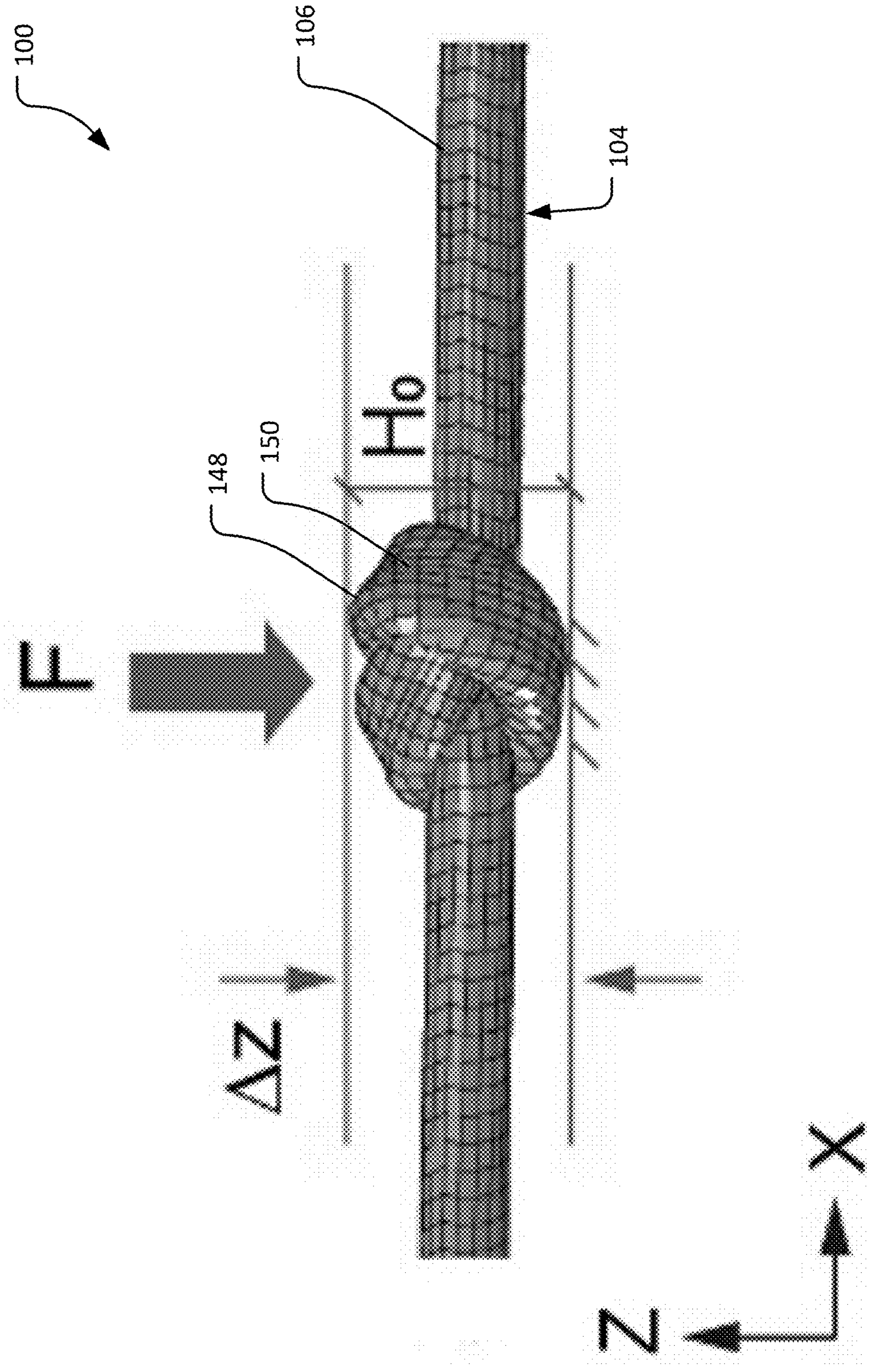
FIG. 5 is a perspective view of the restriction of FIG. 4 in a tightened configuration.

Restrictions can be formed on a tube in a number of ways, so long as the restriction causes sufficient cross-sectional narrowing of at least a portion of a lumen to achieve a desired sensitivity and correlation (e.g. a linear correlation) between a change in a desired electrical property and desired pressure range. In some configurations, the restriction may be designed to create a constraint within the lumen without completely blocking the lumen. For example, with additional reference to FIGS. 4 and 5, a restriction 148 can be a knot 150 that is formed with the tube 106. While any type of knot may be formed with the tube 106, the type of knot may be selected depending on the specific application to provide a desired sensitivity and/or correlation between a measured change in electrical property and the pressure range to be measured. In the illustrated non-limiting example, the knot 150 is configured as an overhand knot, wherein a loop is formed with the tube 106 and then an end (e.g., either of the first end 110 and the second end 112) is passed through the loop (see FIG. 4). The knot 150 is then tightened by applying tension 152 (e.g., a tensile force) to the tube 106 on opposing sides of the knot 150 (see FIG. 5). The tightening of the knot 150 causes cross-sectional narrowing of the tube 106 (e.g., the lumen 116) to form the restriction 148, with higher applied tension 152 resulting in greater cross-sectional narrowing and improving the ability to measure comparatively small pressures. In other non-limiting examples, other methods of forming restrictions can also be used, for example, by placing an O-ring or a bracket (e.g., a 3-D printed bracket) over the tube 106.

Figure 6:
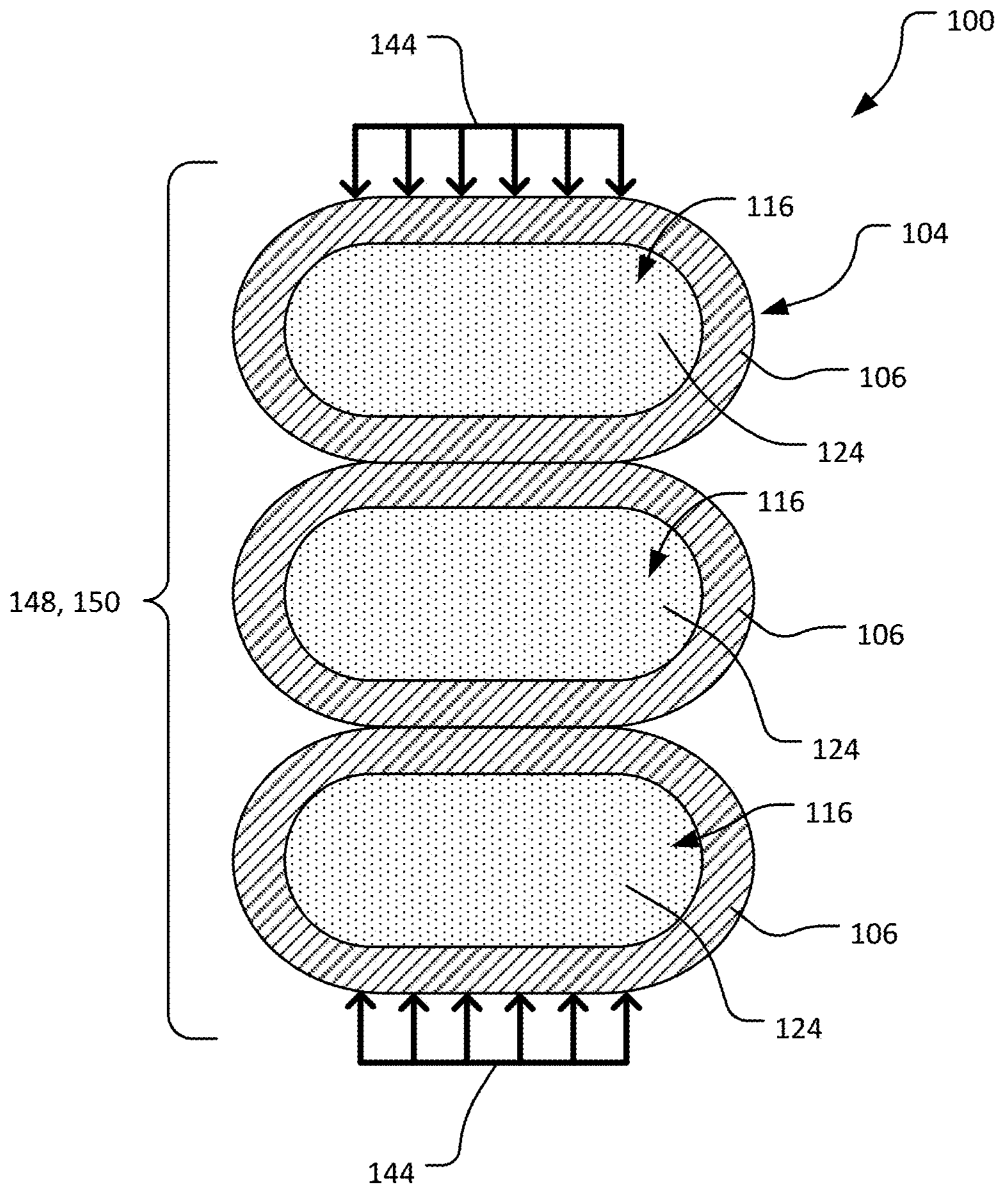
FIG. 6 is a schematic view of a cross section of the restriction of FIG. 5.

Configuring a restriction as a knot can also be useful in improving the sensitivity of a catheter system. In particular, with additional reference to FIG. 6, formation of the knot 150 effectively results in the narrowing of multiple local cross-sections of the lumen 116 at approximately the same location along the length of the tube 106. Accordingly, when a pressure 144 is applied to the knot 150, multiple local cross-sectional areas of the lumen 116 can be reduced simultaneously (although in some cases to different extents), resulting in a greater increase in, as a non-limiting example, electrical resistance. In some cases, the simultaneous compression of multiple local-cross sectional areas of a lumen 116 may provide for a more linear correlation between a measured change in resistance and an associated pressure.

Relatedly, where a restriction is configured as knot, it may be useful to use a machine to tie the knot, instead of hand-tying knots. In particular, use of a machine to tie a knot may allow for more consistent tension to be applied to the knot. Accordingly, the machine can allow for more consistent cross-sectional narrowing, which can reduce the amount of error in the pressure measurements obtained by the catheter system. Additionally, it can be beneficial to apply an adhesive to a restriction configured as a knot, or another type of restriction. For example, as illustrated in FIG. 1, an adhesive 128 can be applied to each of the restrictions 148, which can prevent the knot 150 that forms the restriction from loosening or tightening during use. Accordingly, the adhesive 128 can help to reduce errors in the pressure measurements obtained with the catheter 104. In that regard, it is preferable that the adhesive 128 is a flexible adhesive so ensure that the restrictions 148 can be deformed in order to cause the change in the electrical property.

Similarly, an adhesive can also prevent movement of a restriction along a length of a tube 106. In that regard, when a pressure is applied to a tube, a restriction can indicate a spatial coordinate (e.g., a position of the restriction along the tube) of the pressure. For example, as discussed above, the restrictions 148 are configured to allow the catheter 104 to measure pressures that are smaller than those pressures that can be measured along an unrestricted portion of the tube 106. Accordingly, when such small applied pressures are applied to an unrestricted portion of the tube 106, such as a pressure applied by a contraction of a GI tract, there is unlikely to be any measurable change in the electrical property. However, as the contraction moves along the GI tract, the contraction will eventually reach one of the restrictions, which results in sufficient narrowing of the tube to cause a measurable change in the electrical property. Thus, an applied pressure will only be detected when the pressure is applied to one of the restrictions 148.

However, where multiple restrictions are provided on the same tube to measure pressure at various locations along the catheter, it may not be possible in every case to easily distinguish which of the restrictions has been compressed. For example, in some cases, where a pressure is known to travel along a specific direction so as to occur sequentially and directionally, such as a contraction of a GI tract, the relative timing of the measured changes in the electric properties can be used to spatially resolve the location of the pressure along the catheter. However, if for example, there is a GI motility disorder that causes some of the restrictions to not be compressed, or if the pressure may be applied at random locations along the catheter, it may be difficult to discern which of the restrictions have not been compressed. Accordingly, a catheter can be configured to allow for multiplexing, which can allow the compression of one or more restrictions to be spatially resolved with respect to a position along the length of the catheter.

Figure 7:
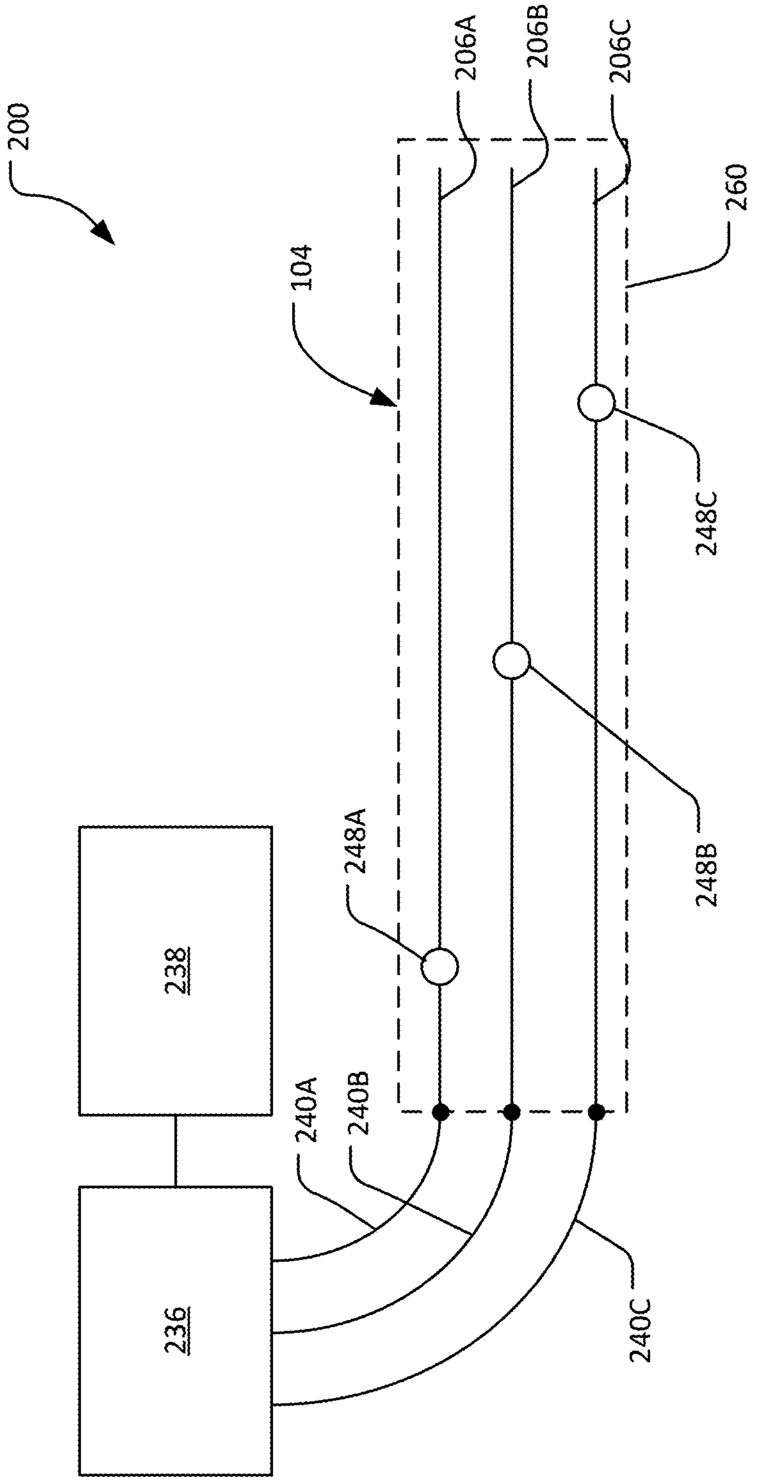
FIG. 7 is a schematic view of another exemplary catheter system according to aspects fo the disclosure, which is configured for a first mode of multiplexing.

For example, a first mode of multiplexing is illustrated in FIG. 7, showing another non-limiting example of a catheter system 200. The catheter system 200 includes a catheter 204 having a plurality of tubes 206A-C (collectively tubes 206) which can be coupled to a measurement device 236 and a processor device 238. As illustrated, each of the tubes 206A-C are configured similarly to the tube 106, except that each of the tubes 206A-C includes only a single restriction 248A-C. Each of the tubes 206A-C can be electrically coupled to the measurement device 236 (e.g., a multi-channel measurement device) so that each of the tubes 206A-C occupies a respective channel 240A-C. Additionally, the restrictions 248A-C of each of the tubes 206A-C can be spaced (e.g., evenly, or unevenly spaced) relative to one another at known distances. Thus, as each restriction 248A-C is compressed, a change in electrical properties can be measured on the respective channel 240A-C, and the location of the applied pressure along the catheter 204 will therefore be known. Accordingly, with the first mode, the catheter system 200 can spatially resolve n unique pressure measurement, where n is the number of tubes 206 of the catheter 204. Accordingly, in the illustrated non-limiting example, because the catheter 204 includes three tubes 206A-C, each with a single restriction 248A-C, three different pressures can be spatially resolved along the length of the catheter 204.

Figure 8:
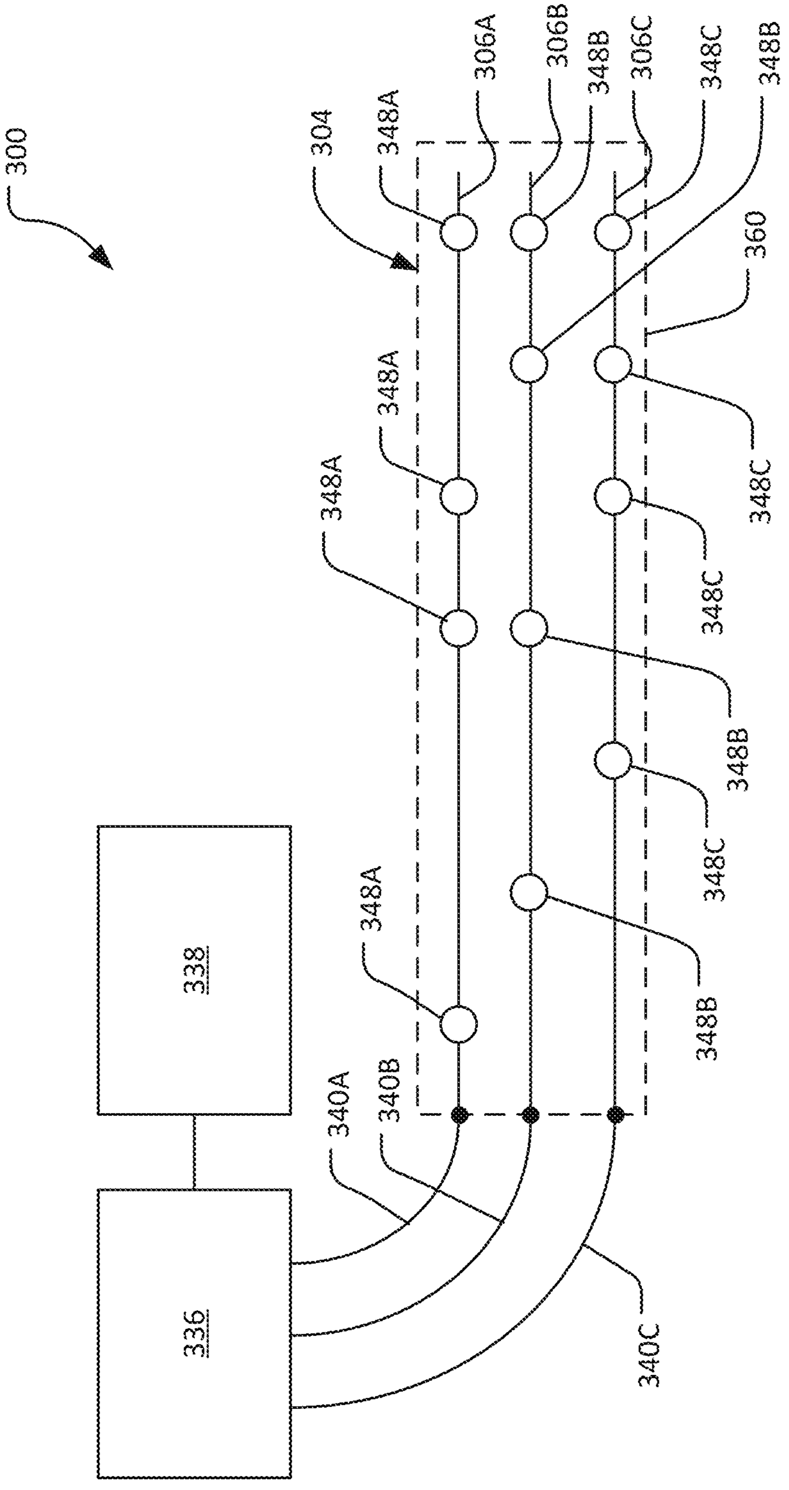
FIG. 8 is a schematic view of yet another exemplary catheter system according to aspects fo the disclosure, which is configured for a second mode of multiplexing.

As another example, a second mode of multiplexing is illustrated in FIG. 8, showing yet another non-limiting example of a catheter system 300. The catheter system 300 includes a catheter 304 having a plurality of tubes 306A-C (collectively tubes 306), each of which are generally similar to the tube 106. In particular, each of the tubes 306A-C includes a plurality of restrictions 348A-C (collectively the restrictions 348), which are positioned relative to one another along their respective lengths. More specifically, the restrictions 348 can be arranged along their respective tubes 306A-C, so that various unique combinations of restrictions 348 can be compressed simultaneously (e.g., in accordance with a binary numbering system). Thus, when each of the tubes 306A-C is coupled to a respective channel 340A-C of a measurement device 336, the catheter system 300 can spatially resolve up to 2"-3 unique pressure measurements, where n is the number of tubes. Accordingly, in the illustrated non-limiting example, the tubes 306 can spatially resolve up to seven pressure measurements along the length of the catheter 304.

Relatedly, the catheter system 300 can include a processor device 338 that can be used to decouple the various combinations of measurements to determine the magnitude and location of the pressure that is being applied to the catheter 304. That is, the processor device 338 can be in communication with the measurement device 336 so that the measurement device 336 can send the measured change in properties of each of the tubes 306A-C (e.g., a change in resistance at various combinations of the restrictions 348) to the processor device 338. Upon receiving the pressure measurements, the processor device 338 can be configured to determine the pressure being applied to the catheter 304 (e.g., to correlate the measured change in resistance with a pressure) and the location of the pressure along the catheter 304.

Where multiple tubes are used in a single catheter, it can be useful to place a sleeve around the tubes, thereby grouping the tubes together and ensuring the relative spacing of any included restrictions. For example, referring to FIGS. 7 and 8, each of the catheters 204, 304 include a sleeve 260, 360 (e.g., a main sleeve) that encloses all of the corresponding tubes 206, 306 and spatially locks each the tubes 206, 306 (e.g., the restrictions 248, 348) in the desired position, relative to one another. The sleeves 260, 360 are preferably made from a flexible material that allows compression of the restrictions 248, 348. For example, the sleeves 260, 360 can be made from a larger tube (e.g., a larger silicone tube), or from a film (e.g., a low-density polyethylene film) that can be secured around the tubes 206, 206 with an adhesive. In some cases, a sleeve can allow a catheter to be more easily disinfected using known methods (e.g., via an autoclave), or a sleeve can be configured as a disposable sleeve that can be replaced between uses. Likewise, due to the low-cost and ease of manufacturing associated with such catheter systems, the entire catheter may also be configured as a single-use catheter that can be disposed of after use, further avoiding risks of cross-contamination, avoiding the recurring maintenance and repair costs of the current expensive catheters, eliminating the need for built-in time in between cases for decontamination, and minimizing any potential delay in clinical care when the multi-use catheters are out for repair.

Figure 9:
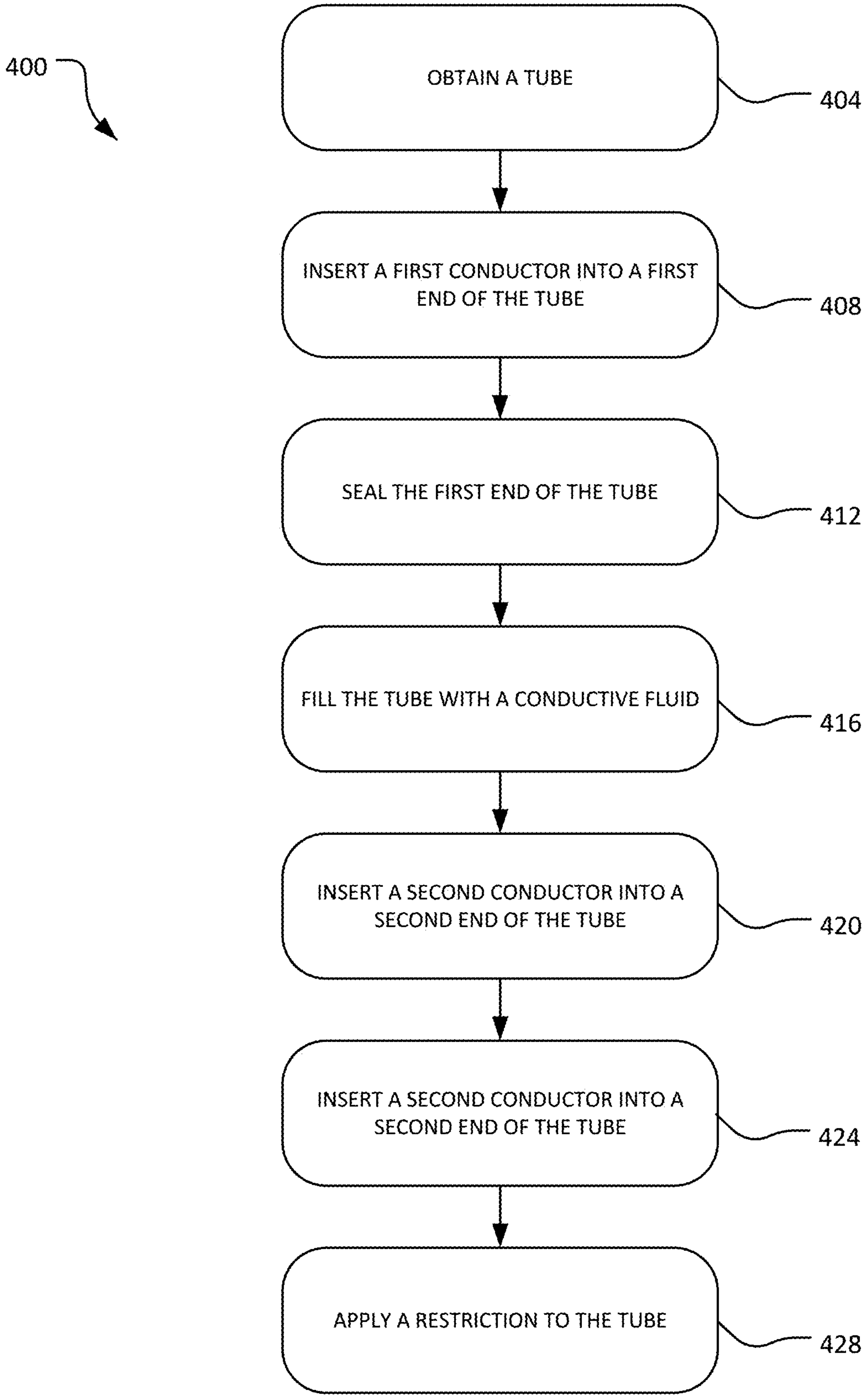
FIG. 9 is a schematic view of a method of manufacturing a catheter for use in a catheter system according to aspects of the disclosure.

Turning now to FIG. 9, a method 400 of making a catheter (e.g., a flexible pressure sensor) for a catheter system is illustrated. While details of the method 400 may be described by referring to the catheter 104 of the catheter system 100, the method 400 is equally applicable to the formation of other catheters (e.g., manometers) and flexible pressure sensors not explicitly described herein. The method 400 includes the step 404 of obtaining a tube (e.g., a flexible tube such as the tube 106). In some cases, the tube 106 can be selected in accordance with the various properties of the tube (e.g., size and material) and the specific application. For example, where the tube 106 will be used as a catheter 104 for use in GI manometry, the tube 106 may be a round, silicone tube having an external diameter of approximately 0.64 millimeters and a wall thickness of approximately 0.17 millimeters. Additionally, the step 404 may include cutting the tube 106 to a desired length (e.g., cutting a section of tubing from a larger roll of tubing). For example, the tube 106 may be cut so that the length of the tube 106 is at least as long as the portion of the GI tract to be observed, including an entirety of the GI tract. In some cases, the length of the tube 106 may be selected to account for any restrictions (e.g., knots) that are formed on the tube 106.

As discussed above, the lumen 116 defined within the tube 106 is configured to contain the conductive fluid 124, and thus electrical connections can be provided which allow a change in electrical properties of the conductive fluid 124 to be measured. Accordingly, the method 400 can further include the step 406 of inserting a conductor into an end of the tube. More specifically, in regard to the catheter 104, the first conductor 130 can be inserted into the first end 110 of the tube 106, so that a portion of the first conductor 130 is disposed within the lumen 116 and another portion of the first conductor 130 is disposed outside of the lumen 116.

Continuing, the method can further include the step 412 of sealing an end of the tube. For example, the first end 110 of the tube 106 can be sealed via a liquid-tight or gas-tight seal. More specifically, the adhesive 128 (e.g., a fast-drying silicone sealant or UV-curing sealant) can be applied to the first end 110 of the tube 106 and then cured (e.g., via an application of UV-light) to seal the first end 110. Relatedly, where, the first conductor 130 is inserted into the lumen 116 at the first end 110 prior to sealing, the adhesive 128 may be applied over the first conductor 130, which may also aid in securing the first conductor 130 in the tube 106 in the desired position. In other non-limiting examples, other types of adhesives may be used, along with other known sealing methods, for example ultrasonic welding. The method or materials (e.g., adhesives) used to seal the tube 106 may depend in part on the material of the tube 106, to ensure that a sufficient seal can be made, which should prevent any contained conductive fluid from flowing out of the tube.

At step 416, the tube can be filled with a conductive fluid. For example, the conductive fluid 124 may be poured or injected (e.g., via a syringe) into the lumen 116 of the tube 106. The method used to fill the tube 106 may depend, in part, on the material of the conductive fluid and the size of the lumen 116 formed in the tube 106. It is preferable the that the tube 106 be completely filled with the conductive fluid 124 to ensure electrical continuity along the length of the tube 106, however, this may not always be the case.

At step 420, a second conductor can be inserted into an end of the tube. More specifically, the second conductor 132 can be inserted into the opposing end (e.g., the second end 112) of the tube 106, so that a portion of the second conductor 132 is disposed within the lumen 116 and another portion of the second conductor 132 is disposed outside of the lumen 116.

At step 424, a second, opposing end of the tube can be sealed. In particular, as similarly discussed above with respect to sealing of the first end 110, adhesive 128 can be applied to the second end 112 of the tube 106 and then cured to seal the second end 112. Relatedly, where, the second conductor 132 is inserted into the lumen 116 at the second end 112 prior to sealing, the adhesive 128 may be applied over the second conductor 132, which may also aid in securing the second conductor 132 in the tube 106 in the desired position. Accordingly, with both ends 110, 112 sealed, the tube 106 will be a sealed tube and the conductive fluid 124 will be contained in the lumen 116 defined therein.

Where greater sensitivity to pressure is required, such as when measuring small pressures generated by contractions of a GI tract, the method 400 can further include the step 428 of applying (e.g., forming) a restriction on the tube. For example, the restrictions 148 are each formed by tying a knot 150 (e.g., an overhand knot, in accordance with the discussion above) with the tube 106. However, other types of restriction can also be used, for example, attaching (i.e., placing) an O-ring or bracket (e.g., a 3D-printed bracket) on the tube 106. The step 428 can be repeated to form multiple restrictions 148 on the tube 106, with the number and spacing of the restrictions varying depending on the specific application. In that regard, the restrictions 148 can be evenly or unevenly spaced along the tube 106 and the specific position of the restrictions can be selected to allow for various catheter configurations, including catheters configured for multiplexing. Additionally, the spacing of the restrictions formed on the tube can be customizable. That is, the spacing of the restrictions can be customized for a specific application, for example, to provide a higher number of pressure measurements (e.g., higher packing density) near an area of concern within a GI tract, without interference or deterioration of signal quality. In particular, such increased packing density can help identify physiologically distinct anatomical segments of a GI tract, such as the proximal (skeletal muscle) portion versus the distal (smooth muscle) portion for esophageal manometry. Relatedly, restrictions can be formed closer together (e.g., with spacings of less than 5 millimeters between adjacent restrictions), as compared with current HRM systems (e.g., with spacings of approximately 10 millimeters or greater).

Experimental Results

The pressure sensor described below was built and characterized to show good sensitivity in the human gastrointestinal (GI) pressure range (e.g., approximately 0 mmHg to 250 mmHg) and is compatible with autoclave to facilitate sterilization for clinical use. The pressure sensor is configured as a simple and low-cost soft pressure sensor (SPS), in the form of a long (up to several meters) and thin (diameter of approximately 0.6 millimeters) silicone/liquid metal composite (e.g., a silicone catheter containing a conductive fluid) with hand or machine tied knots configured to act as pressure-sensitive nodes, which can convert applied pressure at the knotted locations into spatially-resolved (electrical) resistive changes in the liquid metal conductors. The SPS is compatible with autoclaves, highly reconfigurable and scalable in terms of sensor locations, numbers, and overall length, require only a medium-priced multimeter as the recording hardware, while offering acceptable sensitivity in the human GI pressure ranges. The low toxicity of liquid metal and small overall sensor diameters ensure good safety of the device during deployment into the GI tract. An SPS according to the present disclosure can be manufactured using simple fabrication schemes, which can be completed using basic bench tools, resulting in a device that costs substantially less than conventional GI manometer systems. In some cases, an SPS can exploit machine-aided fabrication and finite element (FE) simulations for enhanced sensor performances and strategies to multiplexed measurements.

The SPS was further benchmarked against clinically available GI pressure sensors, for example, endoluminal functional luminal-imaging probe (EndoFLIP) and HRM, in vivo using porcine models to show comparable performances in evaluating certain pressure activities detailed in the examples below. Through in vitro tests, we validate the system for pressure sensing in a wide range of force scenarios. We further demonstrate clinical utility of the system by investigating simulated esophageal motility, induced swallowing reflex, and rectoanal inhibitory reflex (RAIR) in Yorkshire swine models, and by benchmarking against the commercially available EndoFLIP and HRM technologies.

In general, a simple yet functional pressure sensor can be built by infusing elastic medical catheters (e.g. silicone tubing with outer diameters ranging between 0.64 millimeters and 1.96 millimeters) with liquid metals and sealing both ends. In particular, eGaIn was found to be a good pressure-sensing component due to its liquid nature under body conditions (e.g., with a melting point at approximately 15.5 degrees Celsius), low viscosity (e.g., approximately $1.99\times10^{-3}$ pascal-seconds, Pa·s), excellent electrical conductivity (e.g., approximately $3.4\times10^{6}$ S/m), great moldability, and low cytotoxicity. Thus, the resulting pressure sensor can be made of medically approved encapsulation materials and integrated into a catheter configuration, which facilitates clinical implementations.

The silicone/liquid metal composite undergoes cross-sectional narrowing if sufficient pressure is applied, resulting in an increase in the electrical resistance across the liquid metal conductor (e.g., eGaIn) due to the piezoresistive effect. However, in some cases, the pressure generated from typical human GI contractions (e.g., 0 mmHg to 250 mmHg) may be incapable of causing sufficient narrowing of the catheter, leading to negligible resistive changes ($\Delta R/R_0$) and pressure sensitivity (see FIG. 10), which were characterized using a customized mechanical compression system shown in FIG. 11). Additionally, depending on the configuration of the SPS, there may be no way to identify the spatial location of the pressure source as the catheter has a uniform cross-sectional area throughout.

Figure 10:
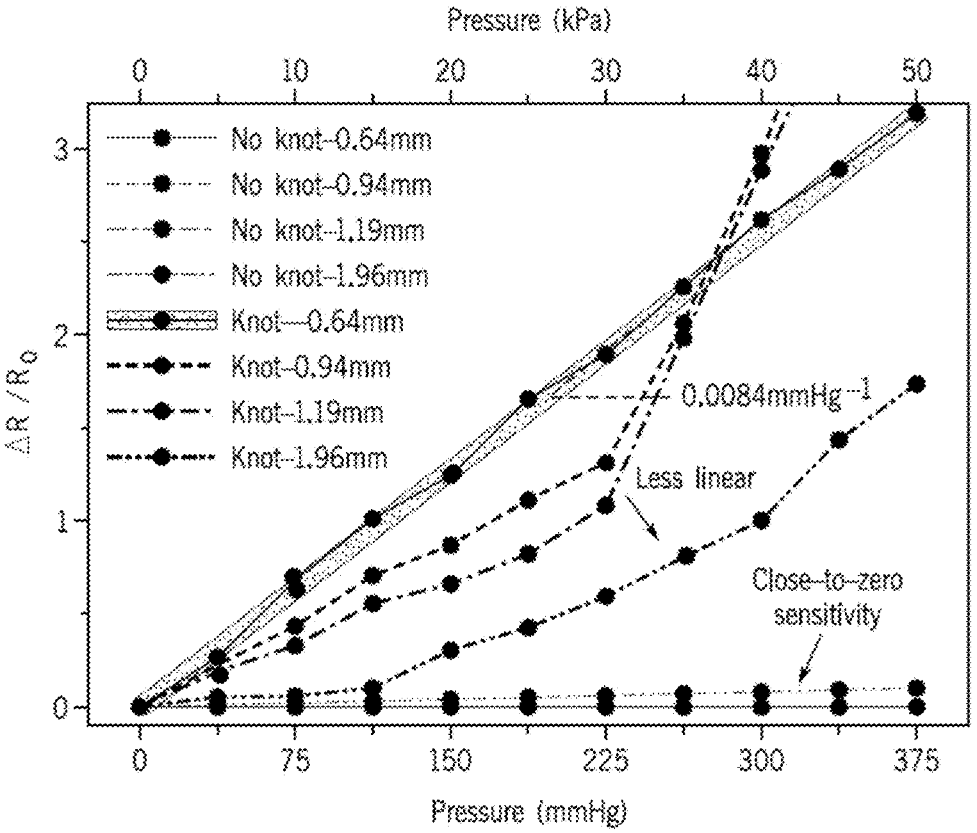
FIG. 10 is a plot showing a change in electrical resistance ($\Delta R/R_0$) of liquid metal-infused silicone tubing with different outer diameters as a function of applied pressure.
Figure 11:
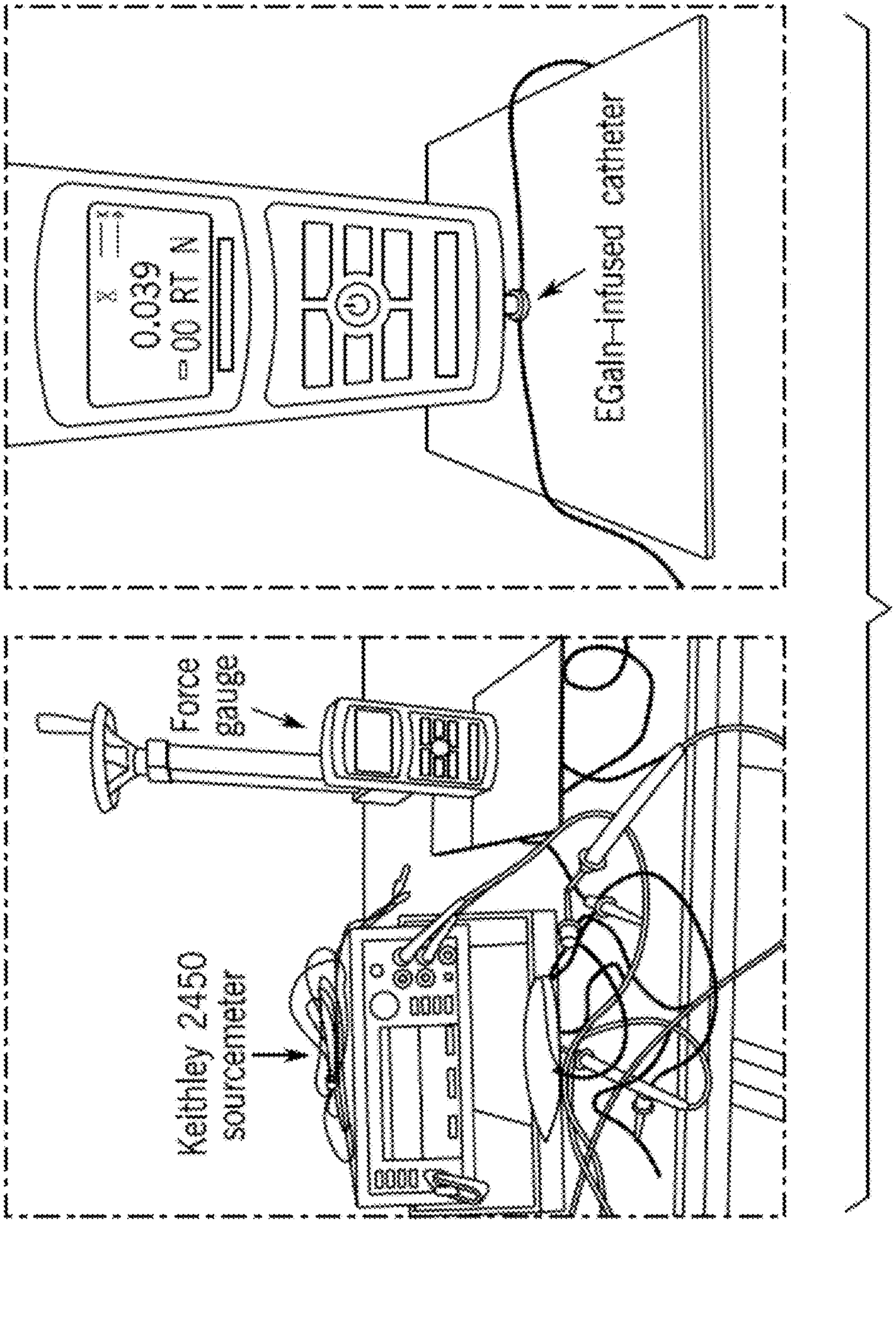
FIG. 11 is an image of a measurement system used for characterizing pressure sensor performance.
Figure 12:
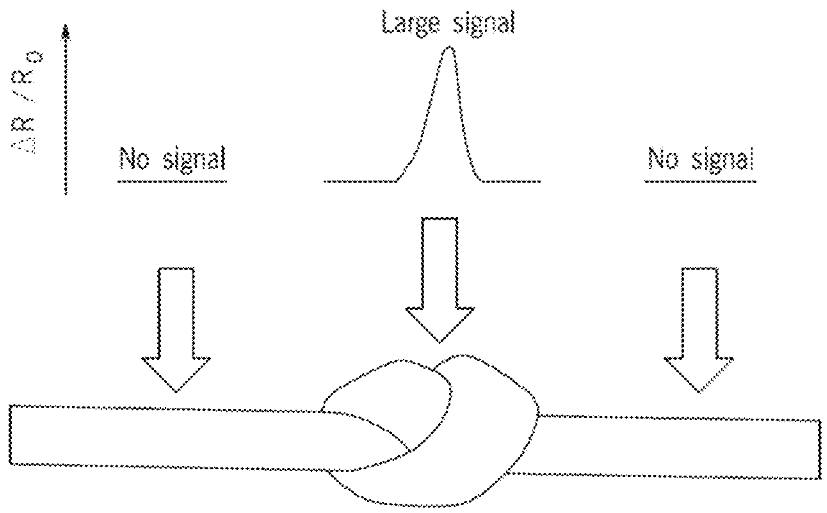
FIG. 12 is a schematic view illustrating operation a pressure sensor, according to aspects of the disclosure, showing that a change in electrical resistance is only detected when a pressure is applied to a restriction (e.g., a knot).
Figure 13A:
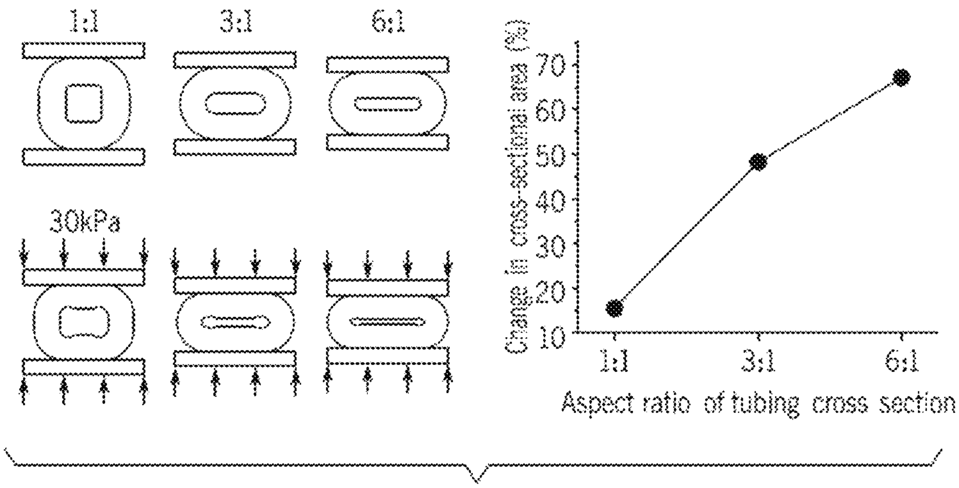
FIG. 13A is a schematic view illustrating different aspect ratios of a tubing cross section, and that electrical resistance increases as the total cross-sectional area decreases and the aspect ratio increases.
Figure 13B:
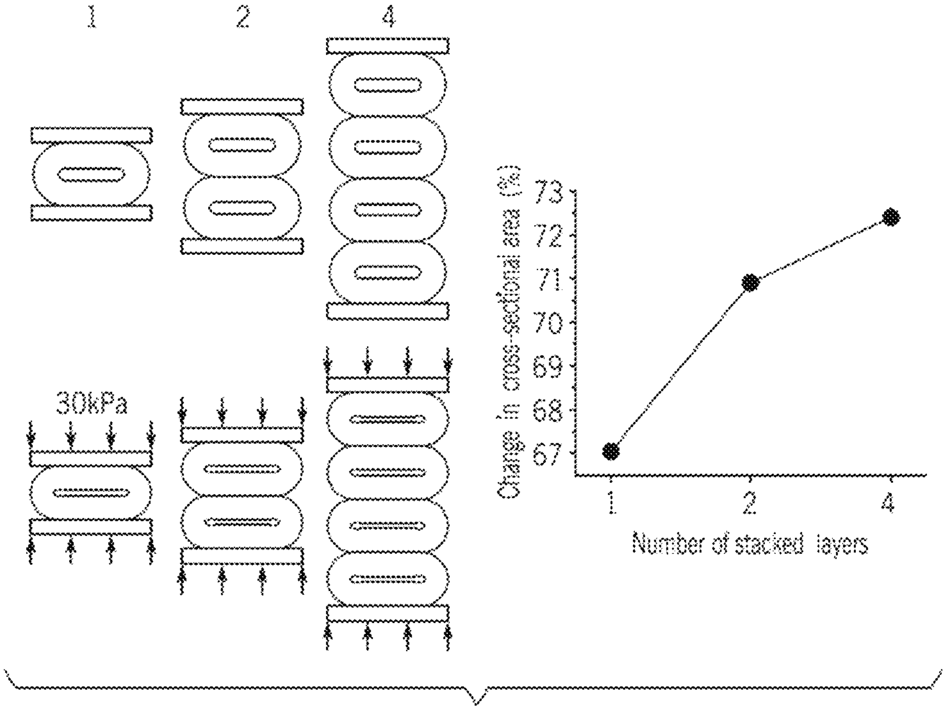
FIG. 13B is a schematic view showing three different aspect ratios of stacked tubing cross sections, and that electrical resistance increases as the total cross-sectional area decreases and the aspect ratio increases.

That being said, experimental data has shown that both issues can be simultaneously eliminated by tying knots (e.g., forming restrictions) on the silicone/liquid metal composite (see FIG. 10). Thus, not only do the knots exhibit a highly linear (e.g., an $R^2$ value greater than approximately 0.985), low-hysteresis (e.g., a hysteresis error of less than approximately 0.5-percent) response in the human GI pressure range (see FIG. 10), but they also acted as spatial coordinates of the pressure source since they were more pressure-sensitive than the neighboring, unknotted portions of the catheter (see FIG. 12, showing a large change in electrical resistance through the eGaIn-infused catheter was recorded by a resistance measurement device when a small pressure, e.g., less than 50 kPa, was applied onto the knots, whereas no signal was detected when the pressure was applied onto the neighboring, unknotted region). In particular, forming knots on the catheter increased the aspect ratio of the catheter cross-section due to shear stress (see FIG. 6), which made it more sensitive to deformations than the unknotted case under the same loading conditions. Additionally, similar to serially connected springs, each catheter layer that was folded and stacked onto itself due to knotting experienced the same external pressure component perpendicular to the stacking plane, resulting in an amplification of the effective total pressure. FE simulations were used to verify that an increase in the aspect ratio of the catheter cross-section as well as in the number of the stacked catheter layers contributed to a larger change in the total cross-sectional area under the same loading conditions (see FIG. 13A, showing three different aspect ratios of tubing cross section (1:1, 3:1, and 6:1) representing different degrees of knotting (no knot, loose knot, and tight knot) were subject to the same pressure of 30 kPa, which showed an increase in the change in total cross-sectional area as the aspect ratio increased, and FIG. 13B, showing three different numbers of stacked layers (1, 2, and 4) were subject to the same pressure of 30 kPa, which showed an increase in the change in total cross-sectional area as the number of stacked layers increased).

Figure 14:
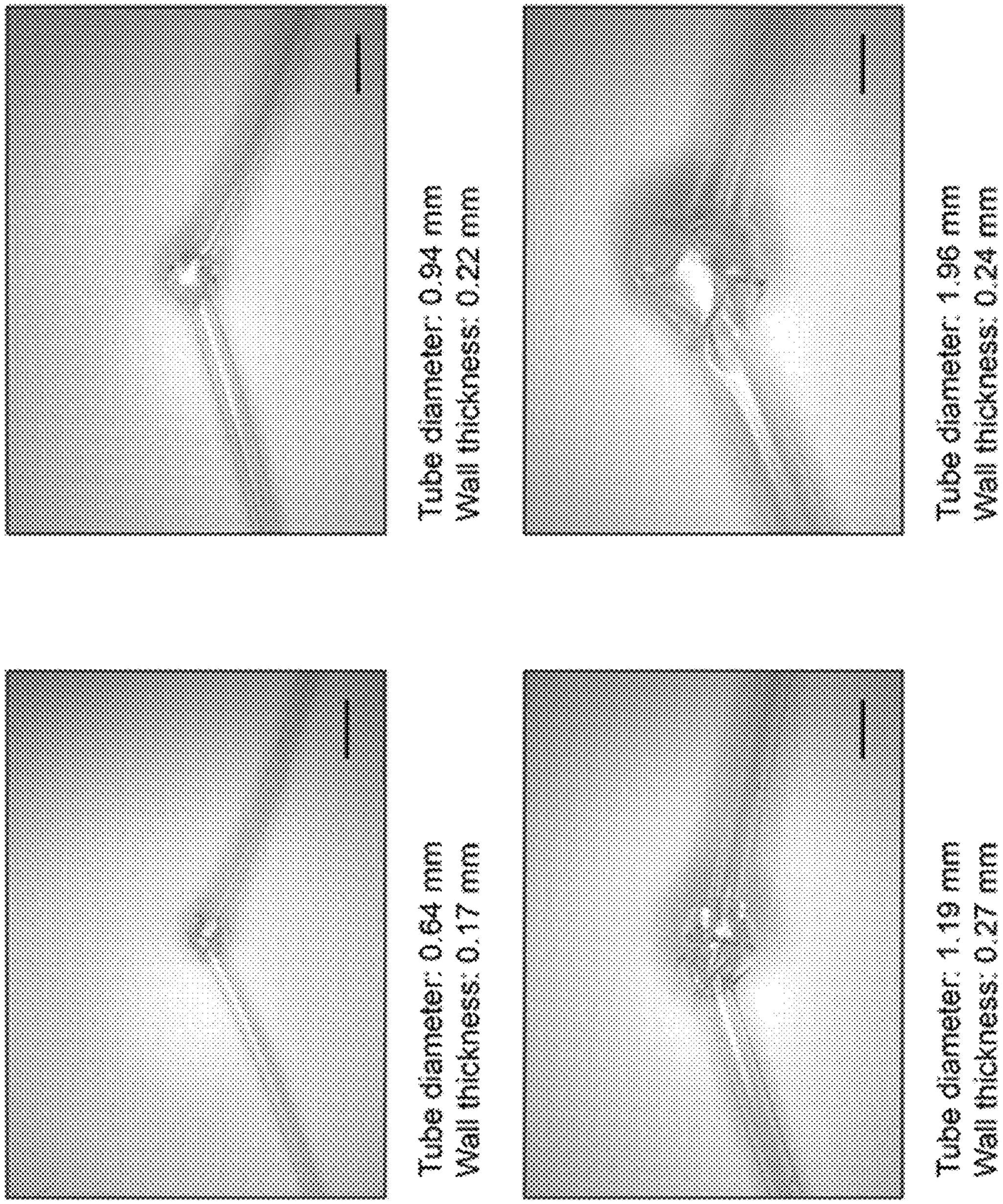
FIG. 14 is a schematic view illustrating that increasing distortion in knot geometries is associated with increased tube diameters, while wall thicknesses remained constant.

We experimented on a range of catheter diameters and found that the resulting knots became increasingly distorted as the outer diameter (OD) increased from 0.64 millimeters to 1.96 millimeters (see FIG. 14), which manifested in both lower sensitivity (i.e., the slope of the curve) and shorter linear regimes (see FIG. 10). Silicone tubing with the outer diameter and wall thickness of 0.64 millimeters and 0.17 millimeters, respectively, exhibited the highest linear sensitivity of 0.0084 $mmHg^{-1}$ in the human GI pressure range among commercially available options, and was therefore chosen for the rest of the study unless stated otherwise.

Figure 15:
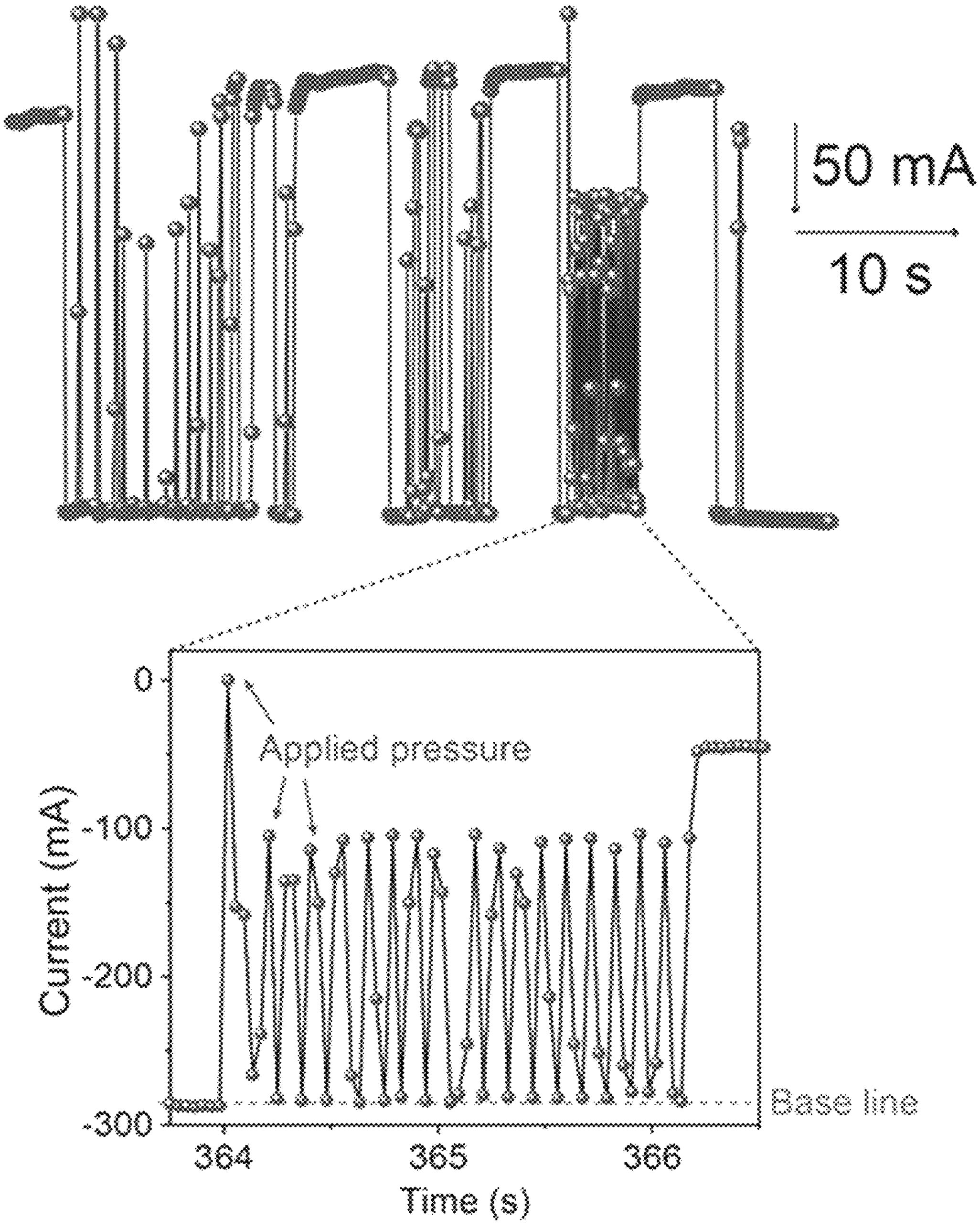
FIG. 15 is a plot illustrating the temporal resolution of a flexible (e.g., soft) pressure sensor according to aspects of the disclosure.
Figure 16:
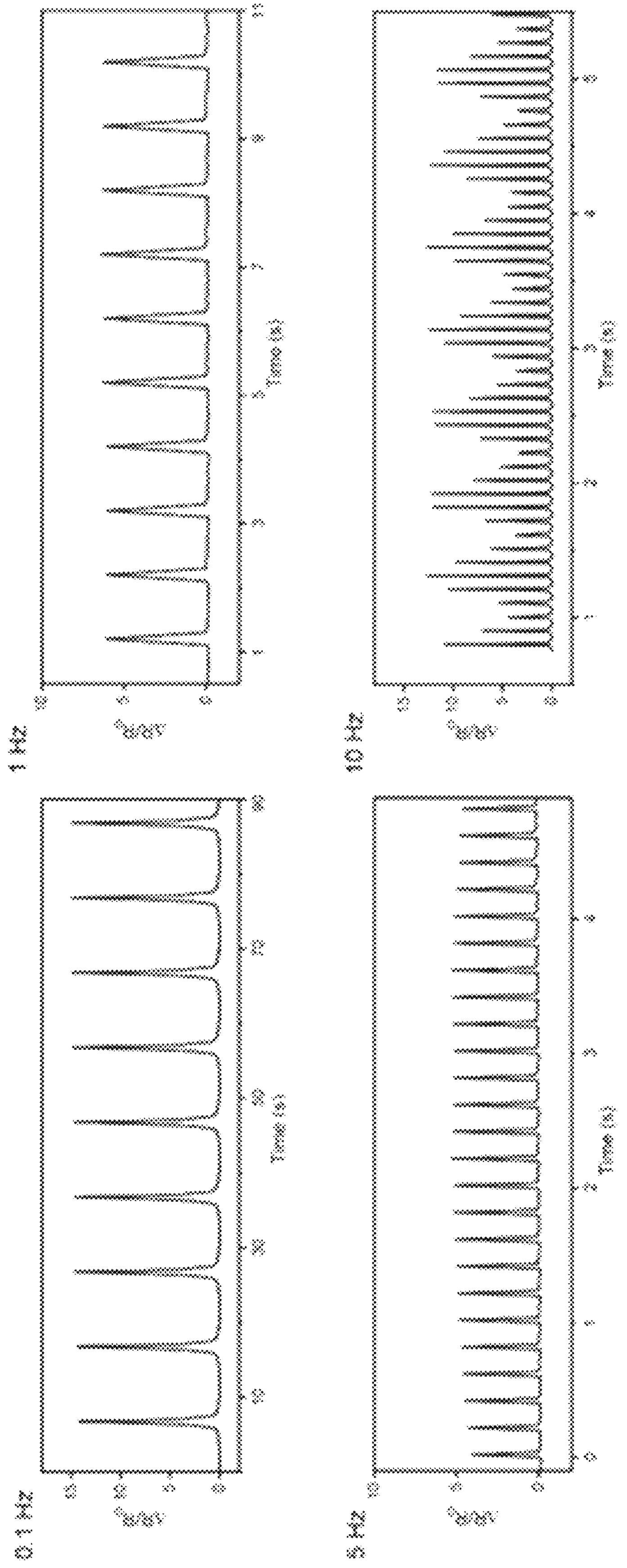
FIG. 16 is a series of plots illustrating a measured change in electrical resistance of a flexible pressure sensor as a function of time for different frequencies of applied cyclic compressions.

The SPS showed a temporal resolution of approximately 10 Hertz, as well as a stable baseline for at least 400 seconds of continuous operation without using a Wheatstone bridge circuit (FIG. 15). To evaluate the frequency response of the SPS, we performed cyclic compression tests at several different frequencies between 0.1 Hertz and 20 Hertz using a tensile testing machine. As illustrated in FIG. 16, showing the measure change in resistance ($\Delta R/R_0$) as a function of time at different frequency of cyclic compressions, the signal fidelity was well-preserved at frequencies below 5 Hertz. Overall, the frequency range (e.g., approximately 0.1 Hertz to 5 Hertz) of the SPS is lower than commercial pressure sensors based on piezoelectric materials, but still adequate for evaluating GI motility that has a typical frequency on the order of 1 Hertz and lower.

Figure 17:
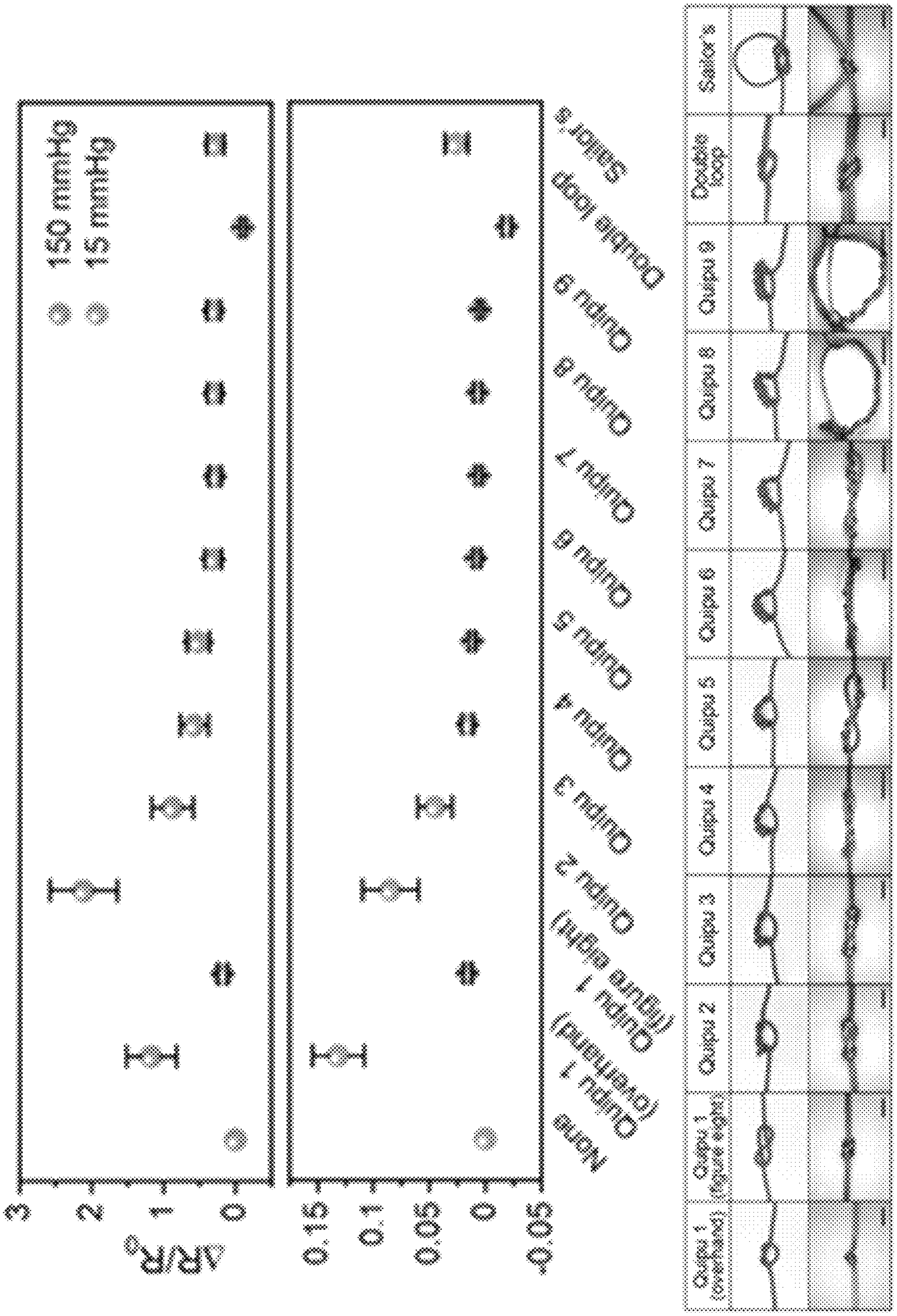
FIG. 17 is a schematic view illustrating various knot types and their corresponding measured changes in electrical resistance.

Additionally, we explored the effects of different knot types on pressure sensitivity. Resistive change ($\Delta R/R_0$) at the low pressure (15 mmHg) and the high pressure (150 mmHg) of twelve different knot types exhibited a wide distribution (see FIG. 17, showing images of the twelve different knot types (scale bars of approximately 2 millimeters) and the corresponding large-scale models to illustrate the knotting process; data reported as mean±standard deviation for n>5 measurements for each group). It is worth noting that the knots generated from silicone tubing deviated geometrically from the large-scale models using polypropylene ropes as the knot complexity increased (see FIG. 17), likely due to the viscoelastic nature of silicone materials. This study demonstrates the potential to tailor sensitivity for specific application needs using different knot geometries, a concept similar to differentiating numbers and letters in the quipu.

Figure 18A:
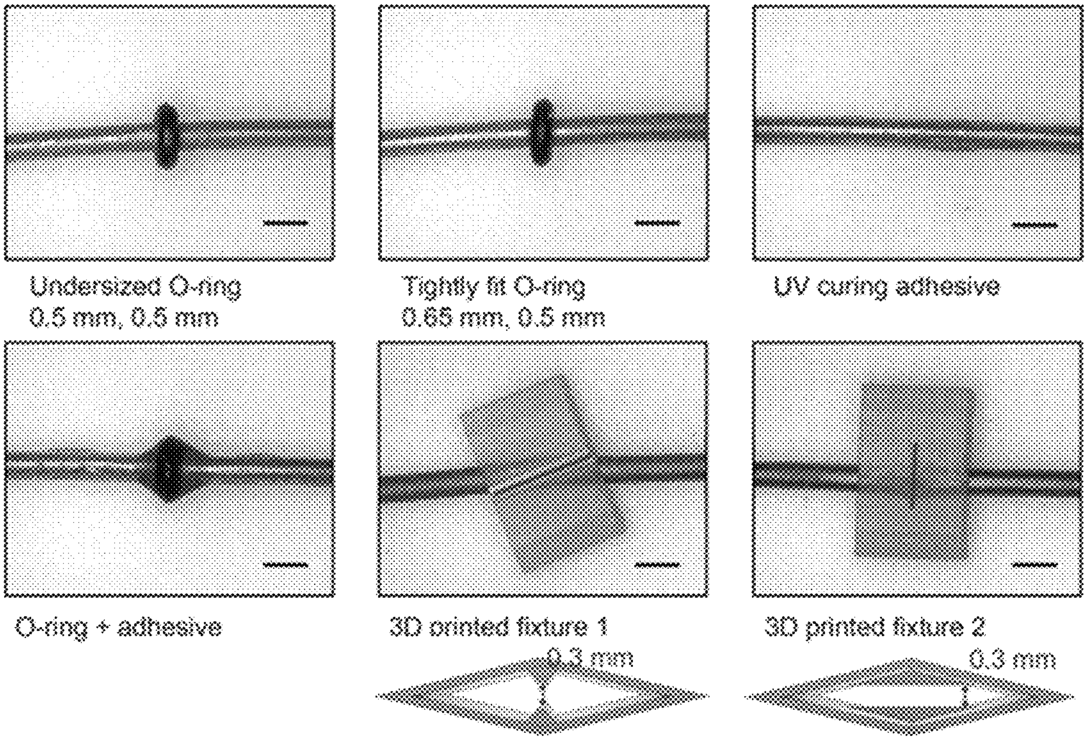
FIG. 18A is a perspective view showing various types of restrictions according to aspects of the disclosure.
Figure 18B:
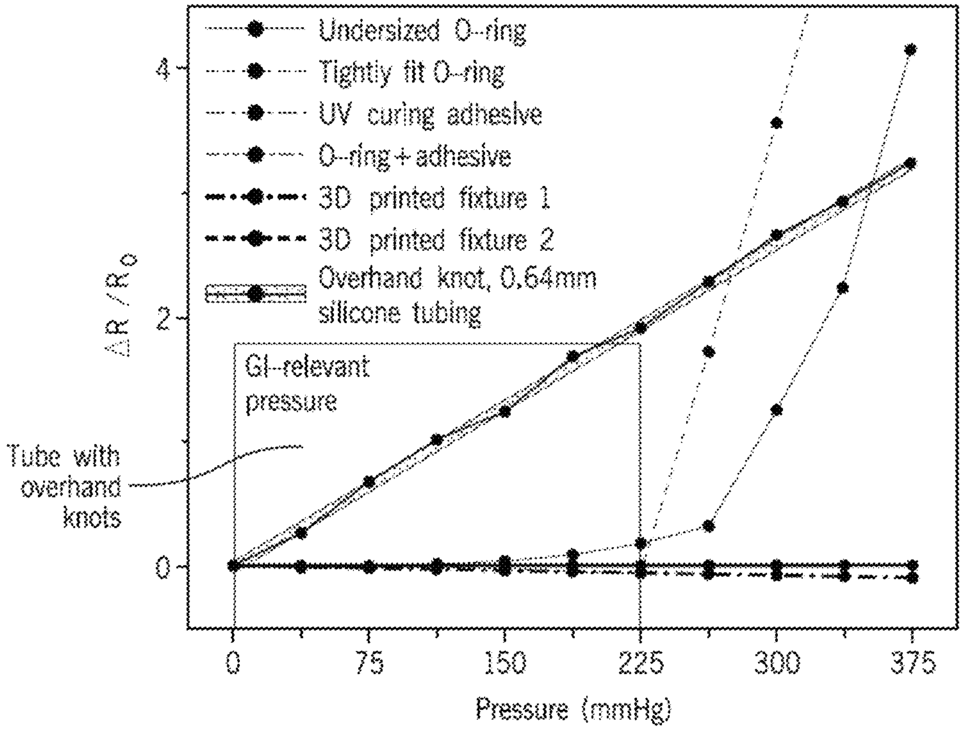
FIG. 18B is a plot illustrating a measured change in electrical resistance as a function of applied pressure for the restrictions shown in FIG. 18A.

We further tested the alternatives to knots as localized stress concentrators on the silicone tubing, such as O-rings and/or ultraviolet (UV) curing adhesive, and 3D printed micro-fixtures; none of which resulted in as good linear sensitivity as the overhand knots in the GI-relevant pressure range. In particular, as illustrated in FIG. 18A (scale bars of 1 millimeter), alternative stress concentrators included an undersized O-ring (0.5 millimeters inner diameter, 0.5 millimeters wall thickness), a tightly fit O-ring (0.65 millimeters inner diameter, 0.5 millimeters wall thickness), a UV curing adhesive, a tightly fit O-ring plus UV curing adhesive, and two 3D printed fixtures. With additional reference to FIG. 18B, resistive changes ($\Delta R/R_0$) as a function of applied pressure using the alternative stress concentrators of FIG. 18A were measured, with a curve for silicone tubing with a diameter of 0.64 millimeters having overhand knots shown for comparison. In other non-limiting examples, methods such as laser texturing can be used to modify the tubing surface to induce changes in mechanical behaviors in response to pressure. The overhand knots were used for the rest of the study unless stated otherwise.

Figure 19:
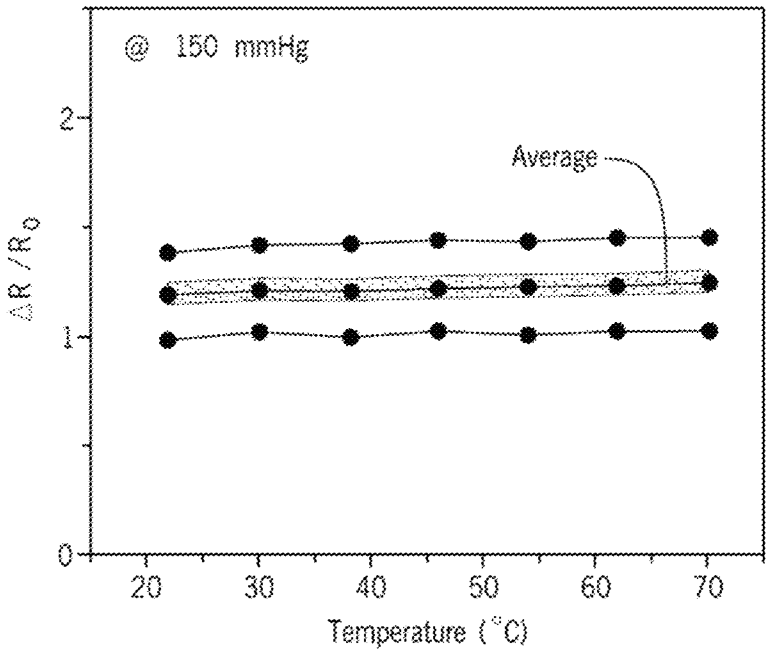
FIG. 19 is a plot illustrating a measured change in electrical resistance for an applied pressure of approximately 150 mmHg as a function of soaking time as a function of temperature, for a soft pressure sensor (SPS) with a restriction configured as an overhand knot.
Figure 20:
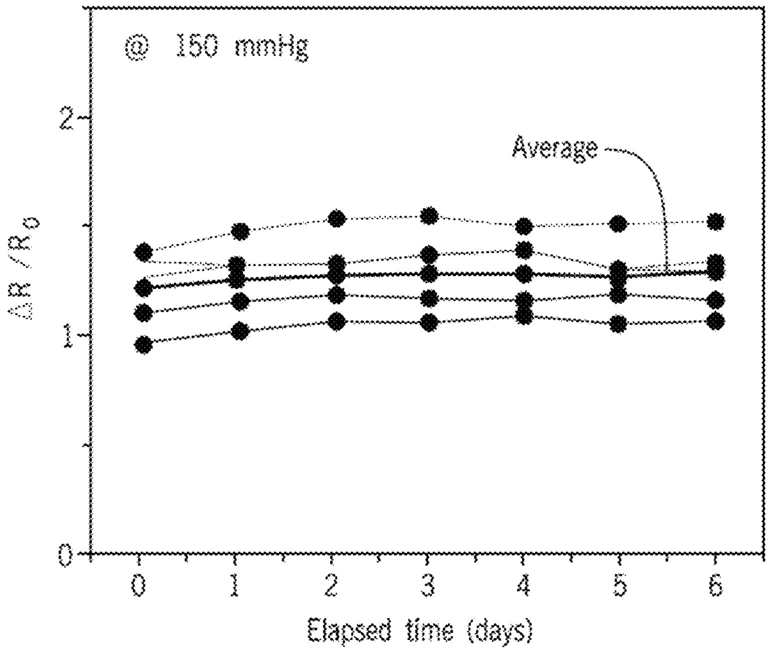
FIG. 20 is a plot illustrating a measured change in electrical resistance for an applied pressure of approximately 150 mmHg as a function of soaking time in a phosphate-buffered saline solution held at approximately 37 degrees Celsius, for an SPS with a restriction configured as an overhand knot.
Figure 21:
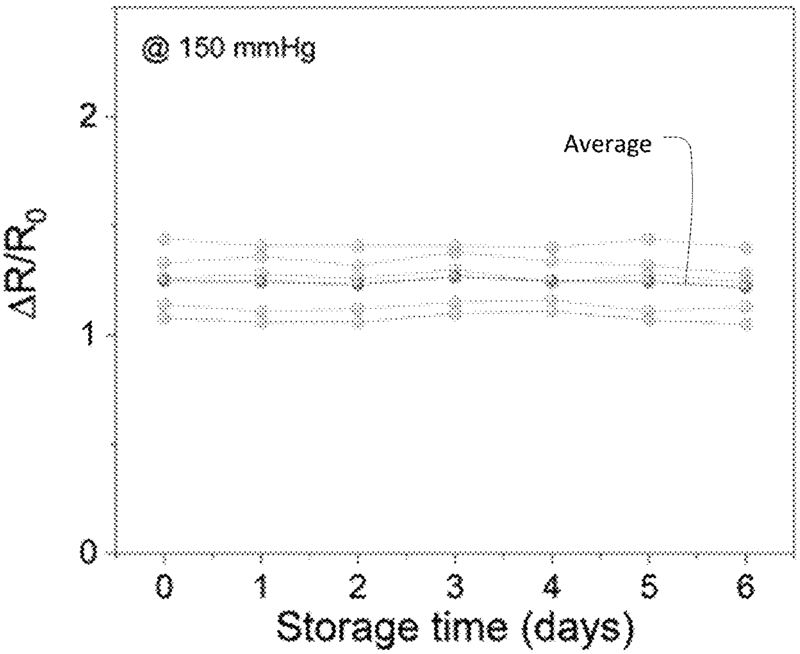
FIG. 21 is a plot illustrating a measured change in electrical resistance for an applied pressure of approximately 150 mmHg as a function of time, for an SPS with a restriction configured as an overhand knot.

Next, we characterized the robustness of the SPS through a heating test up to 70 degrees Celsius (see FIG. 19, showing $\Delta R/R_0$ at 150 mmHg pressure as a function of temperature) and a soaking test in a 37 degree Celsius phosphate-buffered saline up to one week (see FIG. 20, showing $\Delta R/R_0$ at 150 mmHg pressure as a function of soaking time in 37 degrees Celsius phosphate-buffered saline), during which the changes in sensitivity were within 4.3-percent and 6.1-percent, respectively. The thermal influence on sensitivity was approximately 4.3-percent, which can be further improved by the addition of a Wheatstone bridge circuit that was not included in this work due to cost and manufacturing considerations. In addition, we performed storage tests of the SPS under normal laboratory conditions (e.g., approximately 22 degrees Celsius, approximately 20-percent relative humidity) for one week. The averaged change in $\Delta R/R_0$ between day 0 and day 6, approximately negative 2.4-percent (see FIG. 21), was smaller than those from the heating and soaking tests, indicating that the SPS has a good shelf stability for at least one week.

Figure 22:
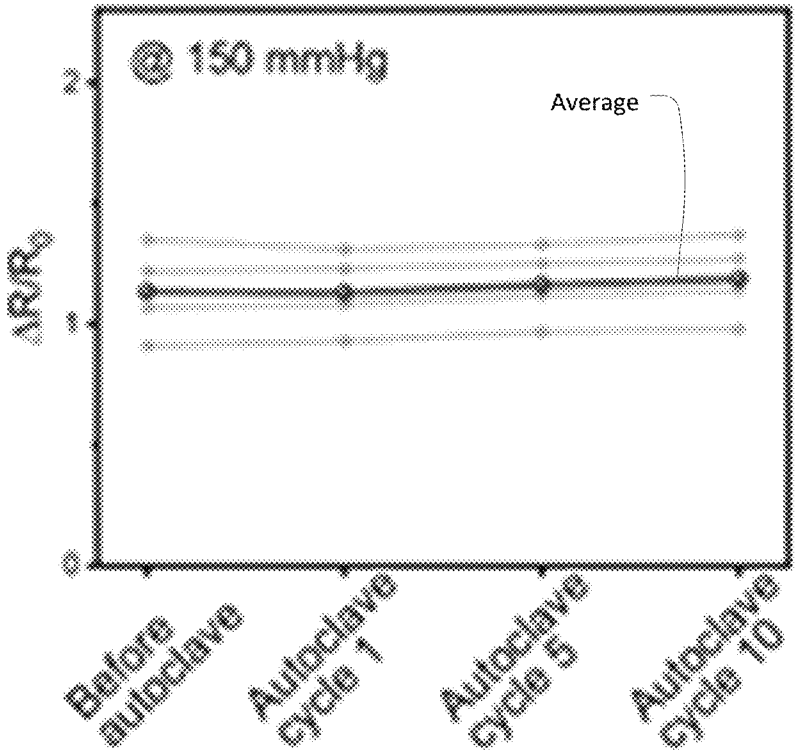
FIG. 22 is a plot illustrating a measured change in electrical resistance for an applied pressure of approximately 150 mmHg as a function of a number of autoclave cycles, for an SPS with a restriction configured as an overhand knot.
Figure 23:
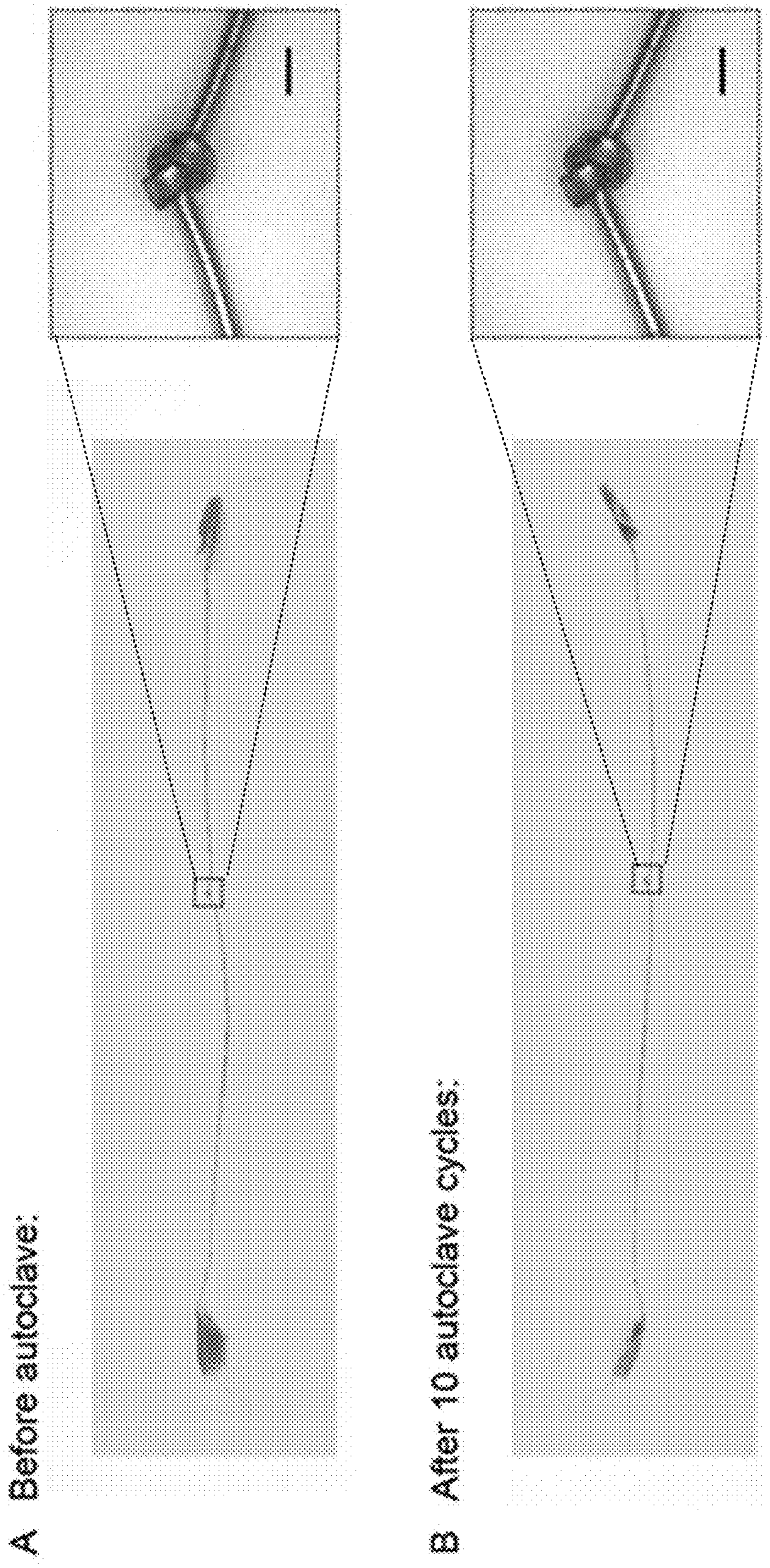
FIG. 23 is a perspective view comparing the SPS of FIG. 22 before and after ten autoclave cycles.

Another important feature of reusable medical devices is the compatibility with an autoclave for quick and effective sterilization, one that the SS systems lacked due to the delicacy of the electronic components. We found that the change in sensitivity of the SPS was within 5.2% after undergoing at least ten standard autoclave cycles (e.g., approximately 121 degrees Celsius, at 1 atmosphere for 30 minutes, see FIGS. 22 and 23).

To determine the degree of potential eGaIn leakage and to assess safety of the device in vivo, we immersed the SPS in simulated gastric fluid (e.g., with a pH of approximately 2) at approximately 37 degrees Celsius for approximately 1 hour, which represent conditions that such devices may encounter in the GI tract. No change in color of the solution was found after 1 hour. We then dried the devices overnight and found the weight changes before and after immersion to be only 0.9-percent, plus or minus 0.2-percent, indicating that almost no substance exchange has occurred with the surrounding medium under these extreme testing conditions.

Enhancing Sensor Performance

Figure 24:
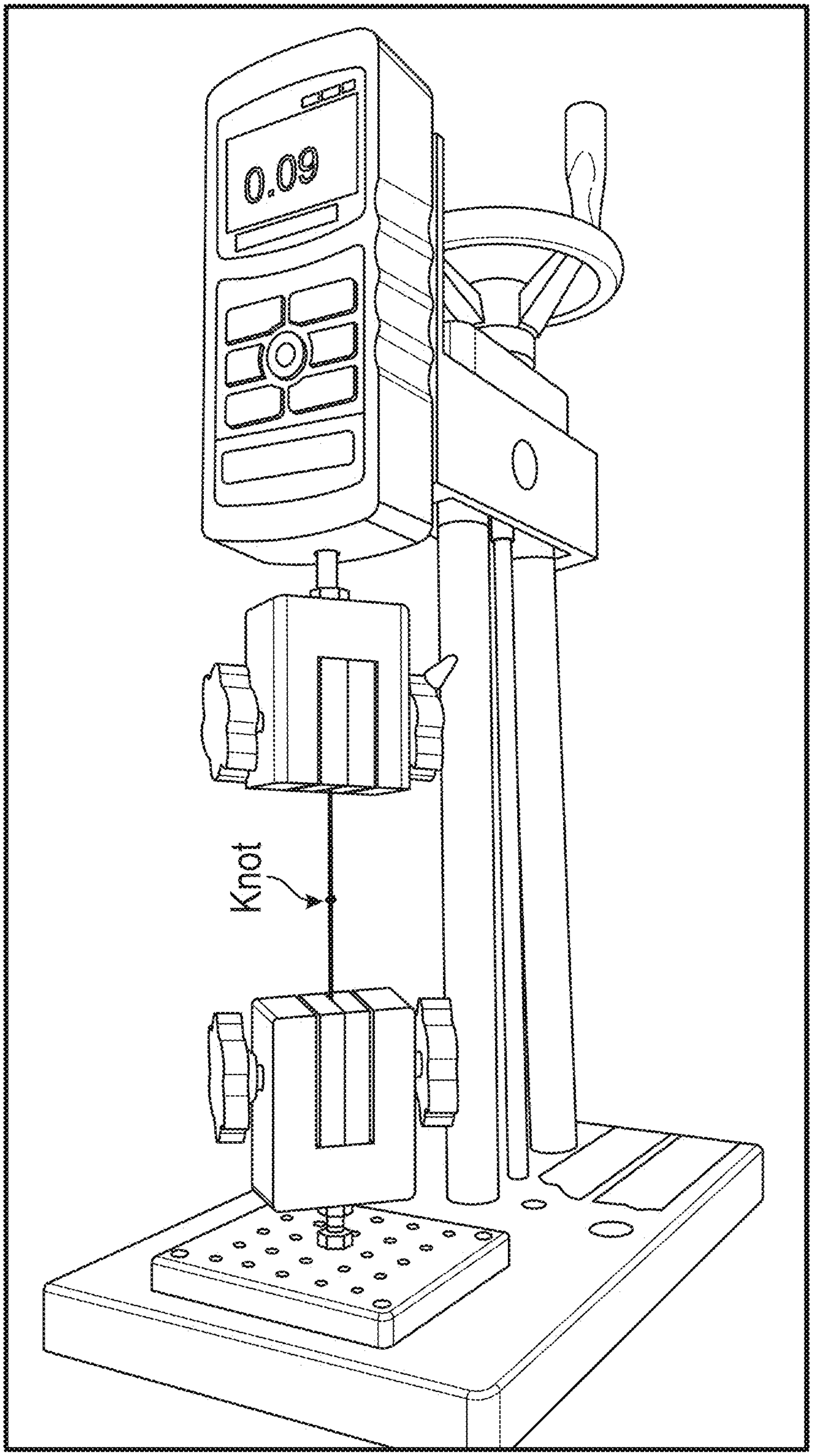
FIG. 24 is an image of a mechanical stretching machine used to form machine-tied knots.
Figure 25:
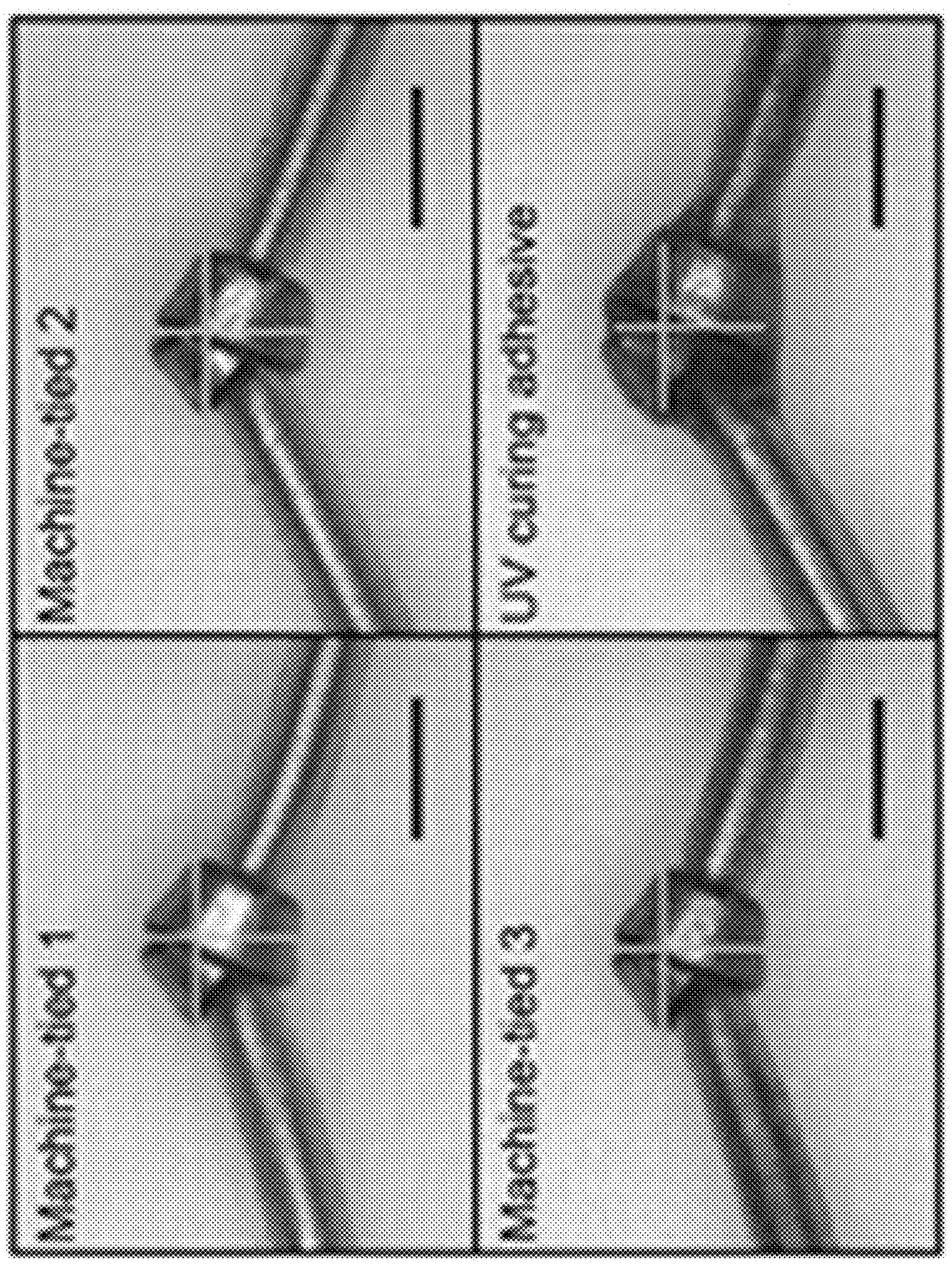
FIG. 25 is an image of a number of machine-tied knots formed with the mechanical stretching machine of FIG. 24, with and without a curing adhesive.

While the ability to assemble the entire SPS with basic bench tools can achieve simplicity and reduce cost, frugality, a mechanical stretching system with an integrated force gauge (see FIG. 24) for precise control over the knotting process can further improve sensor accuracy and sensitivity. For example, it was determined that a tensile force of approximately 0.1 newtons yielded high-quality knots in terms of consistency and sensitivity (see FIG. 25, showing images of machine-tied knots with and without UV curing adhesive, with identical yellow reference cross showing good qualitative geometric consistency; UV curing adhesive resulted in slightly expanded knot volume, scale bars of approximately 1 millimeter). Additionally to prevent changes in sensitivity due to knot movement during use, approximately 0.2 milliliters of UV curing adhesive was applied to the knots (see FIG. 25) that, upon curing, successfully locked its shape against stretching, at the expense of some sensitivity (see FIG. 26, showing resistive changes ($\Delta R/R_0$) of hand-tied, machine-tied, and machine-tied with UV curing adhesive samples as a function of applied pressure, with data reported as mean±standard deviation for n>5 measurements for each group).

Figure 26:
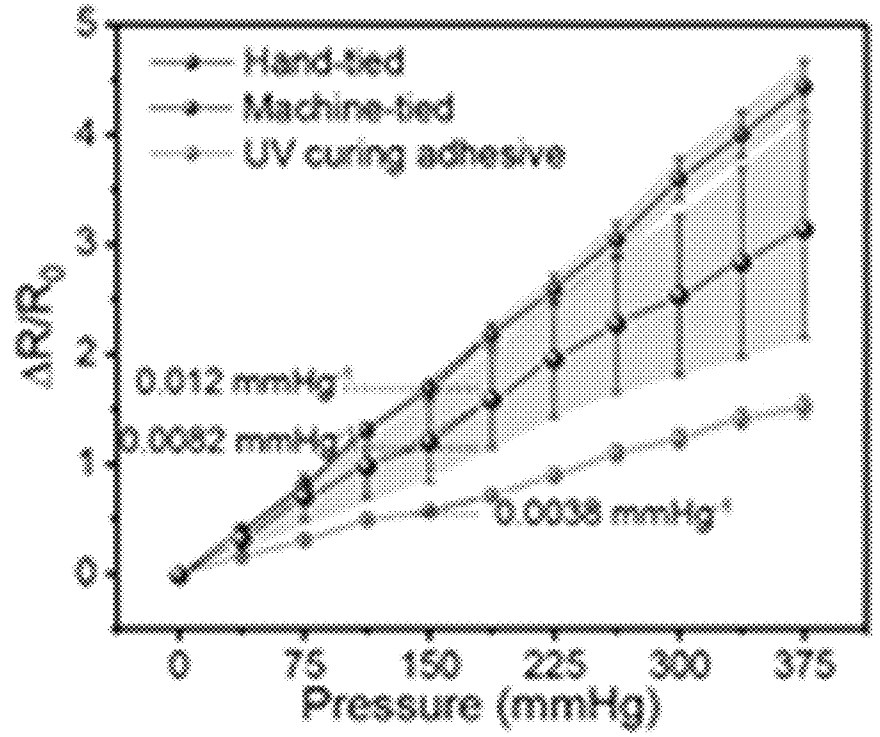
FIG. 26 is a plot illustrating a measured change in electrical resistance as a function of applied pressure for a hand-tied knot, a machine-tied knot, and a machine-tied knot with a curing adhesive applied.
Figure 27:
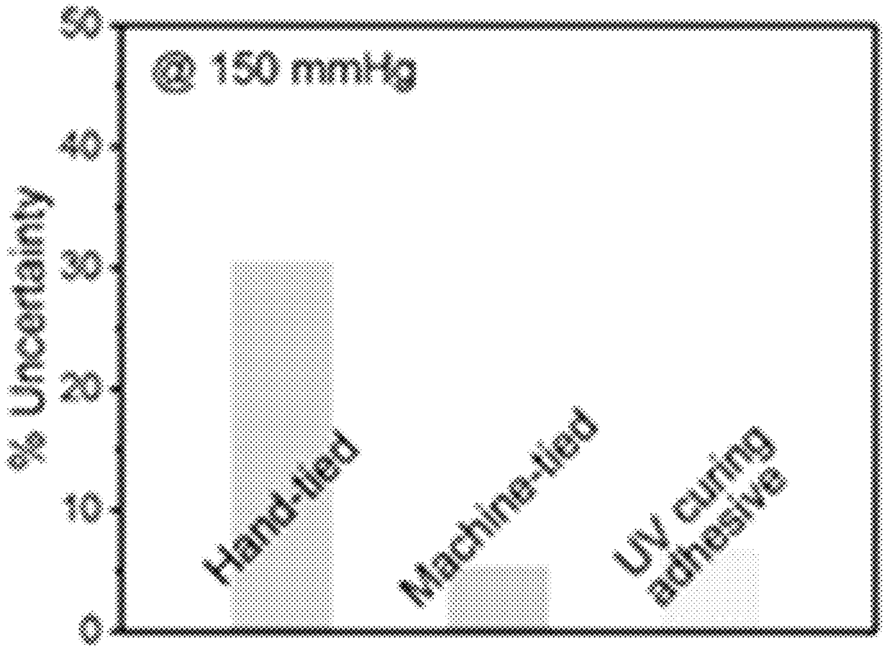
FIG. 27 is a plot illustrating percentage uncertainty of the measured change in electrical resistance of the knots of FIG. 26.
Figure 28:
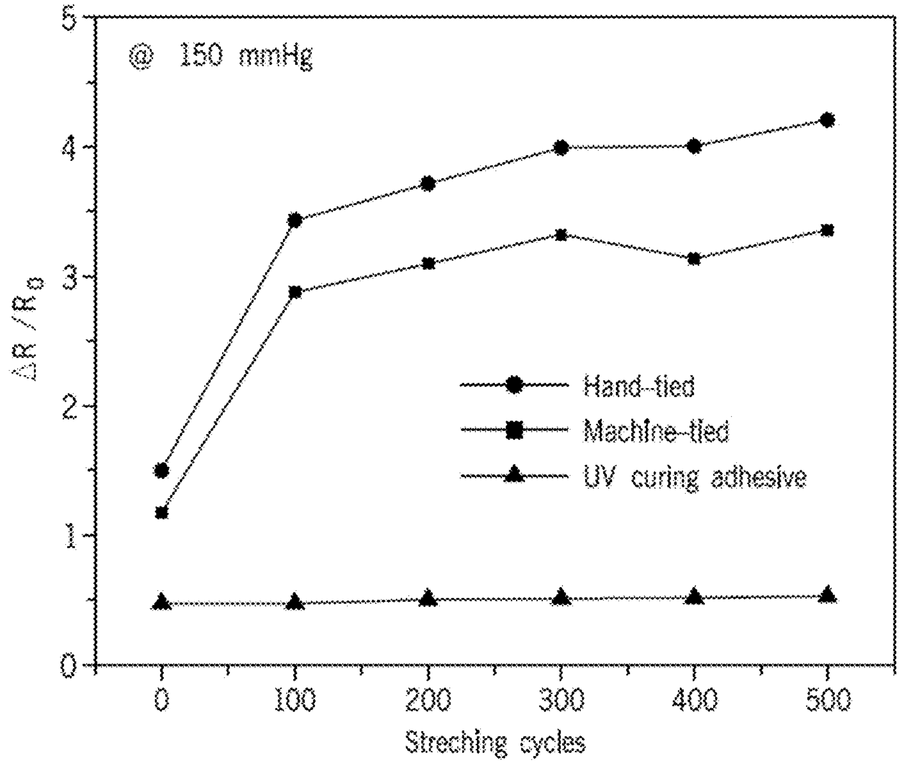
FIG. 28 is a plot illustrating a measured change in electrical resistance for an applied pressure of approximately 150 mmHg for the knots of FIG. 26, as a function of a number of stretching cycles at 50-percent tensile strain.

As a result, we observed a drop in percentage uncertainty of approximately 5 times at 150 mmHg applied pressure, after the machine and/or UV curing adhesive treatment (see FIG. 27, showing percentage uncertainty of the three knot samples reported in FIG. 26 at 150 mmHg pressure). In particular, machine-tied samples (6.1-percent) had approximately 5 times lower percentage uncertainty than hand-tied samples (31.6-percent). Through a cyclic stretching test, we verified that although UV curing adhesive treatment reduced the initial sensitivity by half, it successfully preserved the value upon five hundred stretching cycles with 50-percent tensile strain, a significant improvement compared to the untreated ones (see FIG. 28, showing $\Delta R/R_0$ of hand-tied, machine-tied, and machine-tied with UV curing adhesive samples at 150 mmHg pressure as a function of stretching cycle with 50-percent tensile strain). In particular, the values of hand-tied and machine-tied samples increased by approximately three times after the first one hundred cycles, whereas that of samples with UV curing adhesive remained almost constant after five hundred cycles.

Figure 29:
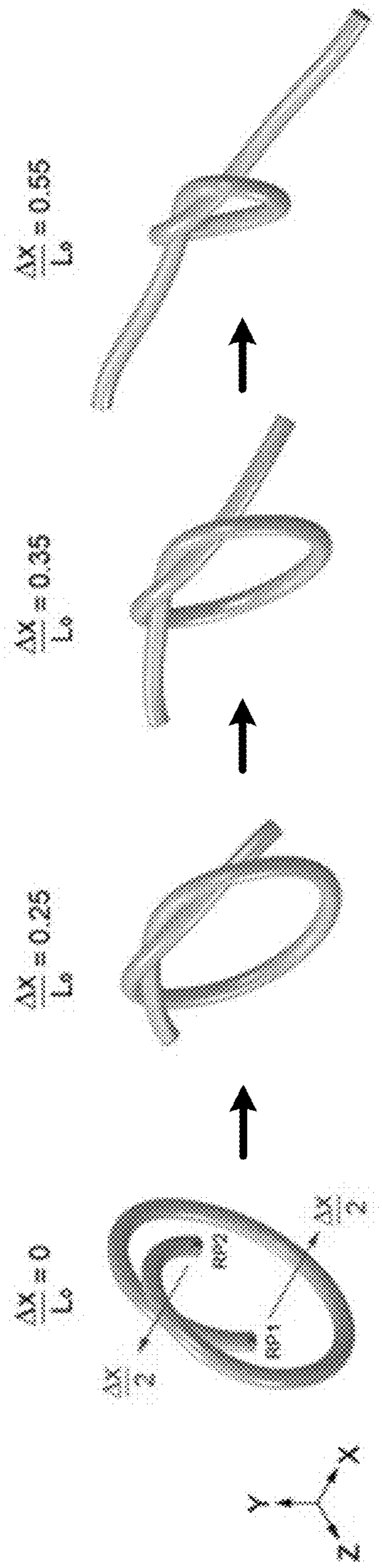
FIG. 29 is a perspective view illustrating a sequence of progressively deformed shapes formed during knot formation using a finite element simulation.
Figure 30:
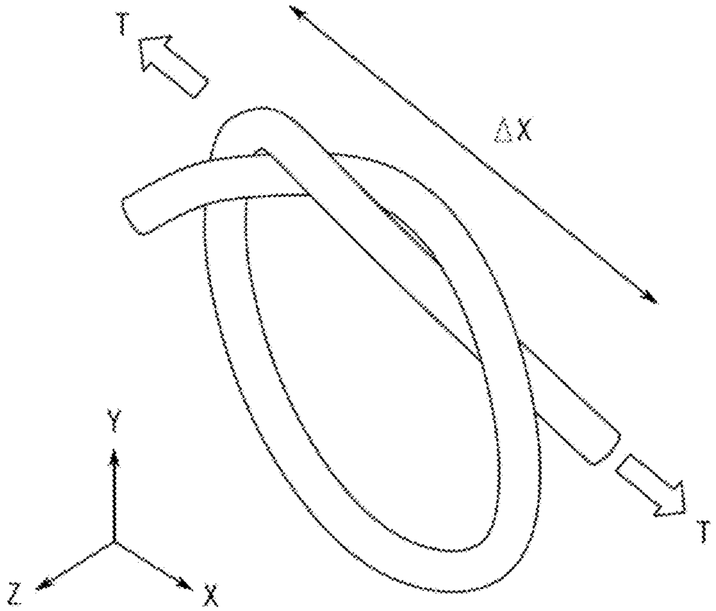
FIG. 30 is a perspective view of a finite element model of an elastic tube being knotted into an overhand knot shape via pulling the extremities of the tube.
Figure 31:
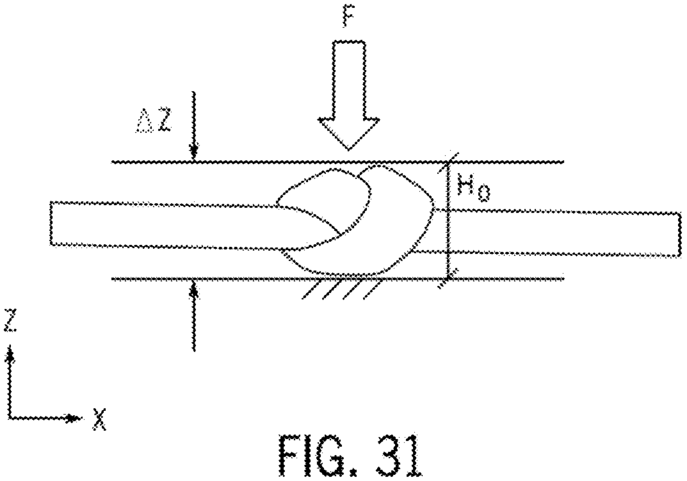
FIG. 31 is a perspective view of the finite element model of FIG. 30, being formed into an overhand knot and being compressed.

Next, we employed FE simulations to characterize the mechanical response of elastic overhand knots with different design parameters. In particular, we first developed three-dimensional (3D) FE models of an elastic tube in the loop (e.g., an overhand knot) configuration (see FIG. 29, showing the sequence of progressively deformed shape of an elastic rod used to form an overhand knot at different levels of applied normalized displacement, e.g., displacement, $\Delta x$, divided by the initial length, $L_0$, of the elastic rod, $\Delta x/L_0$, specifically 0, 0.25, 0.35, and 0.55, wherein an $\Delta x/L_0$ of 0 was the CAD model of the loop configuration used to run the knot formation simulations). Reference points $RP_1$ and $RP_2$ were the reference points located in the center of the extremities of the rod. To establish a knot configuration, the extremities of the rod were pulled via application of displacement, $\Delta x/2$, to the reference points along the ±x direction, and performed dynamic explicit analysis to evaluate the behavior of the tube by pulling the extremities to form an overhand knot (see FIG. 30). Then, the response of the knots under normal compression though application of normal displacement, $\Delta z$, was assessed by subsequent compression of knots using a rigid plate (see FIG. 31). The elastic tube assumed to have an initial outer diameter, $D_0$ of approximately 0.64 millimeters, $L_0$ or approximately 32 millimeters, to of approximately 0.17 millimeters, and an elastic modulus, $E_0$ of approximately 470 kPa (e.g., vinyl polysiloxane silicone-based rubber).

Figure 32:
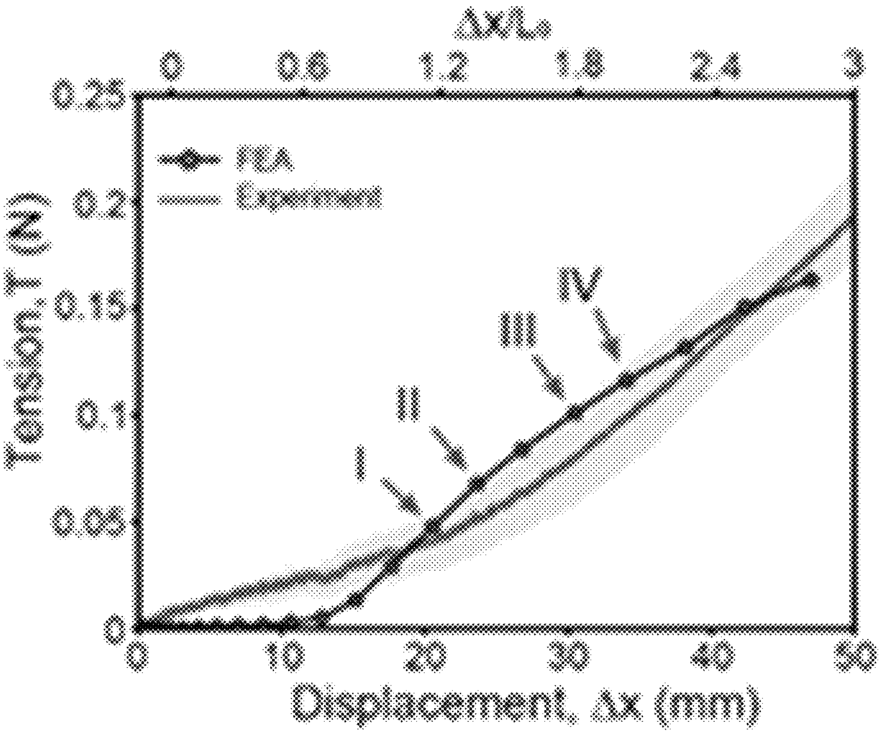
FIG. 32 is a plot illustrating the required tensile force to form an overhand knot as a function of displacement of the extremities of a tube used to form the knot.
Figure 33:
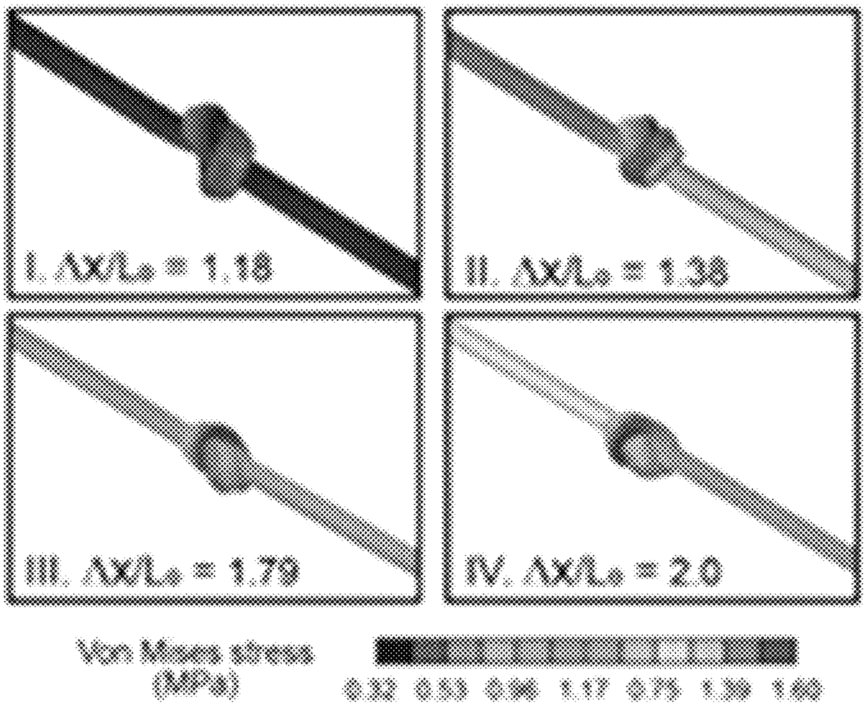
FIG. 33 is an image illustrating the stresses resulting from knot formation of the finite element model of FIG. 31, for various displacements of the extremities of the tube.

FIG. 32 illustrates the uniaxial tensile force, T, required to create an overhand knot as a function of the corresponding applied displacement between the extremities, $\Delta x$, and its normalized value, $\Delta x/L_0$, demonstrating a monotonic increase in T. To confirm the numerical predictions, we experimentally measured the force-displacement response during knot tying of silicone tubes (e.g., with $D_0$ of approximately 0.64 millimeters and $L_0$ of approximately 32 millimeters) filled with eGaIn using a tensile testing machine. The FE results were in a close agreement with the experimental data and therefore validating our FE results. Relatedly, FIG. 33 illustrates snapshots obtained from the nonlinear FE simulations of the overhand knot at different levels of $\Delta x/L_0$, specifically, (I) 1.18, (II) 1.38, (III) 1.79, and (IV) 2.0, showing that the knot became tighter with the applied tension, T, while the local stresses increased throughout the knot.

Figure 34:
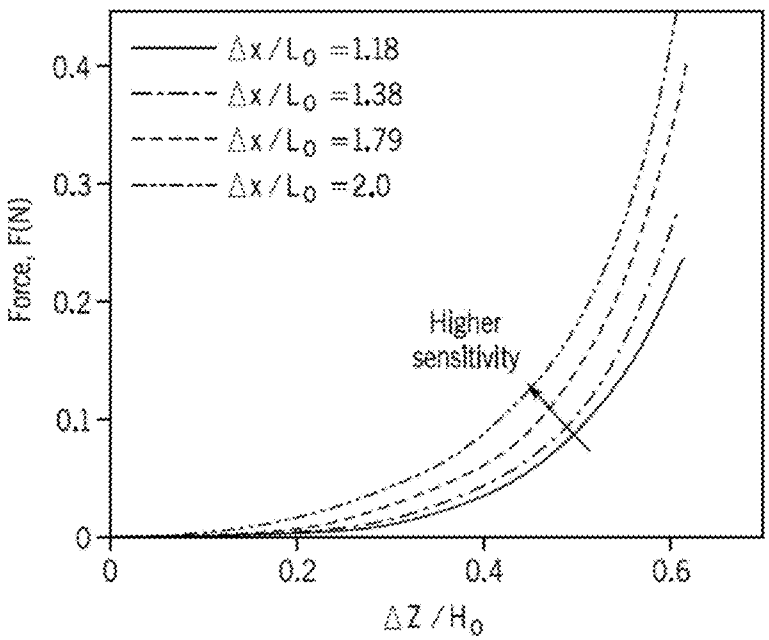
FIG. 34 is a plot illustrating a resultant normal force of the finite element model of FIG. 31 as a function of knot deformation for various levels of normalized displacement of the extremities of the tube.
Figure 35:
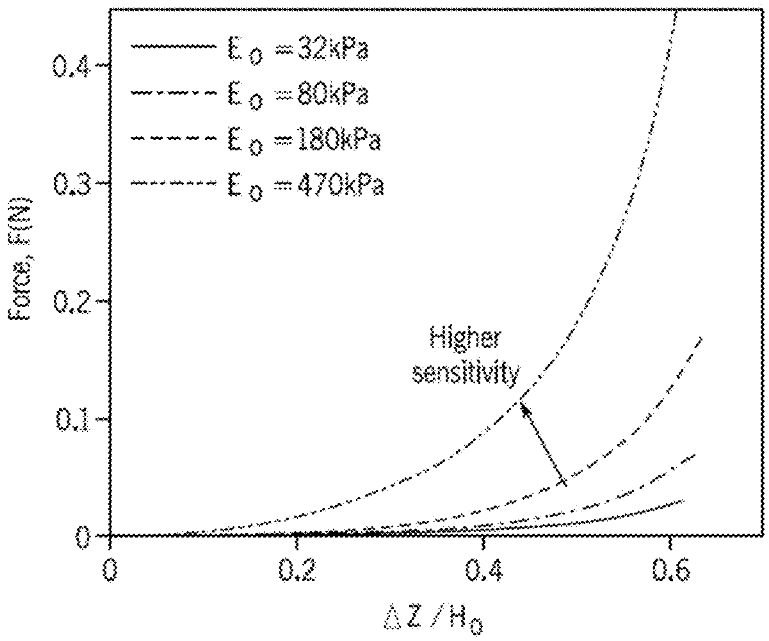
FIG. 35 is a plot illustrating a resultant normal force of the finite element model of FIG. 31 as a function of knot deformation for various tube materials with differing elastic moduli.
Figure 36:
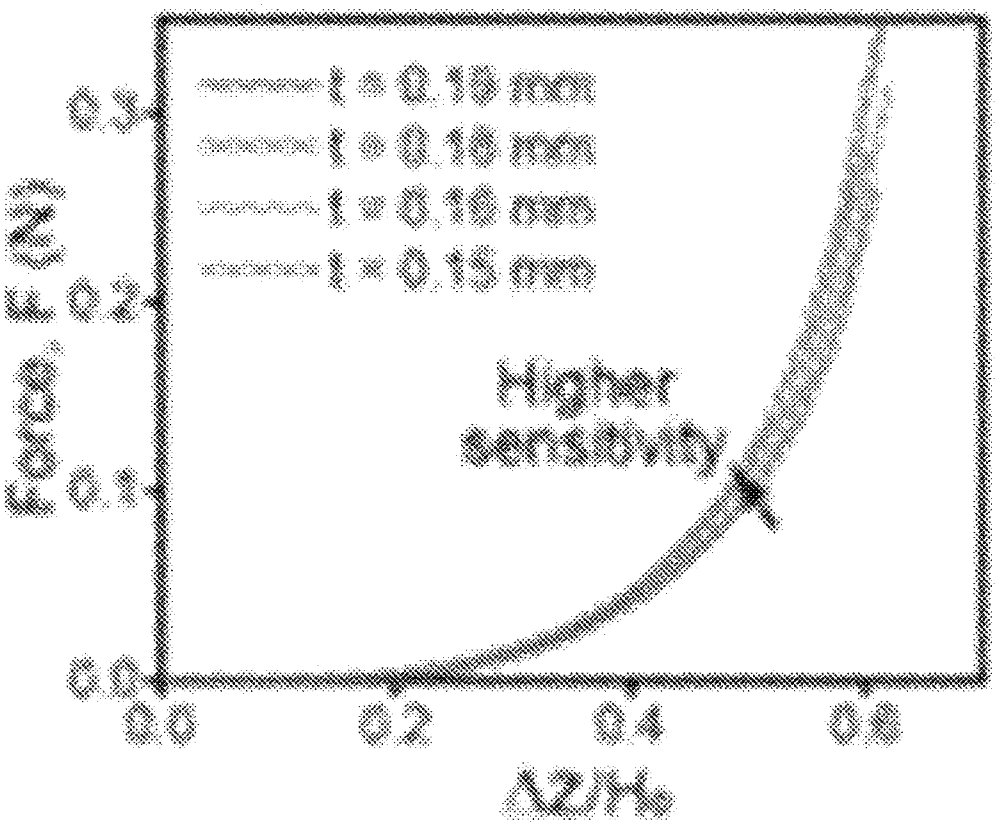
FIG. 36 is a plot illustrating a resultant normal force of the finite element model of FIG. 31 as a function of knot deformation for tubes with various wall thicknesses.

We further examined the compression behavior of knots through the application of normal displacement, $\Delta z$, and monitored the compression forces in the normal direction, F, as a function of normalized vertical displacement, $\Delta z/H_0$, where $H_0$ was the height of the undeformed knots. In particular, we numerically investigated the effects of $\Delta x/L_0$ and a range of tube parameters, including elastic modulus ($E_0$) and wall thickness ($t_0$), on F. As illustrated in FIG. 34, showing the evolution of F at different levels of the aforementioned $\Delta x/L_0$, shows that different values of F were required to deform the knots for a given applied $\Delta z/H_0$. Moreover, these results suggested that the rates of variation of F against $\Delta z/H_0$ (i.e., the slope of the curves) were higher for the tighter knots (i.e., the knots with higher $\Delta x/L_0$), a signature of enhanced pressure sensitivity of the tighter knots. Finally, we reported the evolution of F as a function of $\Delta z/H_0$ for the knots made of various elastomeric silicones with $E_0$ of 32 kPa, 80 kPa, 180 kPa, and 470 kPa (see FIG. 35), and to of 0.15 millimeters, 0.16 millimeters, 0.18 millimeters, and 0.19 millimeters (see FIG. 36), formed by applying $\Delta x/L_0$ of 1.75. The results demonstrated a considerable larger F corresponding to higher pressure sensitivity for the knots made of stiffer tubes (i.e., with higher $E_0$), while the effect of to on F and pressure sensitivity remained almost unchanged for the range examined. Together, these results showcase the ability to quantitatively optimize the knot configurations that allowed for enhanced pressure sensitivity and customizations to meet specific application needs.

Strategies for Multiplexed Measurements

Figure 37:
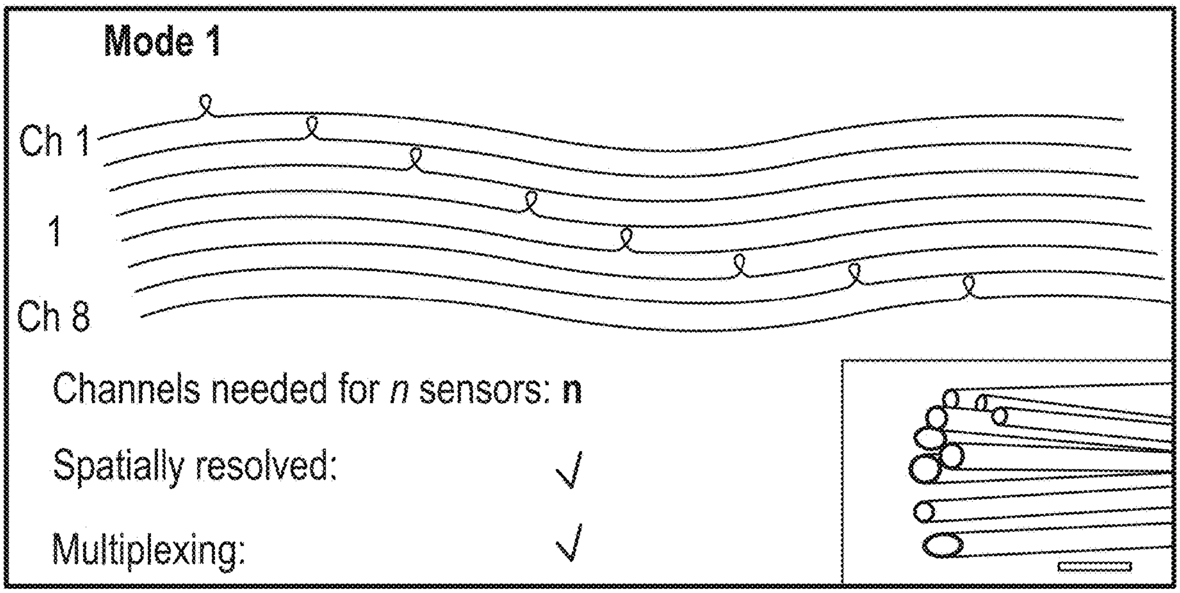
FIG. 37 is a schematic view illustrating a first mode of multiplexing, according to aspects of the disclosure.

We next investigated strategies for multiplexed measurements using the SPS, which were important for assessing mechanical activities along the length of the GI segment being evaluated, up to 80 centimeters, and in some cases, up to 100 centimeters. Due to the high degree of sensor reconfigurability, three modes of multiplexing can be devised, each with different levels of fabrication challenges, total numbers of channels, and functions that can be tailored for targeted application needs. Mode 1 was the most common approach where each knot occupied one channel (see FIG. 37), similar to conventional manometry. This mode allowed for maximum spatial resolution, which was suitable for identifying pathological esophageal or antroduodenal motility, or coordinated movements that demanded simultaneous measurements at distinct GI locations, but at the expense of being fabrication-heavy, bulky, and expensive on the recording hardware.

Figure 38:
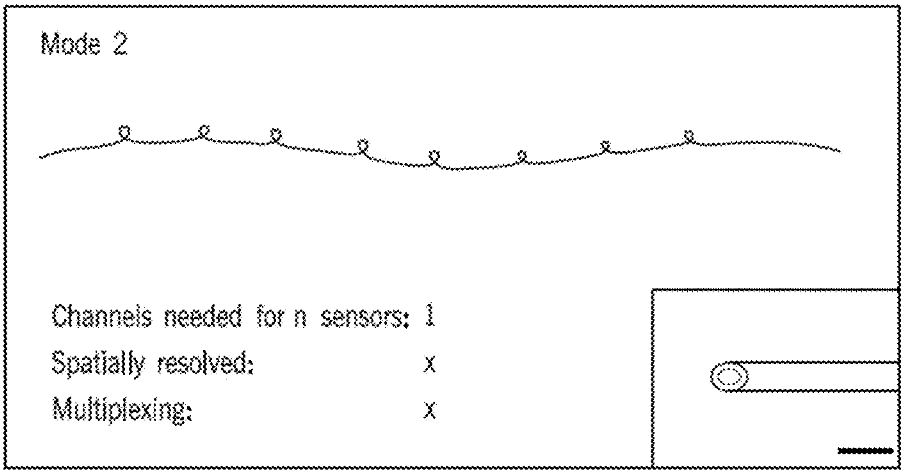
FIG. 38 is a schematic view illustrating a second mode of multiplexing, according to aspects of the disclosure.

Mode 2 was the most economical in terms of device fabrication and data recording, where multiple knots were tied onto a single tubing (see FIG. 38) that required only one multimeter as the recording hardware. Although mode 2 cannot spatially resolve the signals if they occurred simultaneously, this mode may still be useful in some cases such as evaluating the multiple rapid swallow responses where the pressure triggering of each knot along the path was known to occur sequentially and directionally. In this case, a second channel would be placed at the upper esophageal sphincter (UES) for simultaneous monitoring of the UES contraction/relaxation. It may also be possible to realize spatially resolved monitoring in mode 2 through a time-domain reflectometry approach, although the resulting increase in complexity and cost of the recording hardware may deter its use in resource-limited environments.

Figure 39:
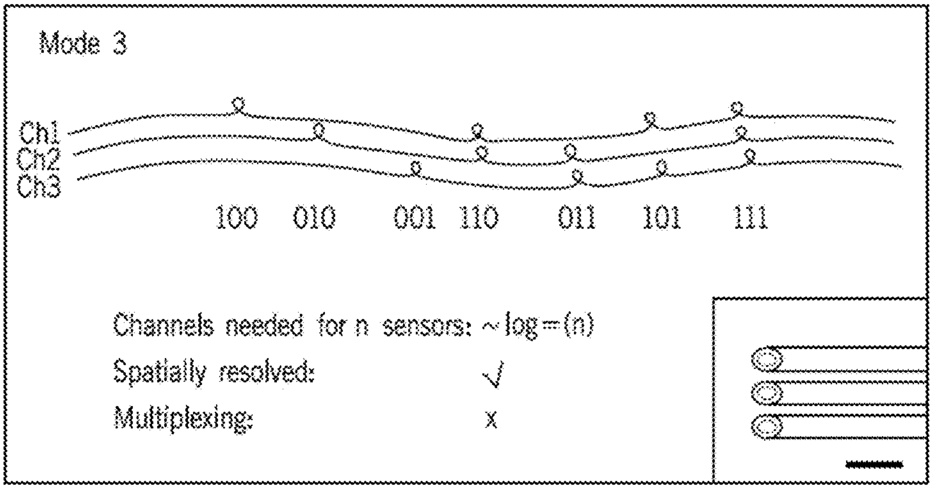
FIG. 39 is a schematic view illustrating a third mode of multiplexing, according to aspects of the disclosure.
Figure 40:
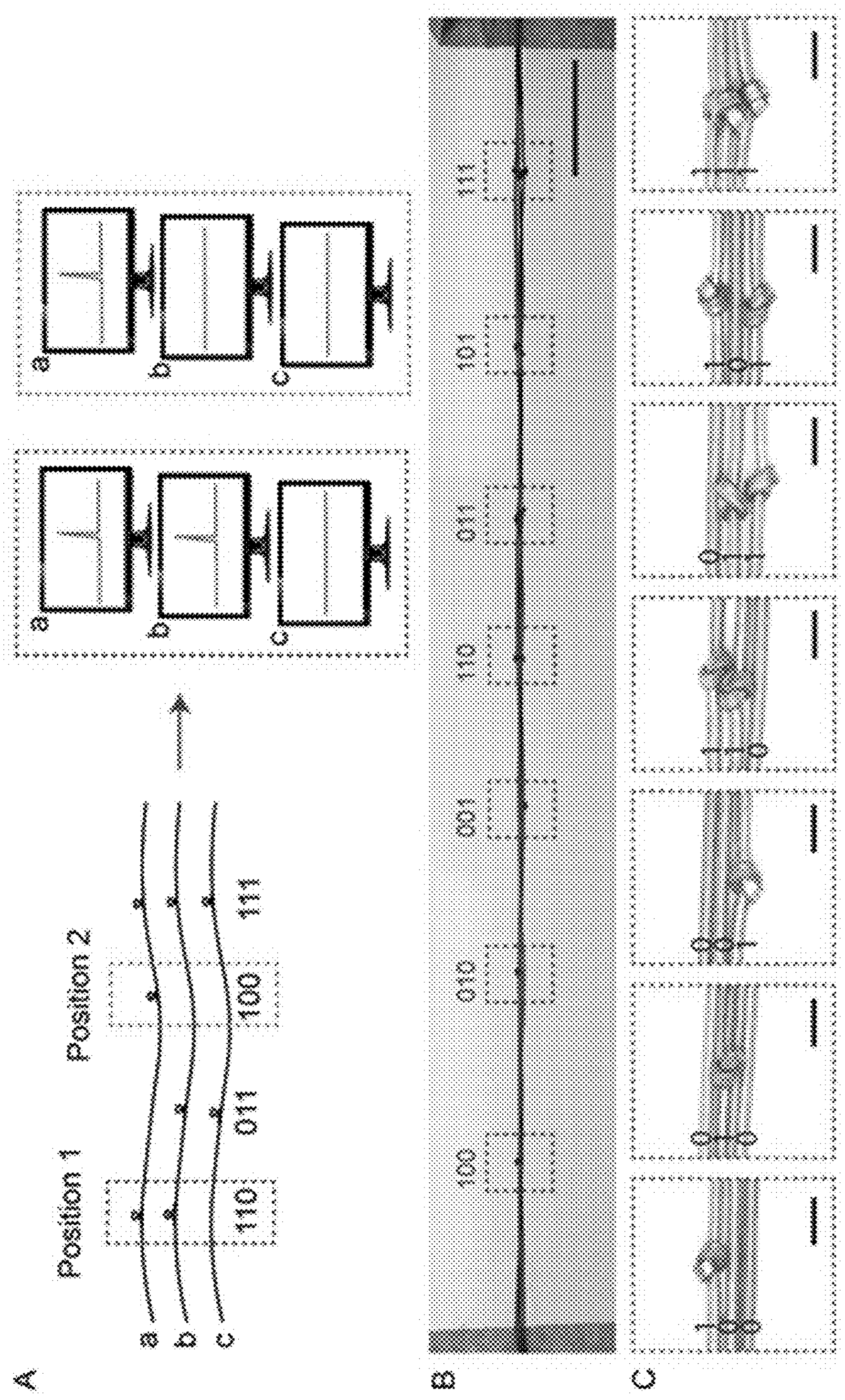
FIG. 40 is a schematic view illustrating how the third mode of multiplexing of FIG. 39 can be used similar to a binary number system.

Finally, mode 3 exploited different combinations of knots at a given spot inspired by the binary number system (FIGS. 39 and 40). In this case, n channels can resolve up to $2^n$-1 sensory knots, and temporally overlapping pressure responses may be resolved by de-coupling the linear combinations of the resulting signals if the amplitude and frequency of each signal were known to be similar. For example, if a first channel showed a signal that overlapped with a signal on one or both of a second channel and a third channel, but with an amplitude that is approximately twice that of those on the second or third channel, it can be implied that two separate pressure-inducing events occurred along the SPS. Accordingly, the individual signals from each of the channels may be resolved according to a binary algorithm and the pressure at each position along the SPS can be determined. This mode may find utility in haptic or keyboard sensing where the amplitude and frequency of each load were similar.

Figure 41:
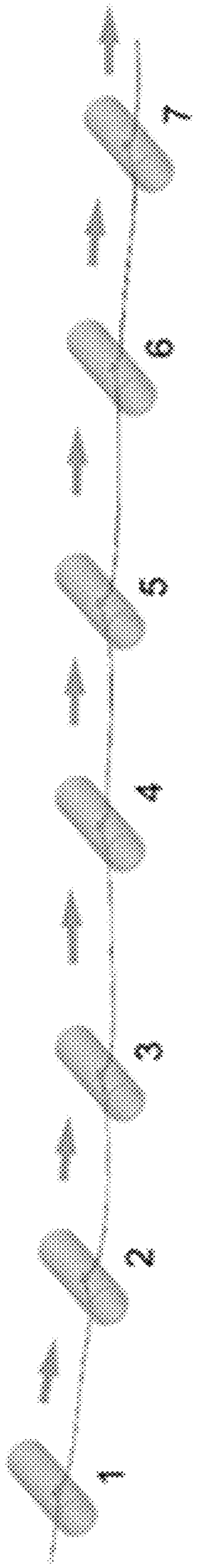
FIG. 41 schematic view illustrating a rolling test, wherein restrictions of an SPS are compressed in linear sequence.
Figure 42:
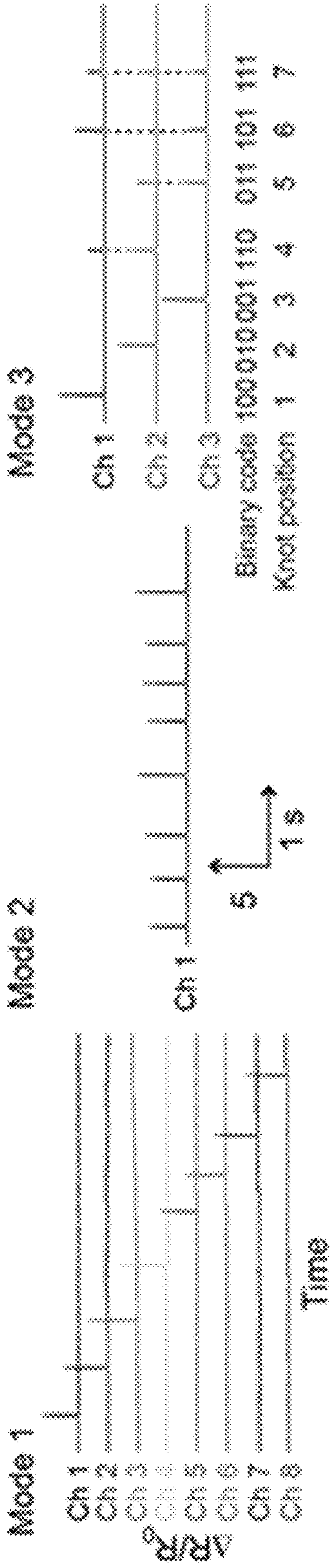
FIG. 42 is a series of plots showing a measured change in resistance for each of the multiplexing modes of FIGS. 37-40, as measured using the rolling test of FIG. 41.

We designed two in vitro tests to validate the three modes of multiplexing, wherein the SPS, containing eight (modes 1 and 2) or seven (mode 3) sensory knots, with approximately 5 centimeters spacing between knots was placed inside a small intestine simulator (approximately 40 centimeters long and approximately 1.5 centimeters in inner diameter) made of ultra-soft silicone rubber. The first test involved rolling a solid cylinder (approximately 100 grams) from one end of the simulator to the other, mimicking the in vivo esophageal swallowing under healthy conditions (see FIG. 41). In all three modes, as illustrated in FIG. 42, the passage of the cylinder through each sensory node was registered as a spike in the multi-channel resistance recorder. In mode 3 the total pressure at a given spatial coordinate can be reasonably estimated by summing the resistive changes ($\Delta R/R_0$) across all channels with overlapping temporal coordinates.

Figure 43:
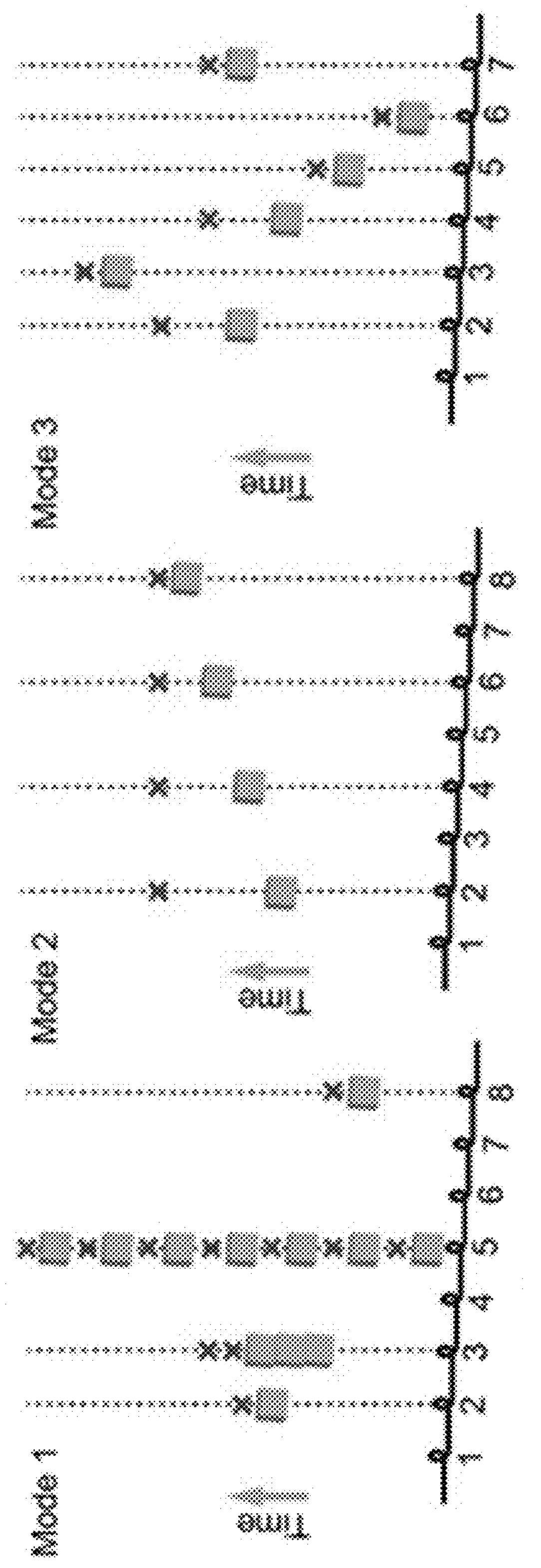
FIG. 43 is a schematic view of a random drop test for each of the multiplexing modes of FIGS. 37-40.
Figure 44:
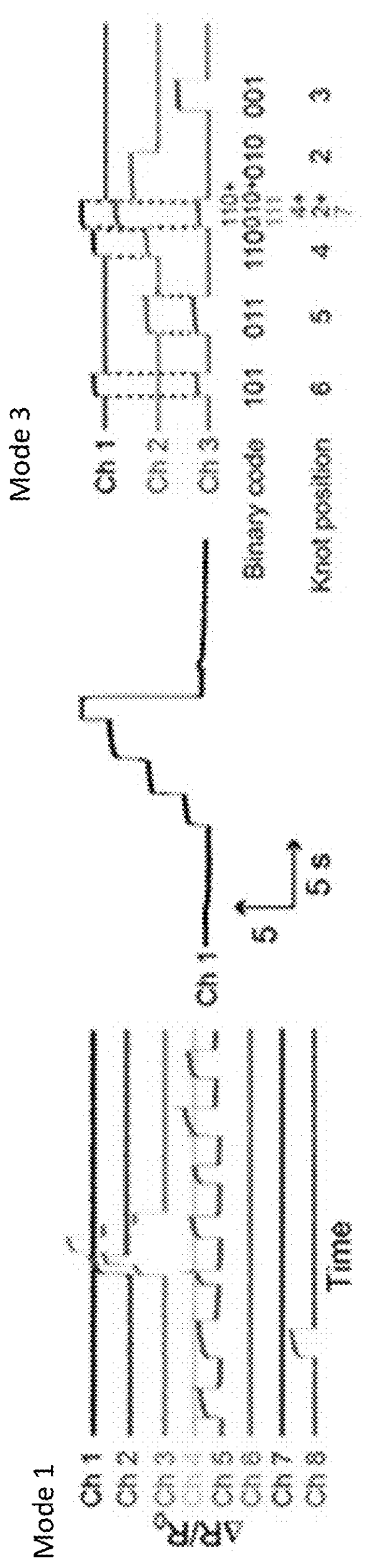
FIG. 44 is a series of plots showing a measured change in resistance for each of the multiplexing modes of FIGS. 37-40, as measured using the random drop test of FIG. 43.

The second test involved dropping weights (approximately 100 grams) at random knot positions along the simulator (see FIG. 43), mimicking the spatially random high-pressure events that may indicate GI motility disorders. As illustrated in FIG. 44, evaluating through mode 2 was unable to resolve spatial information, whereas pressure recording at a given time was the sum of all weights accumulated on the sensor. Mode 1 showed the comprehensive spectrum by displaying both magnitude and position information for each sensory node at any given time. The total pressure (or number of weights in this case) at a given knot position in mode 3 can be estimated by summing the resistive changes ($\Delta R/R_0$) across all channels with overlapping temporal coordinates.

In both the rolling and random drop tests, the knot positions deduced from the measurements in mode 3 using the binary algorithm agreed well with the actual experiments (see FIGS. 42 and 44), demonstrating its potential for spatially resolved measurements with reduced total number of channels. The signal-to-noise ratios in all cases were more than 10, which were adequate for evaluating real GI motility.

In Vivo Demonstration of Gastrointestinal Manometry

Figure 45:
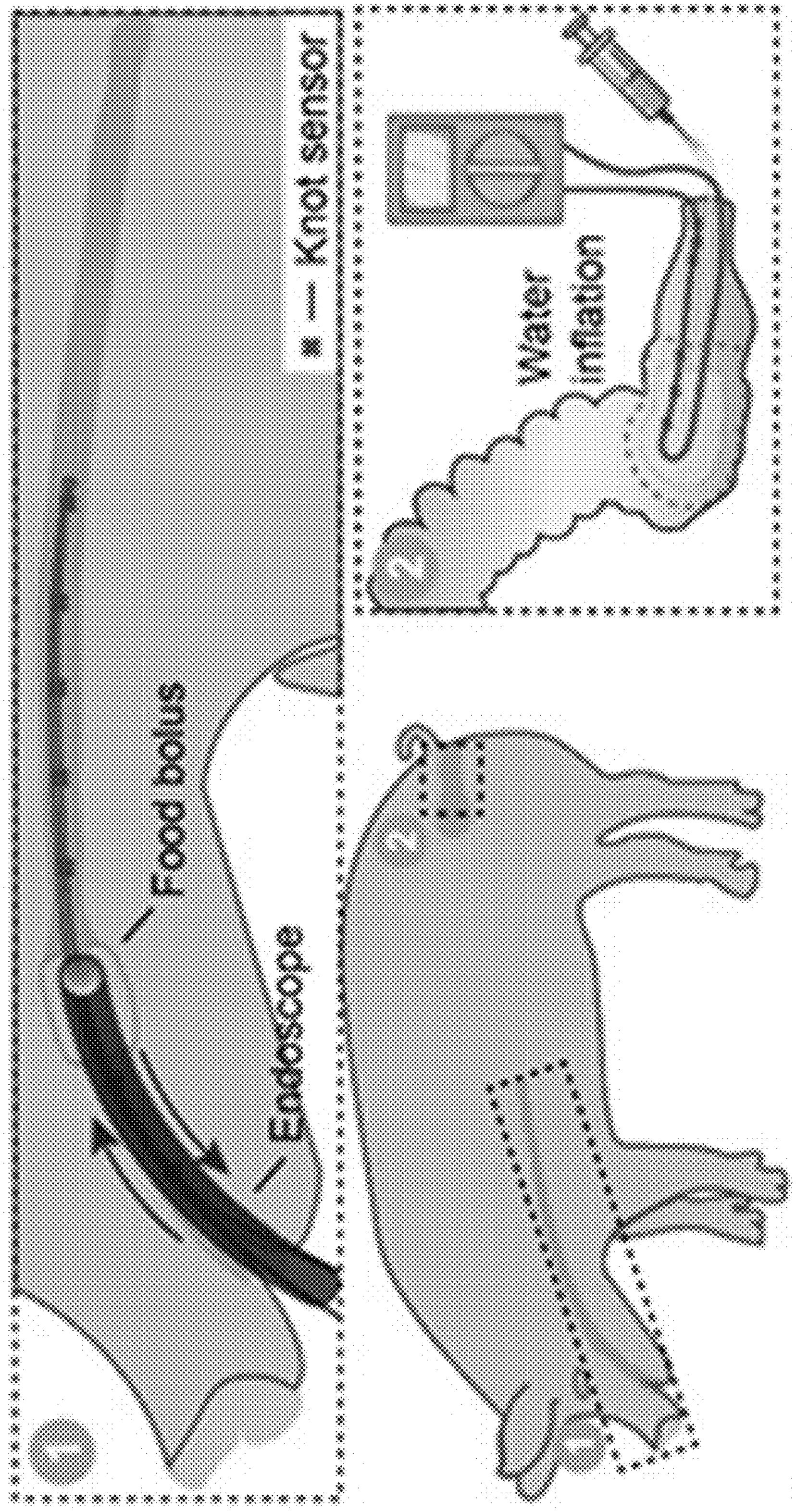
FIG. 45 is a schematic view of two studies evaluating each of the esophageal pressure during the passage of artificial food bolus attached to the tip of an endoscope, and the rectoanal pressure during rectoanal inhibitory reflex (RAIR) using a porcine model.

We further validated the utility of the SPS using a porcine model (Yorkshire swine, approximately 40 kilograms to 80 kilograms in weight) due to its anatomical similarity as humans. Specifically, the esophagus and rectum were chosen to evaluate the system by measuring the esophageal pressure during the passage of artificial food bolus and the rectoanal pressure during the rectoanal inhibitory reflex (RAIR), respectively (see FIG. 45).

Figure 46:
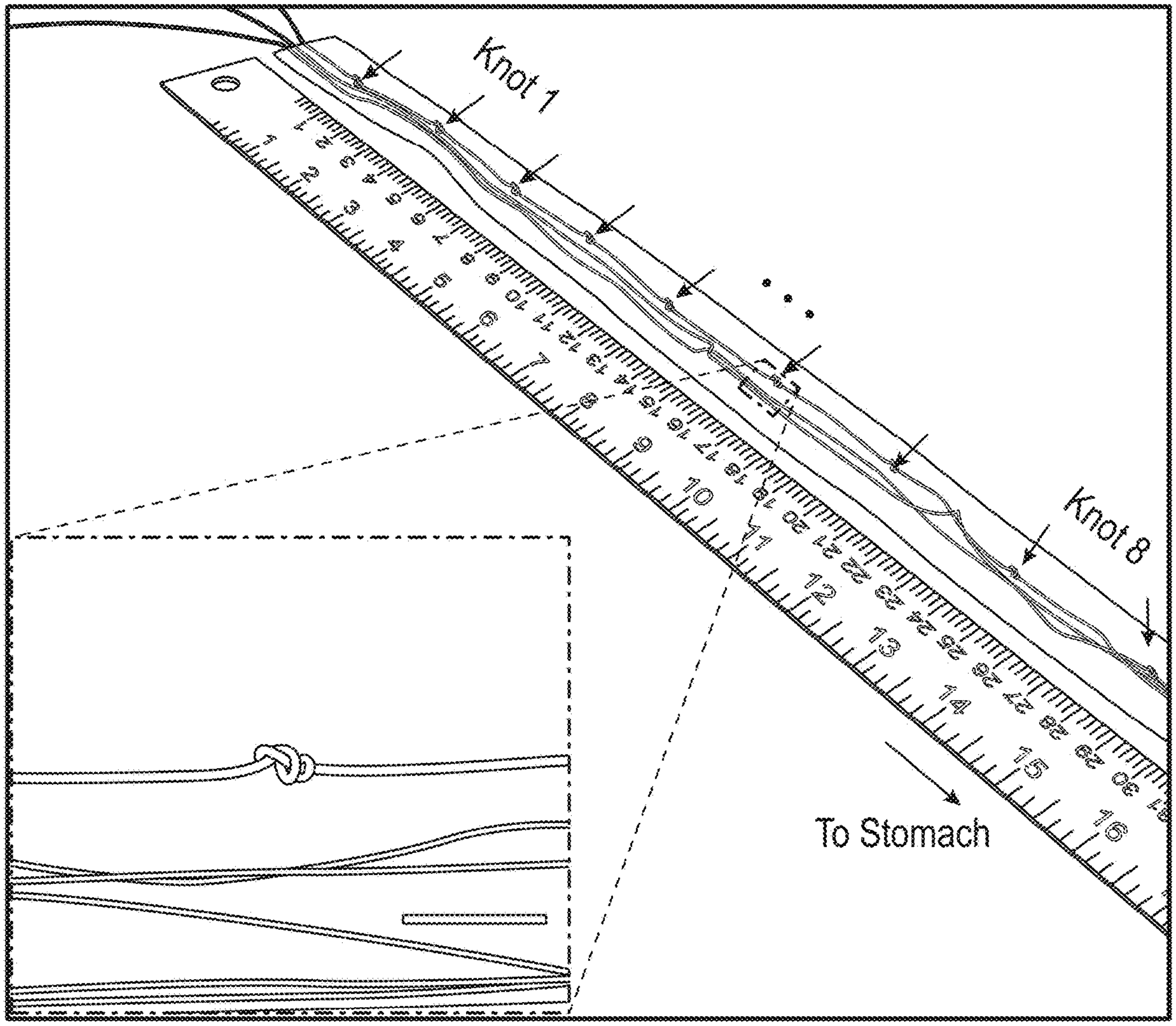
FIG. 46 is an image of a ribbon-like manometry device (SPS) containing eight knots for use in the esophageal pressure evaluation of FIG. 45.

In the first study, we designed a multi-channel, ribbon-shaped manometry device (see FIG. 46) for recording esophageal motility. Spatial information will likely be crucial in the diagnosis of an esophageal motility disorder, as dysmotility may present in the form of absent contraction, spastic or premature contractions, or simultaneous pressurization. In addition, a high-pressure junction exists at the UES approximately 10 centimeters from the oral cavity, which holds important diagnostic values for skeletal muscle disorders, head and neck radiation, stroke, and neurodegenerative diseases such as Parkinson's disease. As such, sensing mode 1 (see FIG. 37) was selected here for maximum spatial resolution, where eight knots were assembled using an approximately 45 centimeter long, soft and flexible medical grade soft silicone gel tape as the substrate, and an approximately 13 micrometer thick, low-density polyethylene film as the encapsulation (see FIG. 46). An approximately 5 centimeter spacing between each knot was chosen to match the sensor spacing of conventional manometry catheters.

Figure 47:
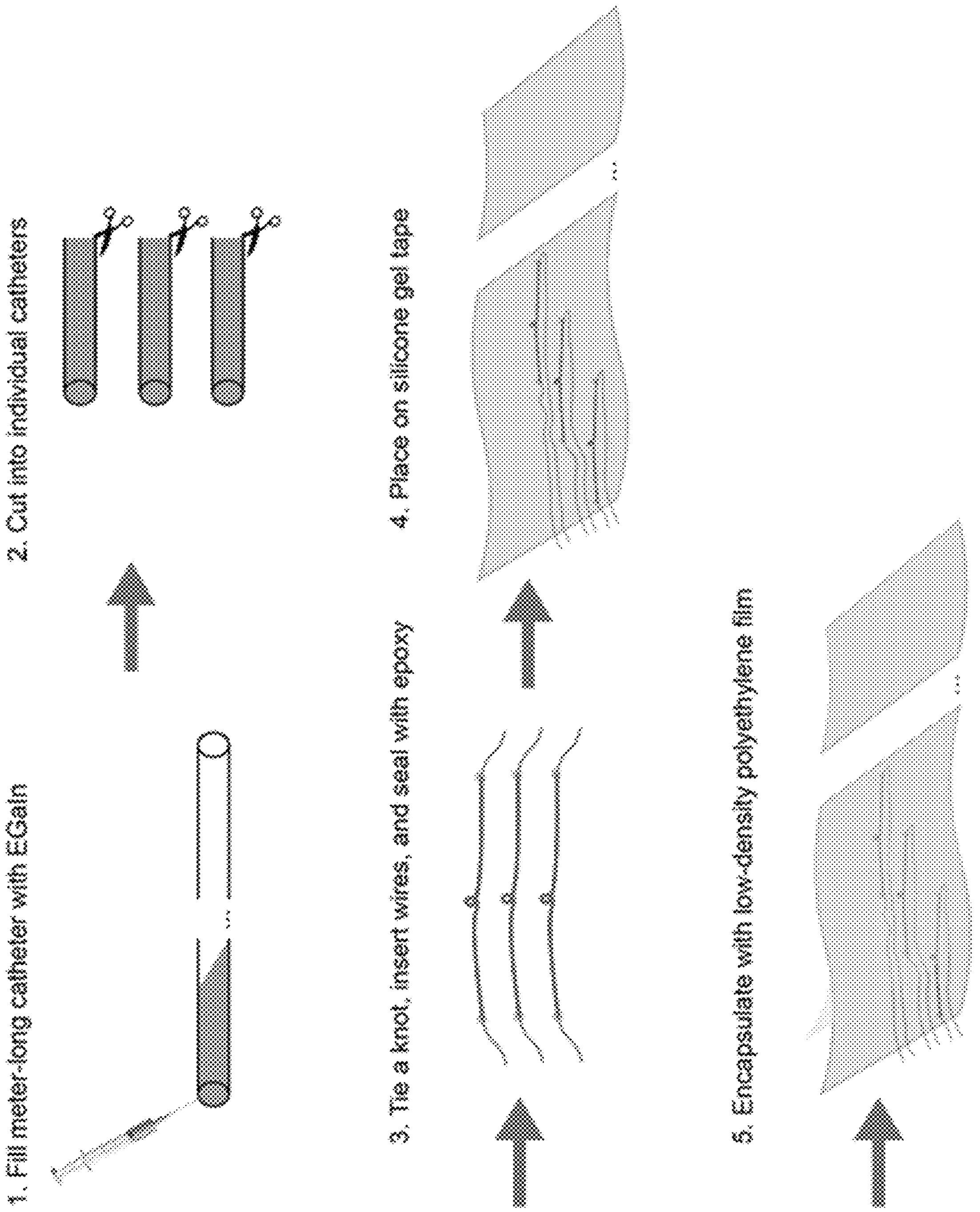
FIG. 47 is a schematic view of a method used to fabricate the ribbon-like manometry device of FIG. 46.

Detailed fabrication procedures for the device are illustrated in FIG. 47. In particular, a long silicone tubing was first filled with eGaIn, followed by cutting into short segments. A knot was tied onto each segment using mechanical stretcher, connected with copper wires at both ends and sealed using UV curing optical adhesive. The step was repeated multiple times and the resulting segments were placed and adhered onto a medical grade silicone gel tape with designated spacing between adjacent knots. An approximately 13 micrometer thick low-density polyethylene film was used to encapsulate the top surface, which completed the fabrication process. Additionally, a battery-powered, wireless, multi-channel resistance analyzing circuit was used to allow for low-cost, portable (e.g., weighing less than approximately 60 grams), and real-time recording and display of the data onto an Android mobile application with a sampling rate of 14 Hertz for up to eight channels, suitable for uses in resource-limited settings (e.g., at home or outdoor).

Figure 48:
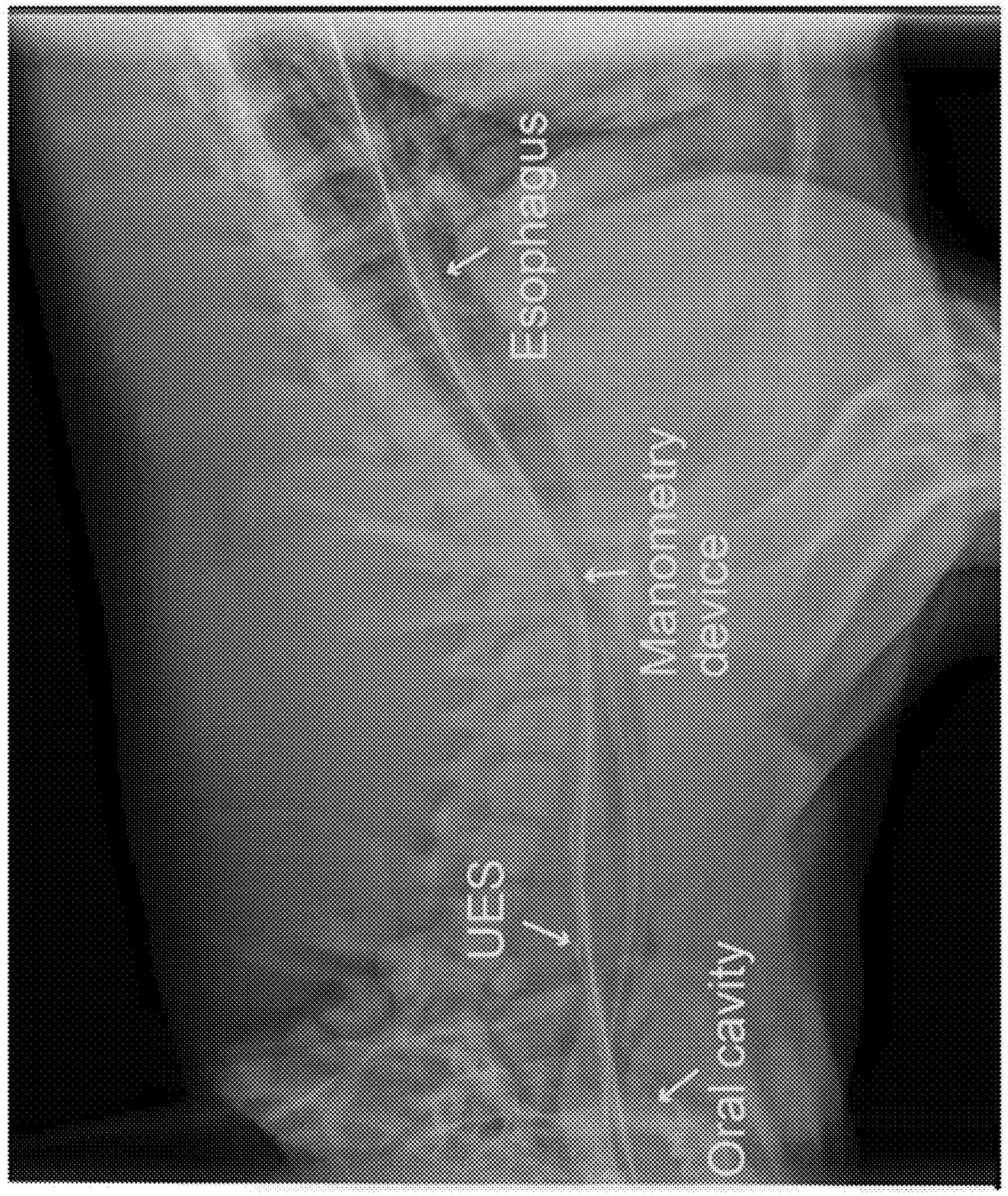
FIG. 48 is an image of the ribbon-like manometry device of FIG. 46 placed in the esophagus of the porcine model of FIG. 45 for measurement of esophageal pressure.

During the procedure, the device was wrapped onto a thin, stiff supporting tube (e.g. temperature probe or polyurethane feeding tube, approximately 3 millimeters in diameter) and inserted via the oral route into the esophagus, until the channel closest to the oral cavity displayed a jump in pressure, indicating the correct positioning of the first sensor at the UES; x-ray imaging (see FIG. 48) confirmed the proper device deployment.

Figure 49:
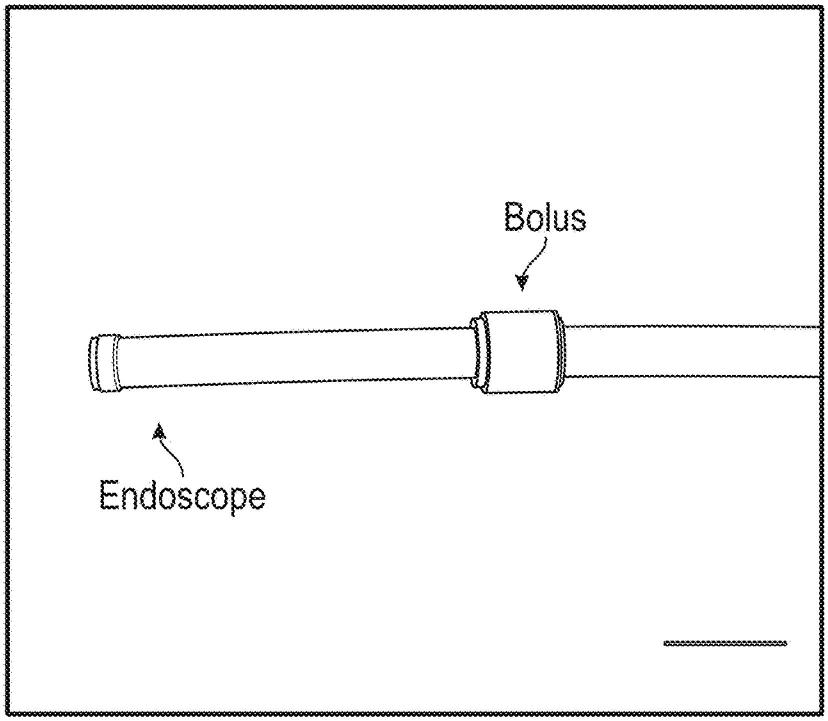
FIG. 49 is an image of an artificial bolus for insertion into the esophagus of the porcine model of FIG. 45.

The porcine swallowing reflex was significantly depressed under anesthesia, so we simulated food swallowing by attaching approximately 5 milliliters of artificial food bolus made from mixtures of alginate and gelatin solutions onto the tip of the endoscope (see FIG. 49, scale bars of approximately 2 millimeters) and sliding it through the esophagus. The bolus was unlikely to alter or damage the knots during sliding due to its smooth, edgeless surface finish. In particular, the protocol for making artificial food boluses was adapted from Miyu Hosotsubo et al., *Fabrication of artificial food bolus for evaluation of swallowing*, Public Library of Science ONE (Dec. 15, 2016), doi: 10.1371/journal.pone.0168378. Specifically, a three-percent by weight solution of sodium alginate (Sigma-Aldrich, CAS 9005-38-3, medium viscosity grade) was mixed with a 5-percent by weight solution of gelatin (Sigma-Aldrich, CAS #9000-70-8, gel strength of approximately 300 gram Bloom, Type A) at a 7:3 weight-to-weight ratio and solidified at room temperature over 12 hours. The resulting gel was subsequently immersed in a twenty-percent by weight calcium dichloride ($CaCl_2$)) solution with a volume equivalent to that of the alginate solution for twenty-four hours before use.

Figure 50:
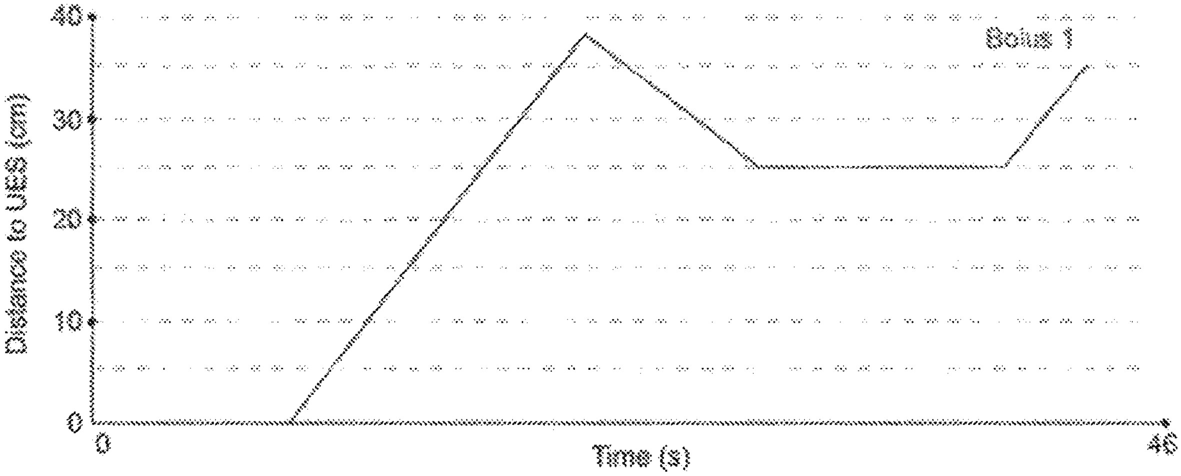
FIG. 50 is a plot of an insertion distance of the artificial bolus of FIG. 49 to the esophagus of the porcine model of FIG. 45 as a function of time.
Figure 51:
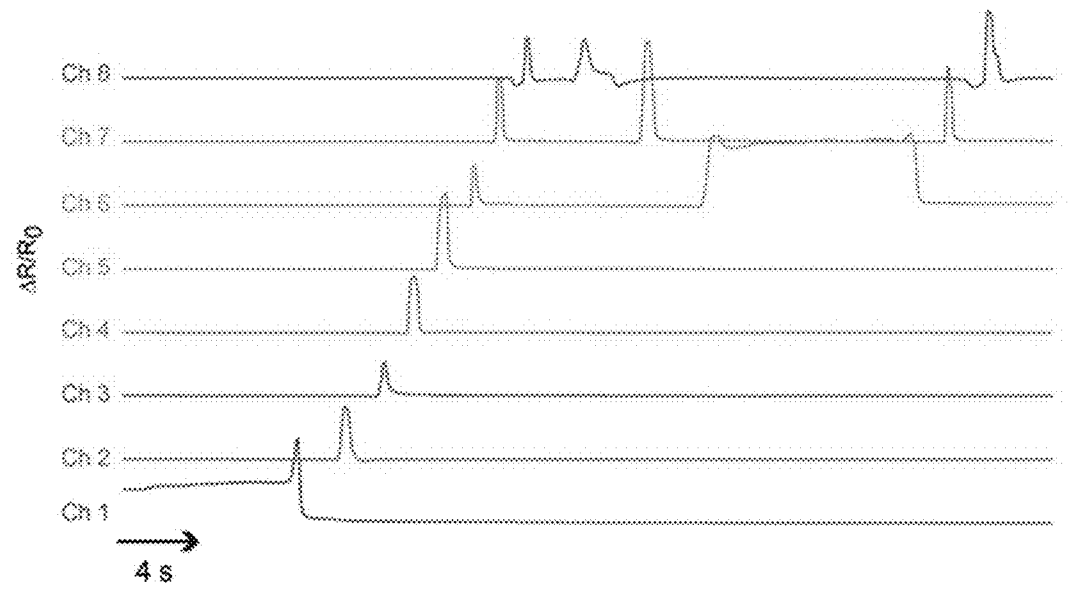
FIG. 51 is a plot of a multi-channel pressure recording of the manometry device of FIG. 46 during movement of the artificial bolus of FIG. 49 according to FIG. 50.
Figure 52:
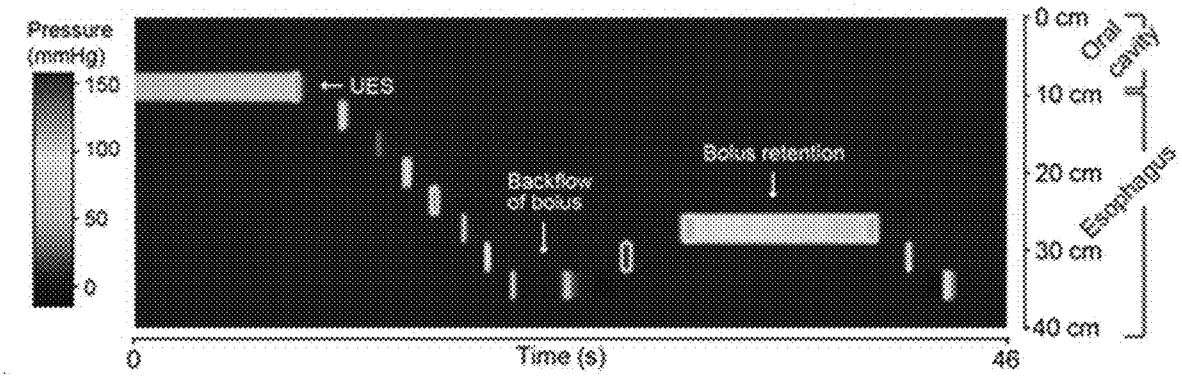
FIG. 52 is another plot of the multi-channel pressure recording of the manometry device of FIG. 46 during movement of the artificial bolus of FIG. 49 according to FIG. 50, illustrating the location of the measured pressures.

In the first experiment, we slightly retracted and held the bolus after reaching the end of the manometry device to simulate the backflow and retention of bolus, respectively, which may be found in esophageal motility disorders (see FIG. 50). The multi-channel pressure recording (see FIG. 51) was converted into a pressure color plot in adherence to the modern data representations for HRM (see FIG. 52), where both events corresponding to the backflow and retention of bolus were clearly registered and displayed.

Figure 53:
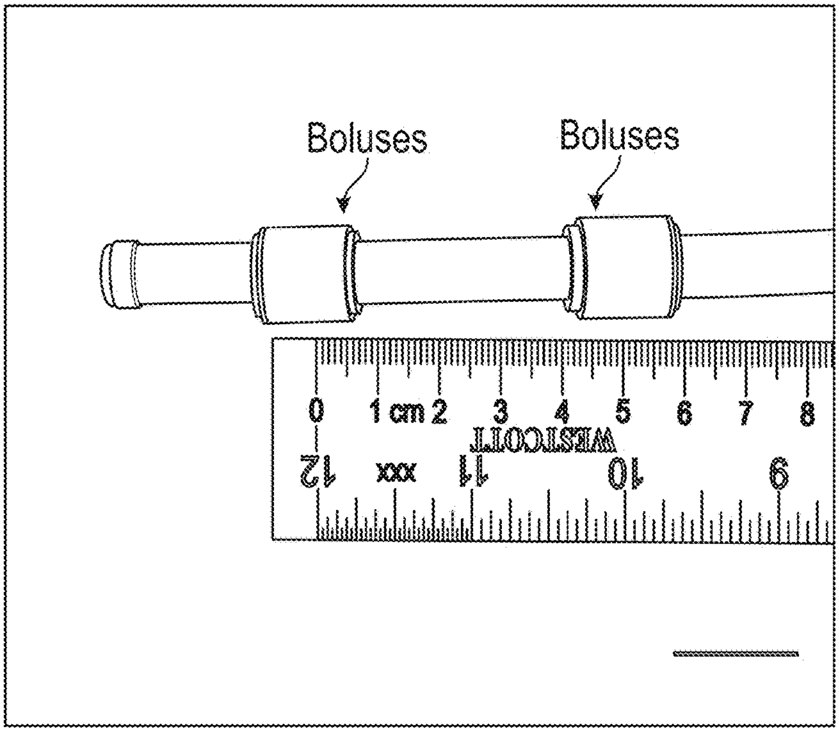
FIG. 53 is an image of another artificial bolus for insertion into the esophagus of the porcine model of FIG. 45.
Figure 54:
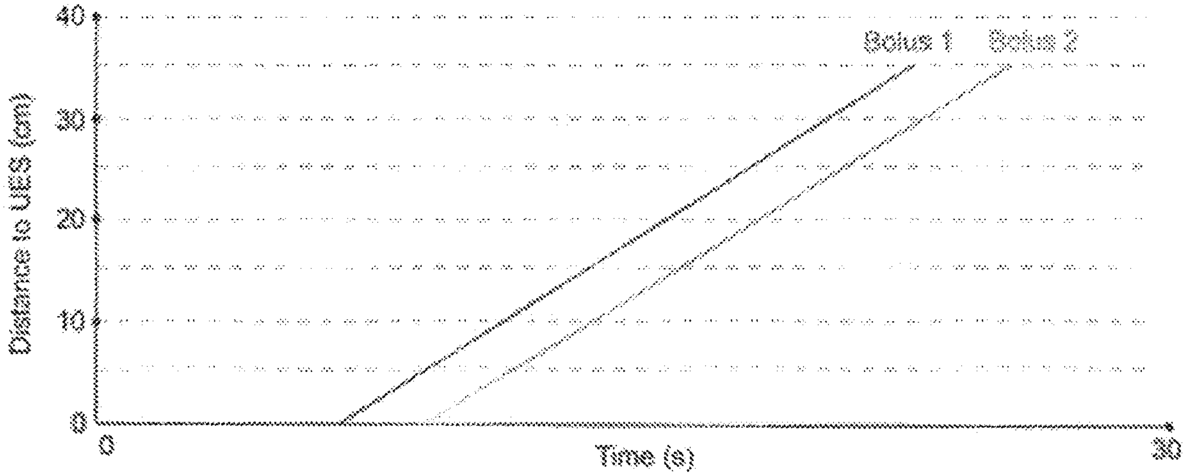
FIG. 54 is a plot of an insertion distance of the artificial bolus of FIG. 53 to the esophagus of the porcine model of FIG. 45 as a function of time.
Figure 55:
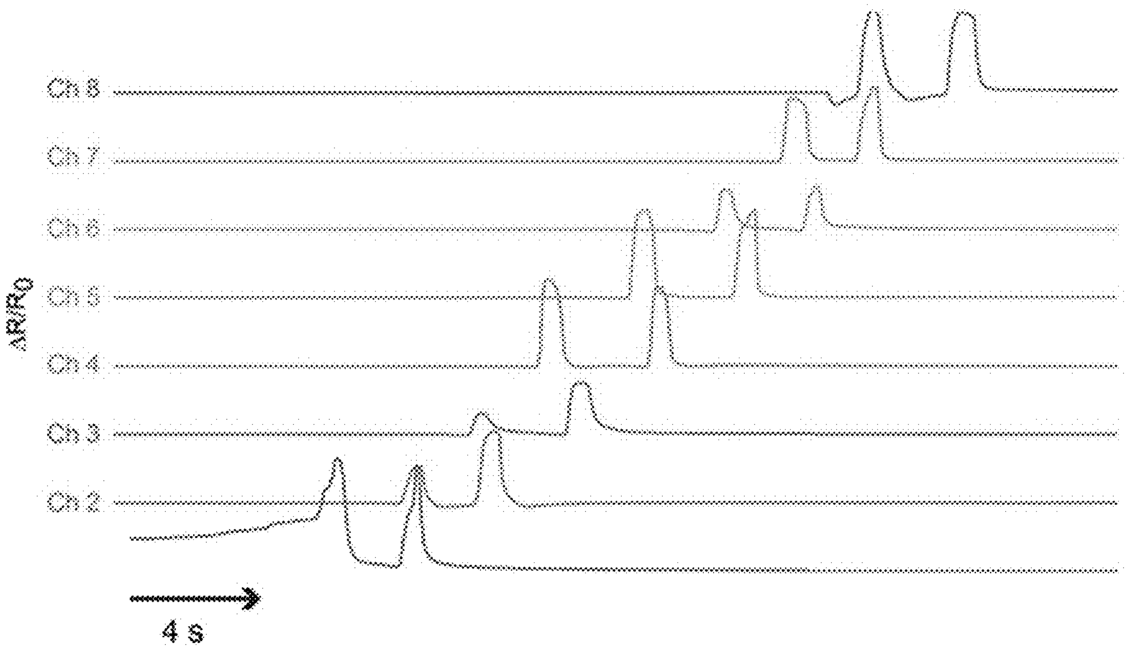
FIG. 55 is a plot of a multi-channel pressure recording of the manometry device of FIG. 46 during movement of the artificial bolus of FIG. 53 according to FIG. 54.
Figure 56:
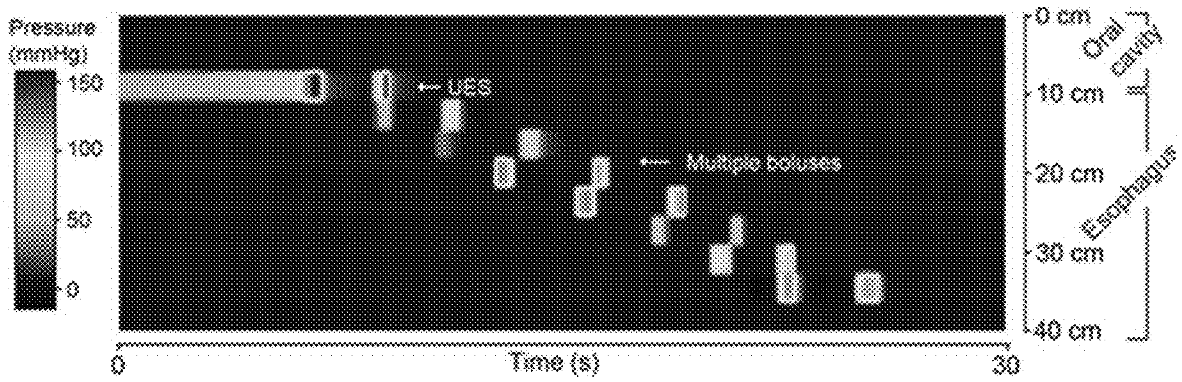
FIG. 56 is another plot of the multi-channel pressure recording of the manometry device of FIG. 46 during movement of the artificial bolus of FIG. 53 according to FIG. 54, illustrating the location of the measured pressures.

In another experiment, we attached two separate food boluses, approximately 5 centimeters apart, onto the tip of the endoscope and passed them down the esophagus (see FIGS. 53 and 54). The multi-channel pressure recording (see FIG. 55) and the resulting pressure color plot (see FIG. 56) demonstrated well-distinguished, simultaneous pressure events due to the presence of two boluses, implying its utility in detecting the dysmotility with simultaneous contractions and those that may lead to food bolus retention. The overall measurement range and sensitivity were more than adequate to identify UES hypotension or hypertension with pressure differentials up to 180 mmHg for additional diagnostic value.

Figure 57:
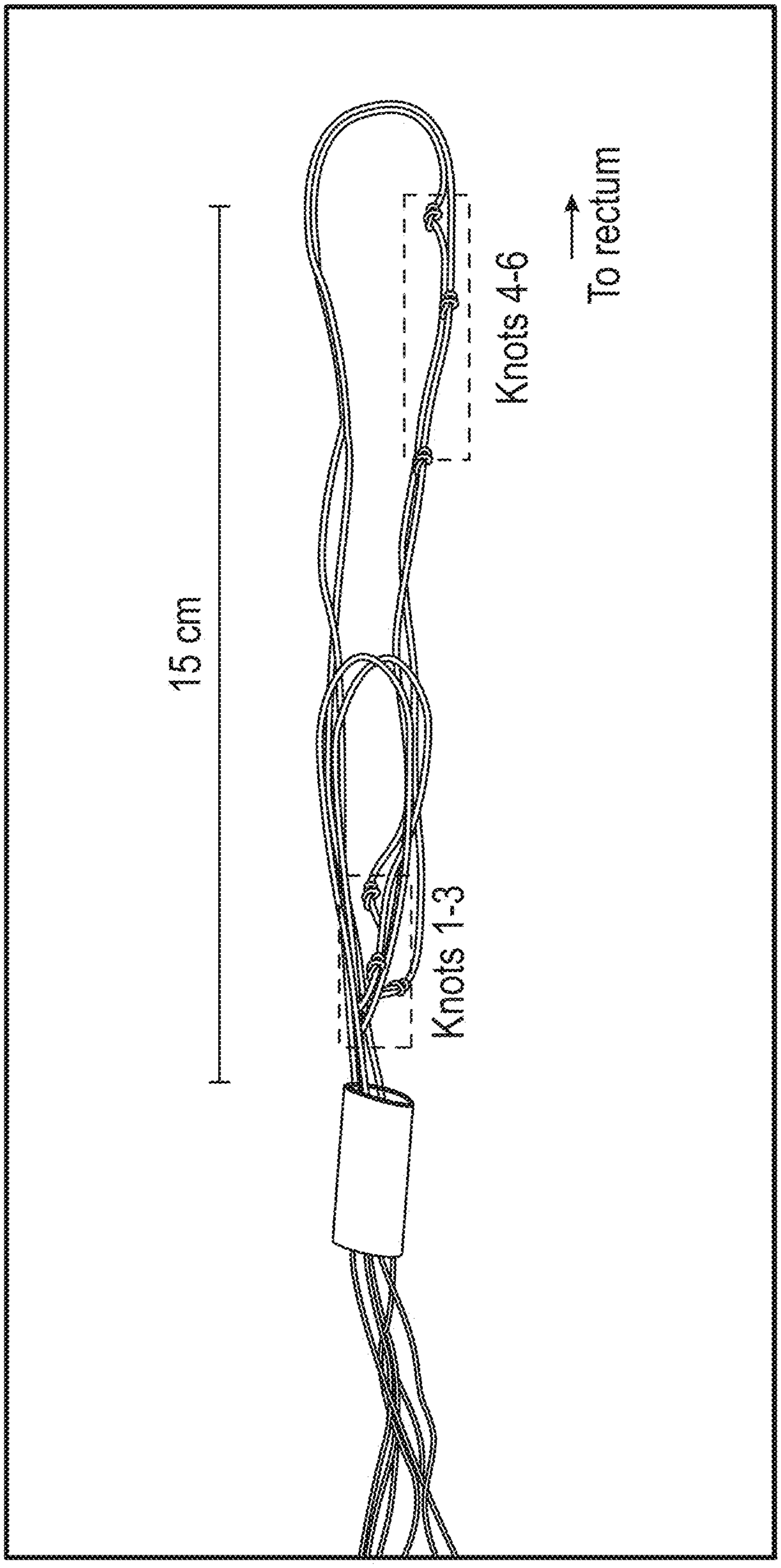
FIG. 57 is an image of a manometry device (SPS) having six restrictions (sensors) configured as overhand knots for use in the RAIR evaluation of FIG. 45.

In the second study, we performed the standard RAIR measurement where a Foley catheter (18 Fr) was inserted approximately 13 centimeters proximal to the anal verge and inflated with water to induce a transient, involuntary relaxation of the anal sphincter. Sensing mode 1 (see FIG. 37) was used here to distinguish simultaneous pressure changes in the rectum and the anal canal that were approximately 10 centimeters apart. The six-channel SPS consisted of three knots at the front spaced with approximately 2 centimeter intervals for recording in the rectum, and three knots at the rear with approximately 1 centimeter intervals for recording in the anal canal (see FIG. 57). UV curing adhesive was used to bond six channels into one, yielding an overall device diameter of approximately 2 millimeters.

Figure 58:
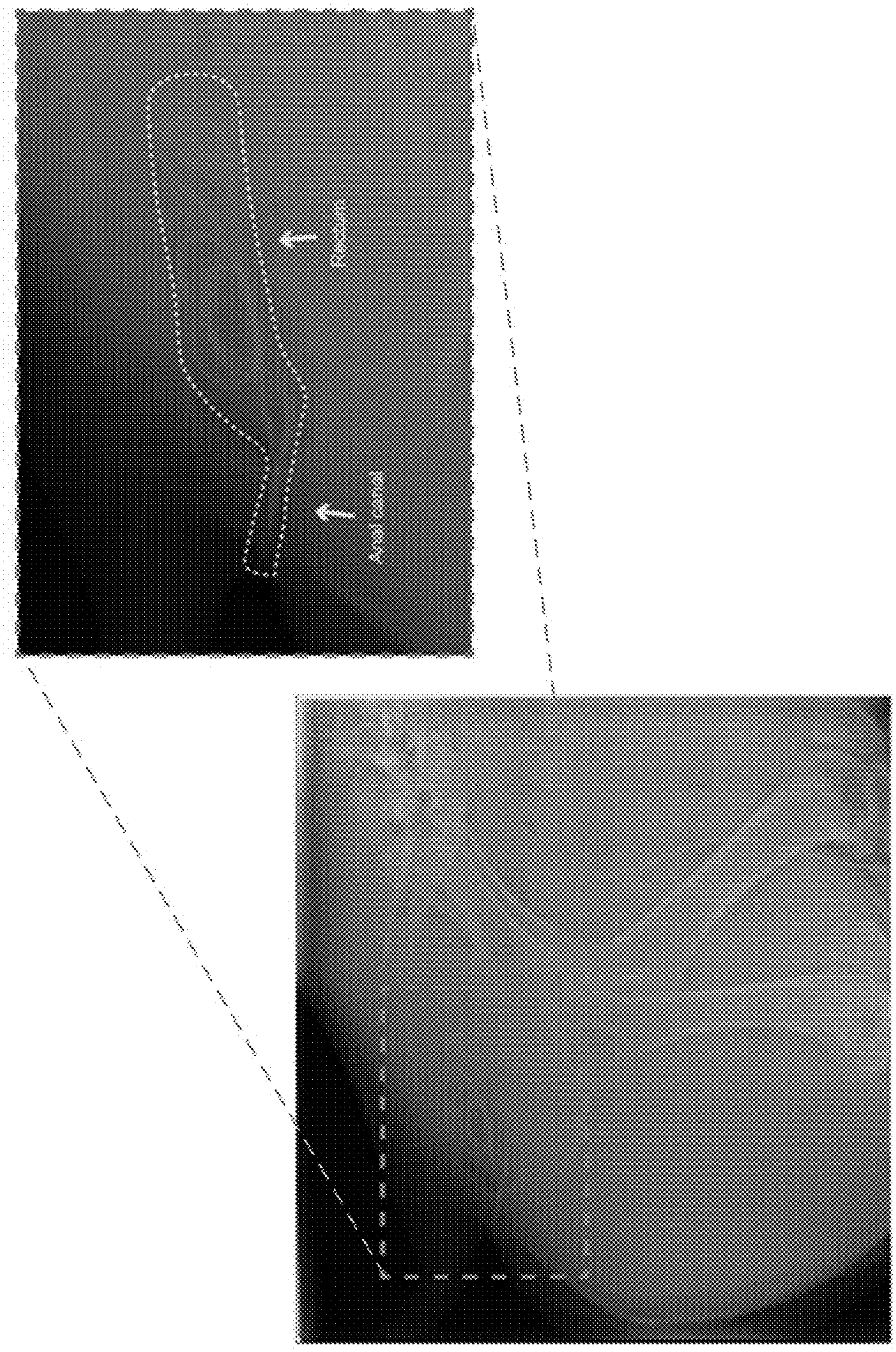
FIG. 58 is an image of the manometry device of FIG. 57 placed in the rectum of the porcine model of FIG. 45 for measurement of rectoanal pressure.

The device slid easily approximately 15 centimeters proximal to the anal verge with endoscopic assistance, which was further confirmed with x-ray imaging (see FIG. 58). No twisting or entanglement of the device was found, which can be a common issue for known small-diameter flexible catheters. A Foley catheter was then inserted into the rectum and rapidly inflated with different amount of water (e.g., 10 milliliters, 30 milliliters, 50 milliliters, or 100 milliliters) followed by deflation, which was repeated three times for each volume. The resistance of each channel was measured simultaneously using the resistance analyzing circuit (e.g., a resistance measurement device) with a sampling rate of 14 Hertz per channel.

Figure 59:
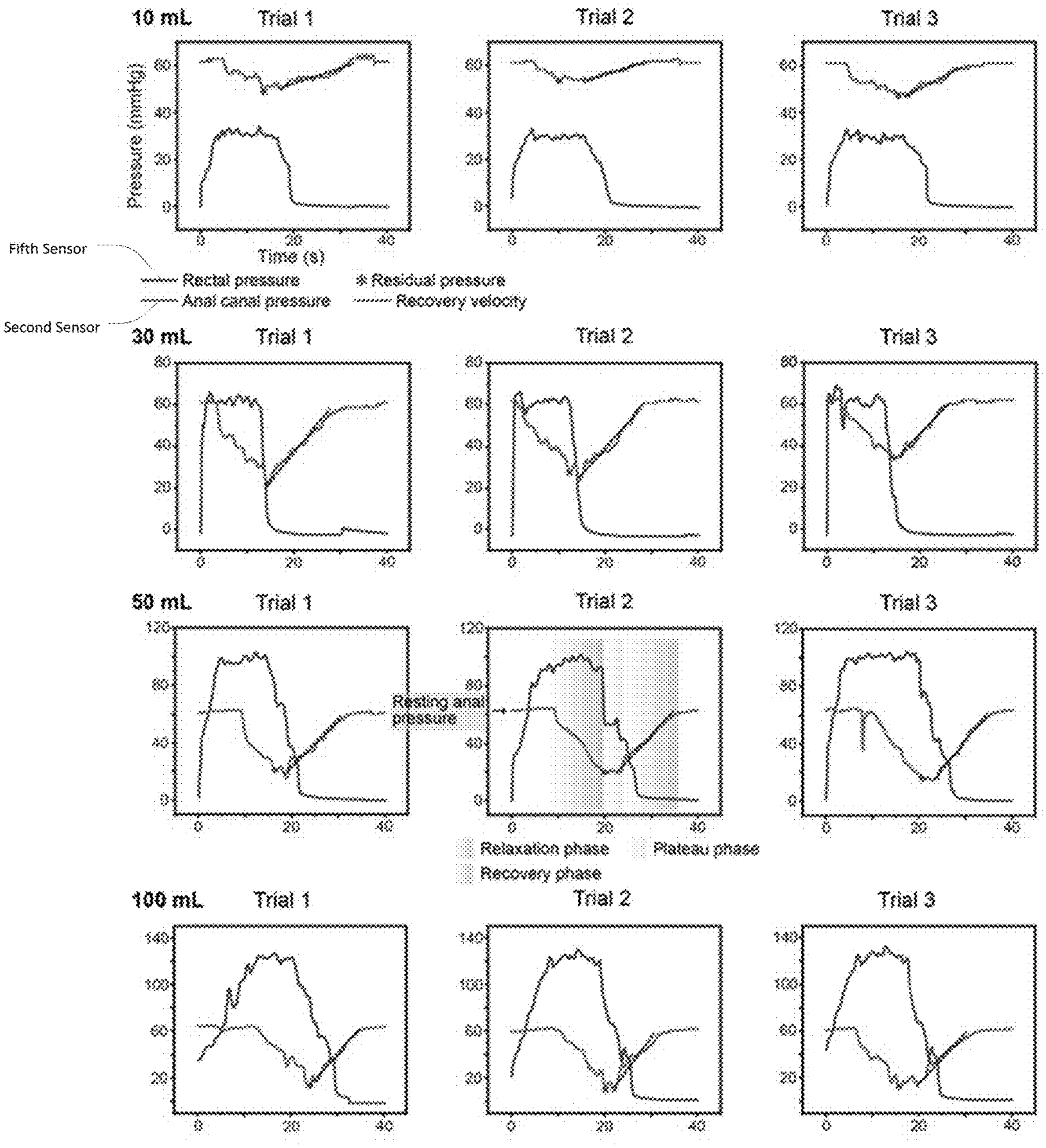
FIG. 59 is a plot of the pressure responses measured by the second and fifth sensors (knots) of the manometry device of FIG. 57 during the RAIR evaluation of FIG. 45.
Figure 61:
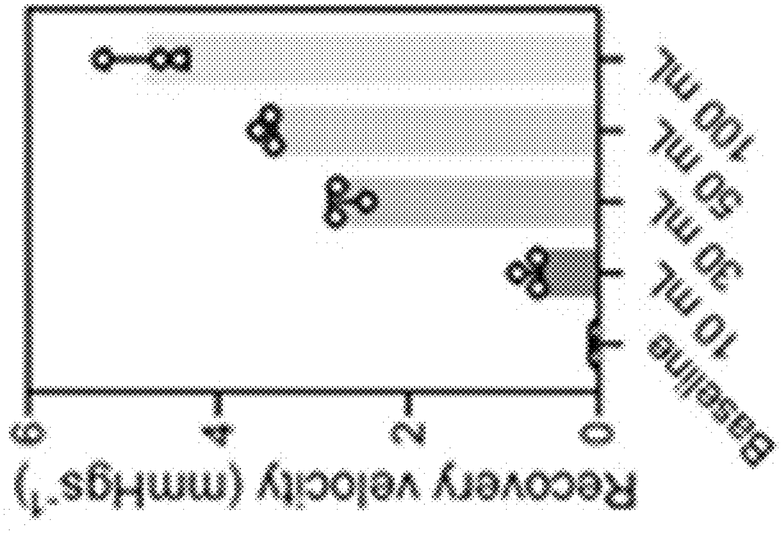
FIG. 61 is a plot illustrating recovery velocity as a function of inflation volume for the RAIR evaluation of FIG. 45 with the manometry device of FIG. 57, showing an increasing trend as inflation volume increased.
Figure 60:
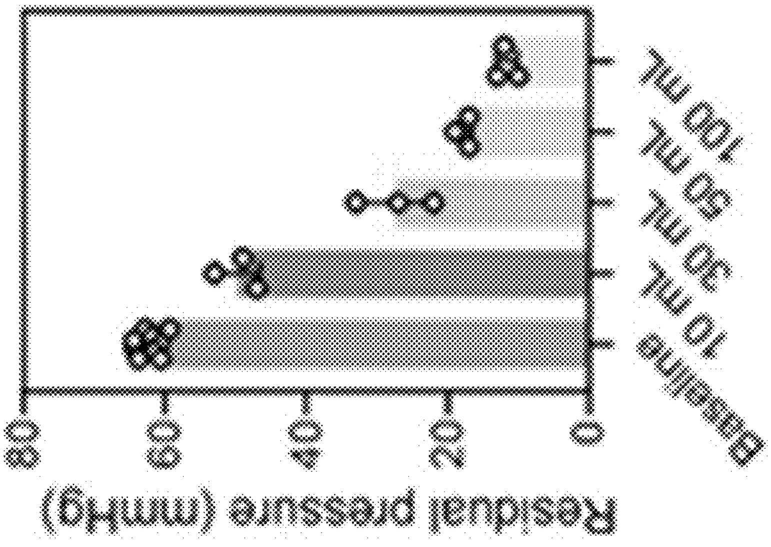
FIG. 60 is a plot illustrating residual pressure as a function of inflation volume for the RAIR evaluation of FIG. 45 with the manometry device of FIG. 57, showing a decreasing trend as inflation volume increased.

During testing, a rise in rectal pressure was registered by the fifth sensor (approximately 12 centimeters from the anal verge) immediately after inflating the Foley catheter with water, and a gradual drop in anal pressure was recorded by the second sensor (approximately 2 centimeters from the anal verge) with a temporal delay. The anal pressure completely recovered to its baseline approximately 5 seconds to 15 seconds after the Foley catheter was deflated. The pressure responses of second and fifth sensors derived from their respective resistive changes during all four trials, inflation with approximately 10 milliliters, 30 milliliters, 50 milliliters, and 100 milliliters of water, respectively, are shown plotted in FIG. 59. All three major phases (relaxation, plateau, and recovery) that described the dynamic nature of the RAIR can be identified (see FIG. 59), from which diagnostic information such as the resting anal pressure (RAP), residual pressure (RP), and recovery velocity (RV) can be deduced. For example, the RP, defined as the final pressure value of the relaxation phase, reduced from 49.7±2.5 mmHg to 11.7±1.2 mmHg (see FIG. 60), while the RV, defined as the linear slope of the recovery phase, climbed from 0.71±0.1 $mmHgs^{-1}$ to 4.75±0.3 $mmHgs^{-1}$ as the inflation volume increased from 10 milliliters to 100 milliliters (see FIG. 61).

Benchmarking the SPS Against Clinically Available Pressure Sensors

Figure 62:
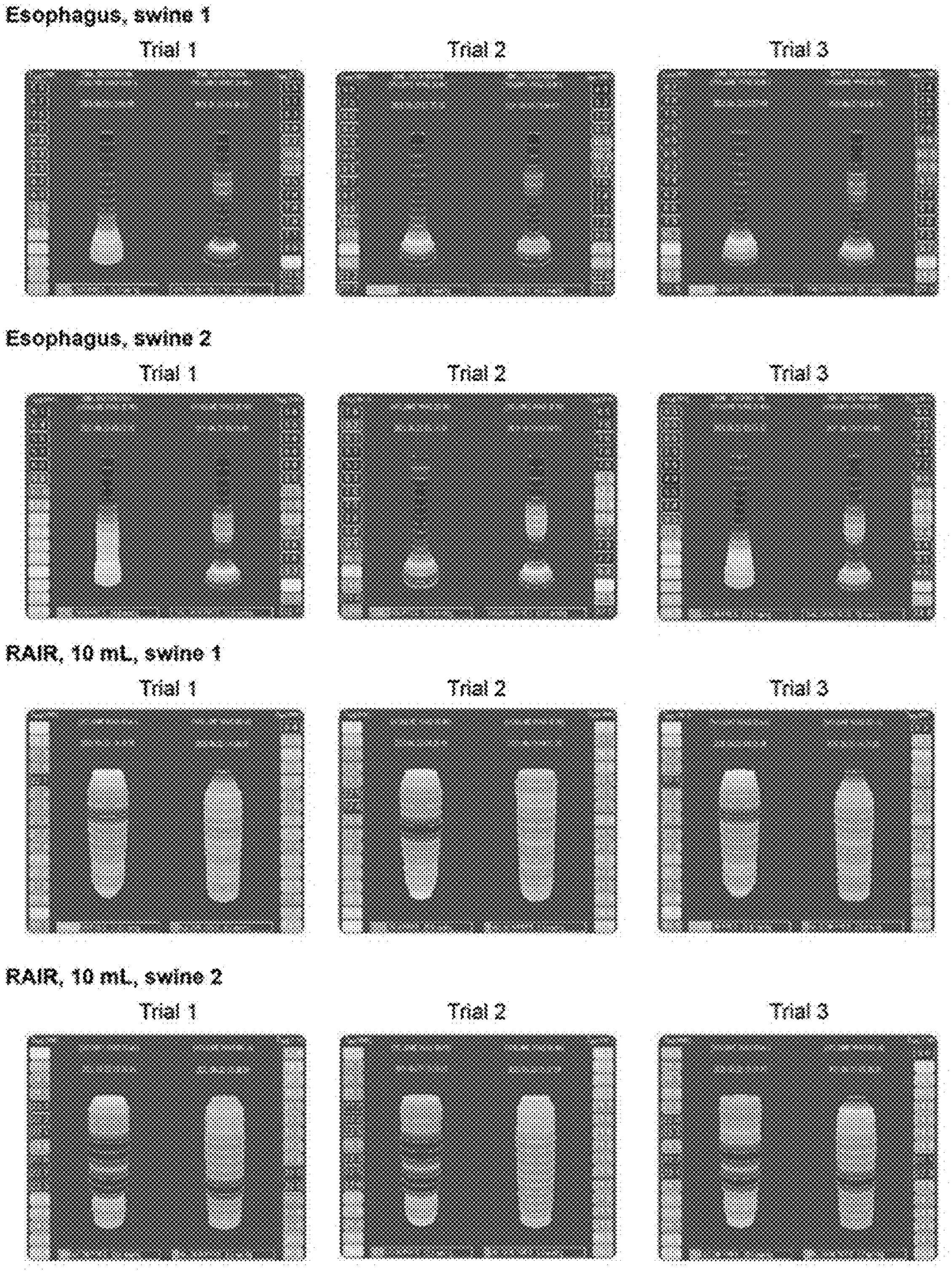
FIG. 62 is a series of plots illustrating endoluminal functional luminal-imaging probe (EndoFLIP) measurements for both esophageal pressure and RAIR, with the left and right frame for each esophageal pressure measurement corresponding to before and after the insertion of an artificial bolus, respectively, and the left and right frame for each RAIR measurement corresponding to before and after rectal distention with 10 milliliters inflation, respectively.

As a final demonstration, we benchmarked the SPS against the clinically available pressure sensors (EndoFLIP, HRM) for GI motility evaluations. We first compared the in vivo performance of the SPS with EndoFLIP, a well-established technology for sensing endoluminal distensibility that has clinically demonstrated correlation with HRM. EndoFLIP exploited a single solid-state pressure transducer inside a balloon catheter that was inflated with diluted saline to record the intra-balloon pressure, which can precisely evaluate the endoluminal pressure with a resolution of 0.1 mmHg but lacks spatial resolution. We performed the above in vivo esophageal and RAIR measurements using the SPS and EndoFLIP respectively, which were repeated on two porcine models. The screen clips of EndoFLIP measurements are summarized in FIG. 62.

Figure 63:
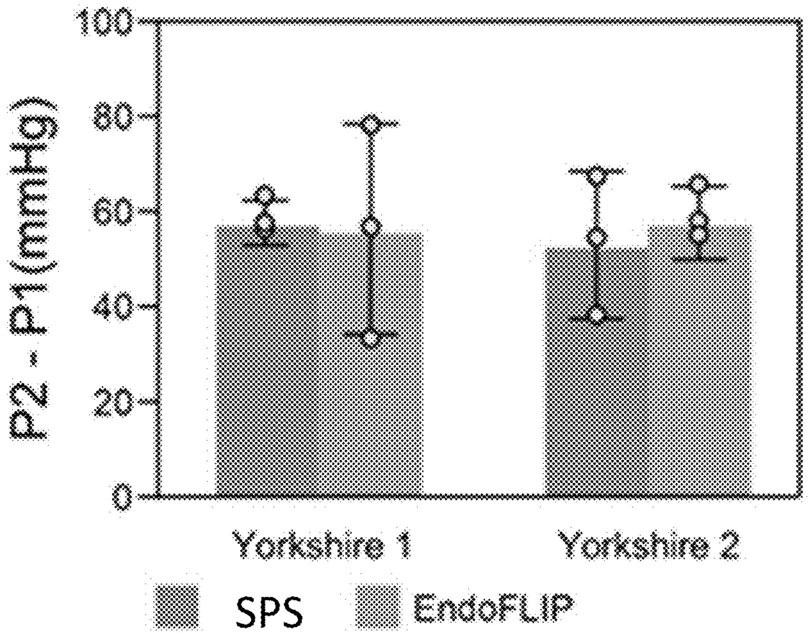
FIG. 63 is a plot comparing a measured difference between a peak esophageal pressure measured as a bolus passed (P2) and a resting upper esophageal sphincter (UES) pressure (P1) using an SPS and EndoFLIP.

During the esophageal experiment, we first identified the location of the UES using an endoscope, placed the SPS and EndoFLIP at the UES to record the resting UES pressure (P1), and then passed the bolus-attaching endoscope through the UES to record the peak pressure as bolus passed (P2). We found that P1 obtained from EndoFLIP was greatly affected by the choice of initial inflation volume of the balloon catheter; larger inflation volumes resulted in higher P1 values. We used a clinically recommended inflation volume of 20 milliliters, which yielded lower P1 and P2 compared with those recorded by the SPS. The averaged pressure difference, P2−P1, was within 10-percent between results from the SPS and EndoFLIP (see FIG. 63), supporting the capacity of the SPS in evaluating relative pressure changes.

Figure 64:
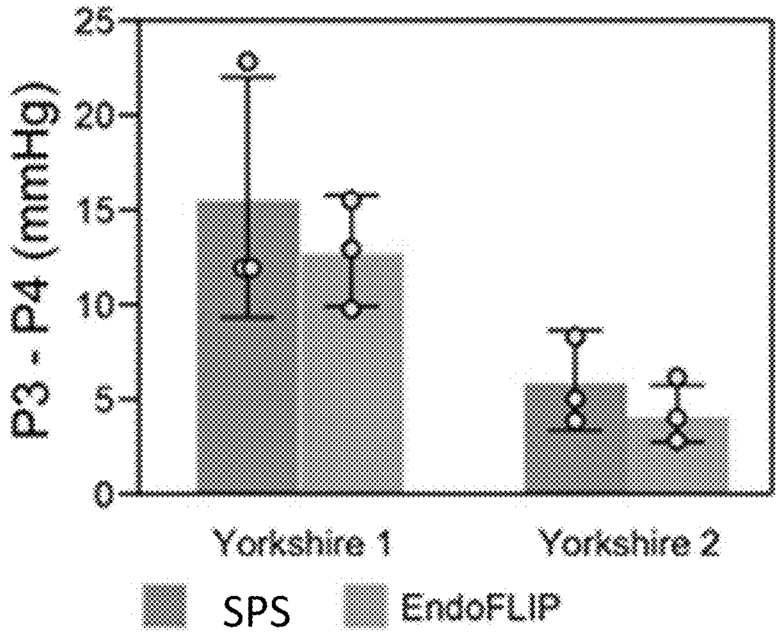
FIG. 64 is a plot comparing a measured difference between resting anal pressure (P3) and residual anal pressure (P2) using an SPS and EndoFLIP.

During the RAIR evaluation with an inflation volume of 10 milliliters using a Foley catheter in the rectum, the EndoFLIP balloon catheter (160 millimeters in length) was too long to be placed entirely inside the anal canal, which may be responsible for both lower resting anal pressures (P3) and residual pressures (P4) compared with results from the SPS that sat completely within the high-pressure region of anal canal. On the other hand, the averaged pressure difference, P3−P4, was within 30-percent between the two systems (see FIG. 64). The percentage errors from multiple (n=3) measurements were comparable (FIGS. 63 and 64), demonstrating good overall consistency of the two systems in evaluating common GI motility behaviors.

Next, we benchmarked the SPS against a currently available HRM system, the current standard for GI motility evaluations, both in vitro and in vivo using porcine models. In particular, for the HRM system, we used a Medtronic ManoScan® 360 Manometry system equipped with esophageal catheters. The HRM system had 36 solid-state pressure sensors spaced in 1 centimeter intervals with an overall diameter of approximately 4 millimeters. Each sensor was further divided into an array of twelve circumferential solid-state micro-transducers, and the final pressure recording in each channel was an averaged value from all twelve circumferential transducers during a total time span of approximately two seconds.

Figure 65:
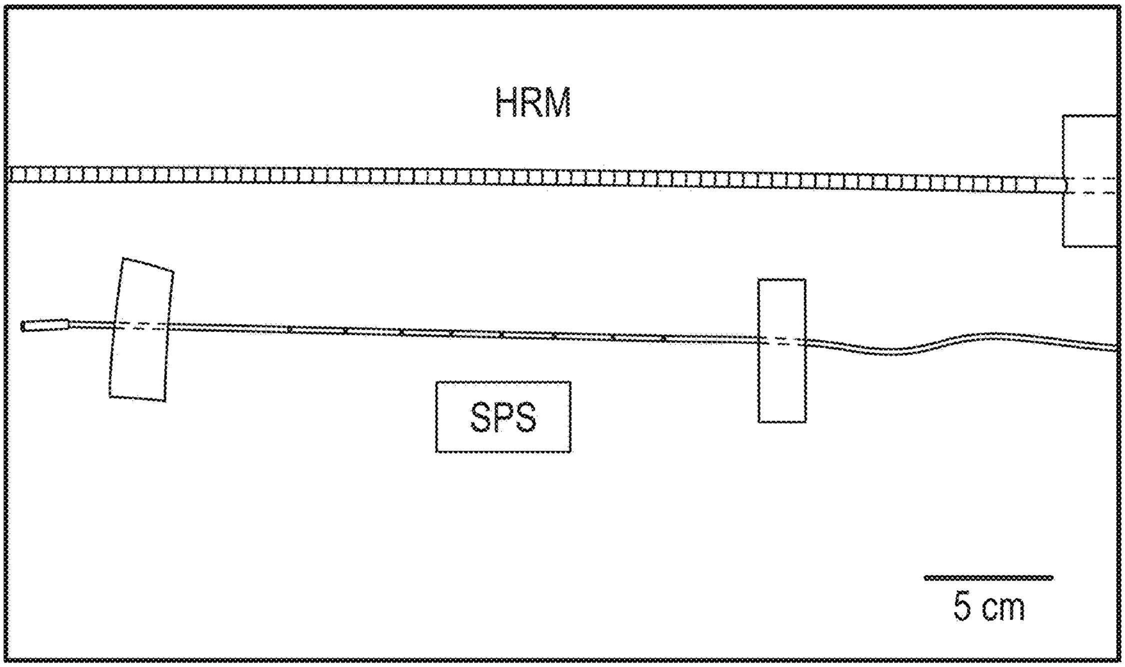
FIG. 65 is an image comparing an SPS with an HRM.

To better understand the performance of the SPS, we first conducted benchtop comparison with HRM (see FIG. 65). We ran two tests using (I) a set of different calibration weights (e.g., 20 grams, 50 grams, 100 grams and 200 grams) placed onto the pressure sensors, and (II) a rolling test similar to FIG. 41 using a 50-gram calibration weight. The total number of knots in the SPS was set to eight with an average spacing of approximately 2 centimeters for this test.

Figure 66A:
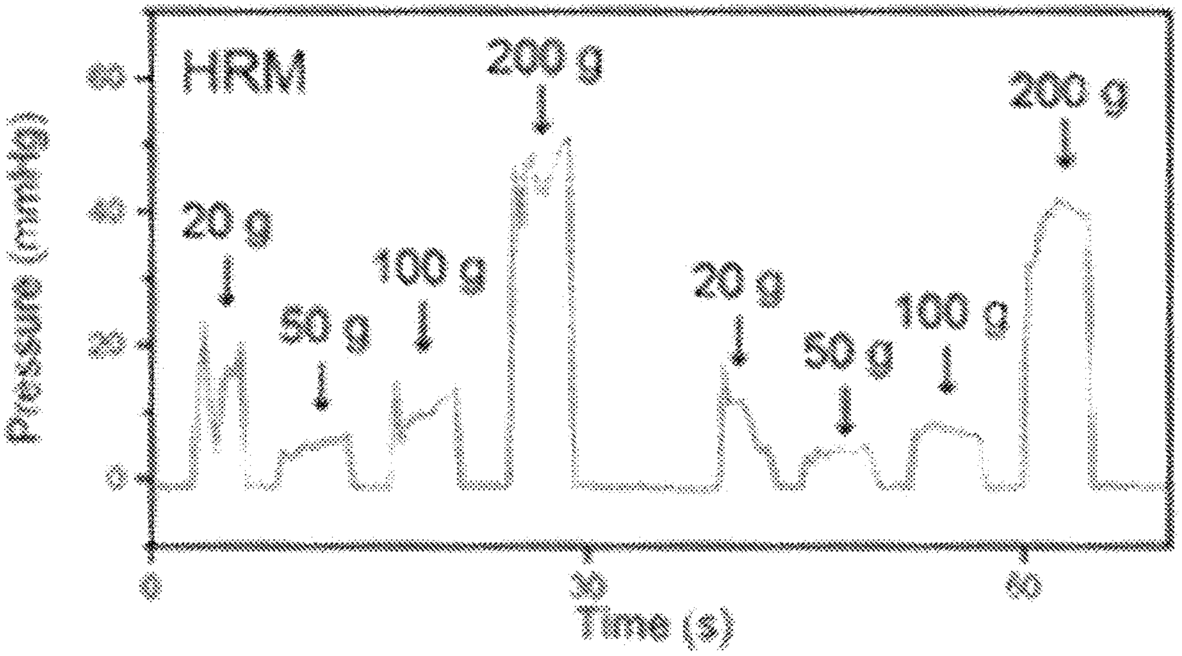
FIG. 66A is a plot illustrating a pressure recording obtained with the HRM of FIG. 65, during placement of various calibration weights.
Figure 66B:
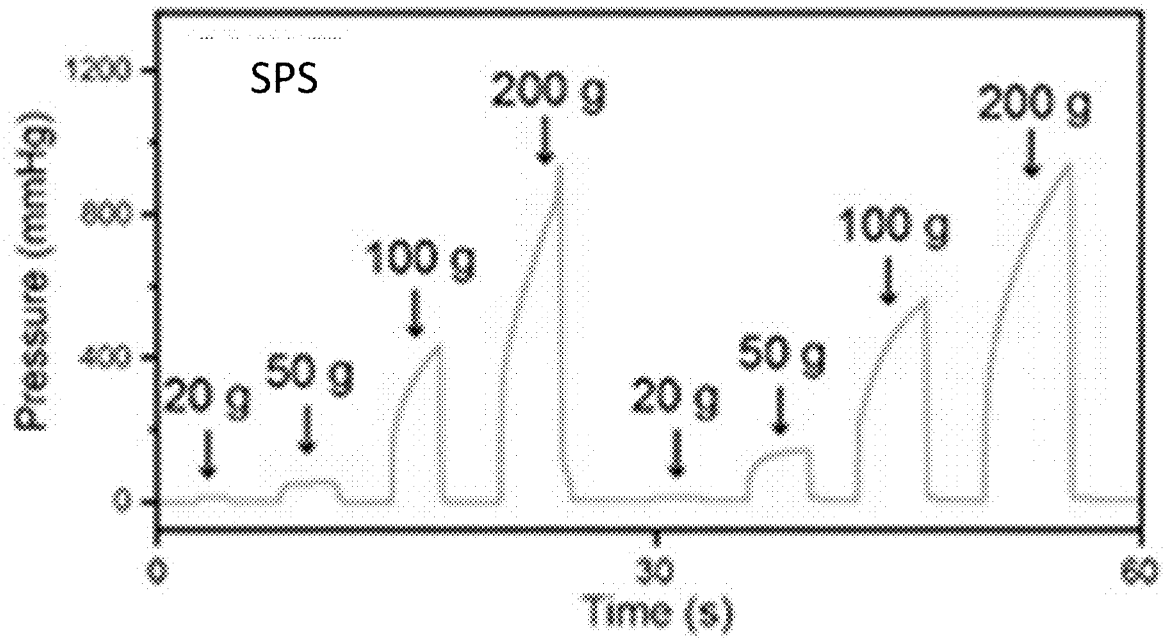
FIG. 66B is a plot illustrating a pressure recording obtained with the SPS of FIG. 65, during placement of various calibration weights.
Figure 67A:
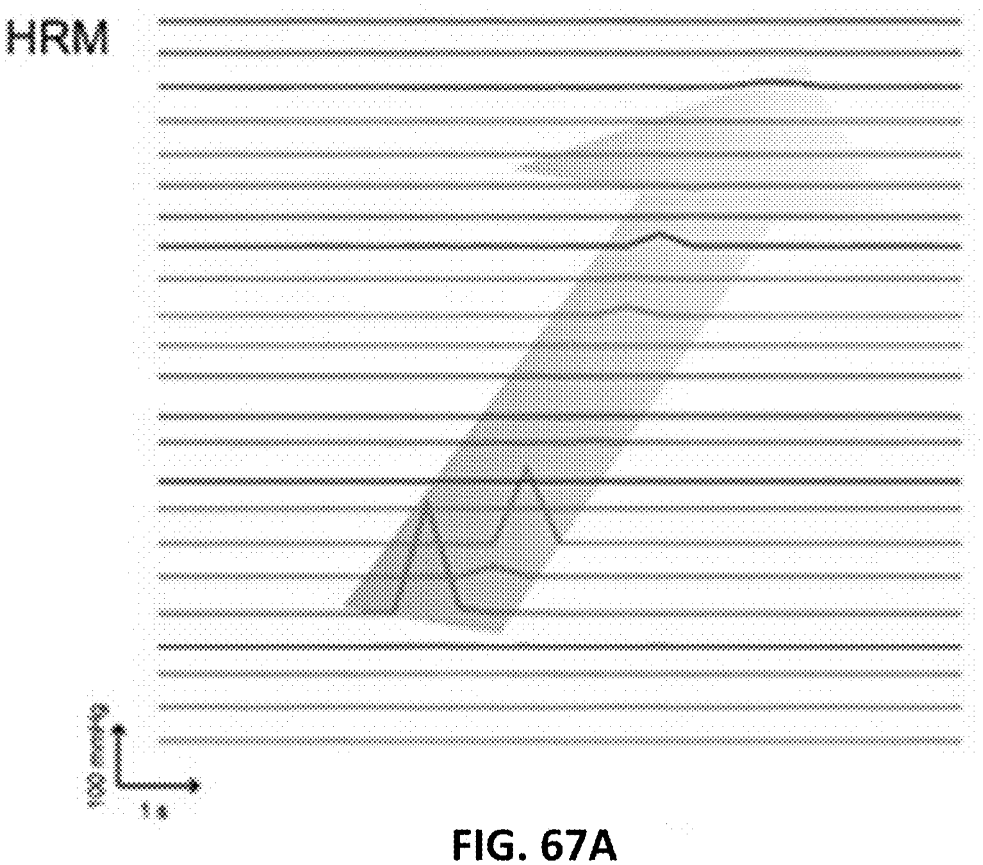
FIG. 67A is a plot illustrating a pressure recording obtained with the HRM of FIG. 65, during rolling of a 50-gram weight across a fixed length of the HRM.
Figure 67B:
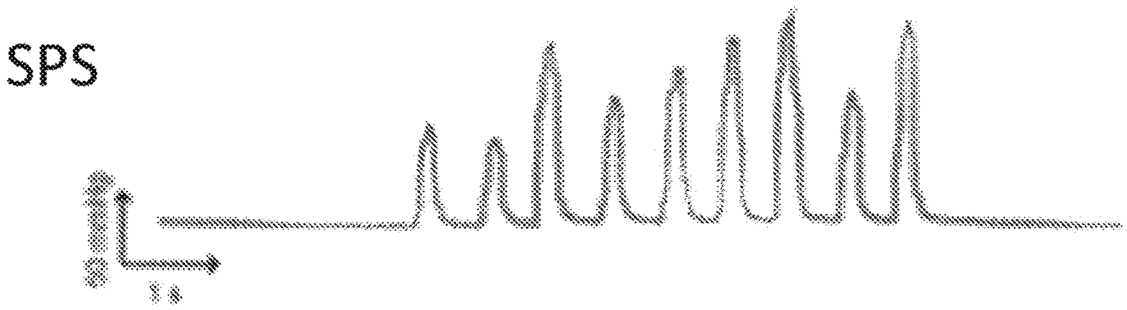
FIG. 67B is a plot illustrating a pressure recording obtained with the SPS of FIG. 65, during rolling of a 50-gram weight across a fixed length of the SPS.

As illustrated in FIGS. 66A and 66B, both HRM and the SPS were able to distinguish different weights with good repeatability, while the SPS performed better in recognizing the smaller weights (e.g., 20 grams and 50 grams) than HRM. The pressure magnitudes recorded by the SPS were larger than those by HRM, which made sense as the SPS had a significantly smaller diameter than HRM (see FIG. 65), and each applied pressure was estimated by the weight divided by the cross-sectional area of the catheter. In the second test, we rolled a 50 gram calibration weight across a fixed length (e.g., approximately 15 centimeters) on both HRM and the SPS in a total time of approximately 2 seconds. Notably, as shown in FIGS. 67A and 67B, the temporal resolution of the SPS (4 Hertz dictated by the recording hardware) was better than that of HRM (0.5 Hertz) in revealing detailed pressure profiles during fast traveling of the object at a speed of approximately 7.5 centimeters per second.

Figure 68:
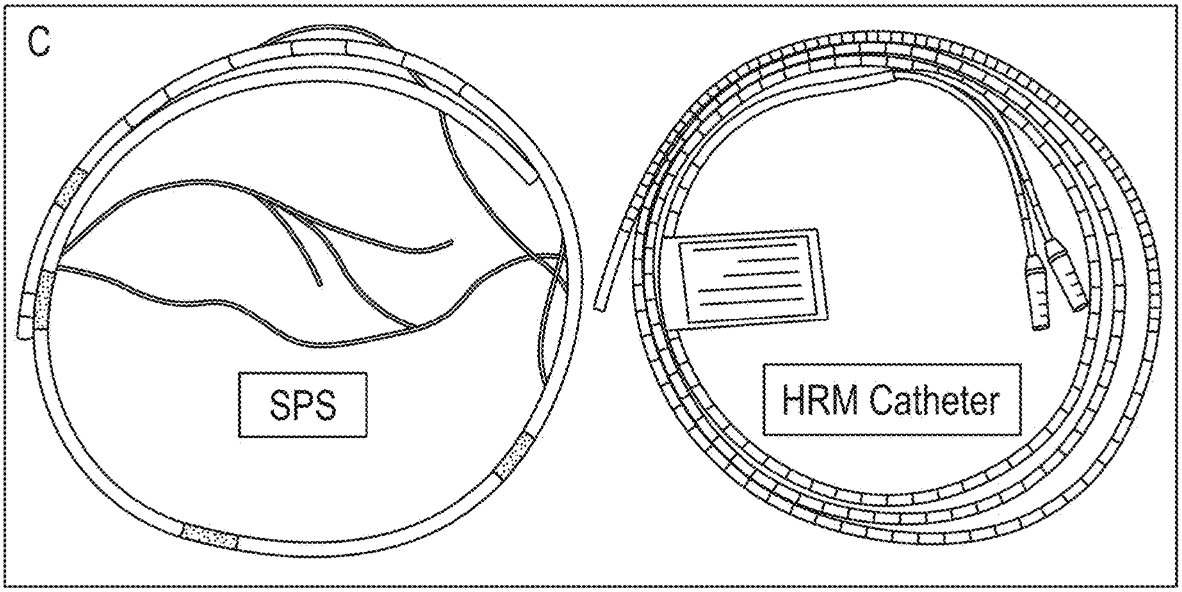
FIG. 68 is an image of an SPS attached onto a polyurethane tube next to an HRM catheter.
Figure 69:
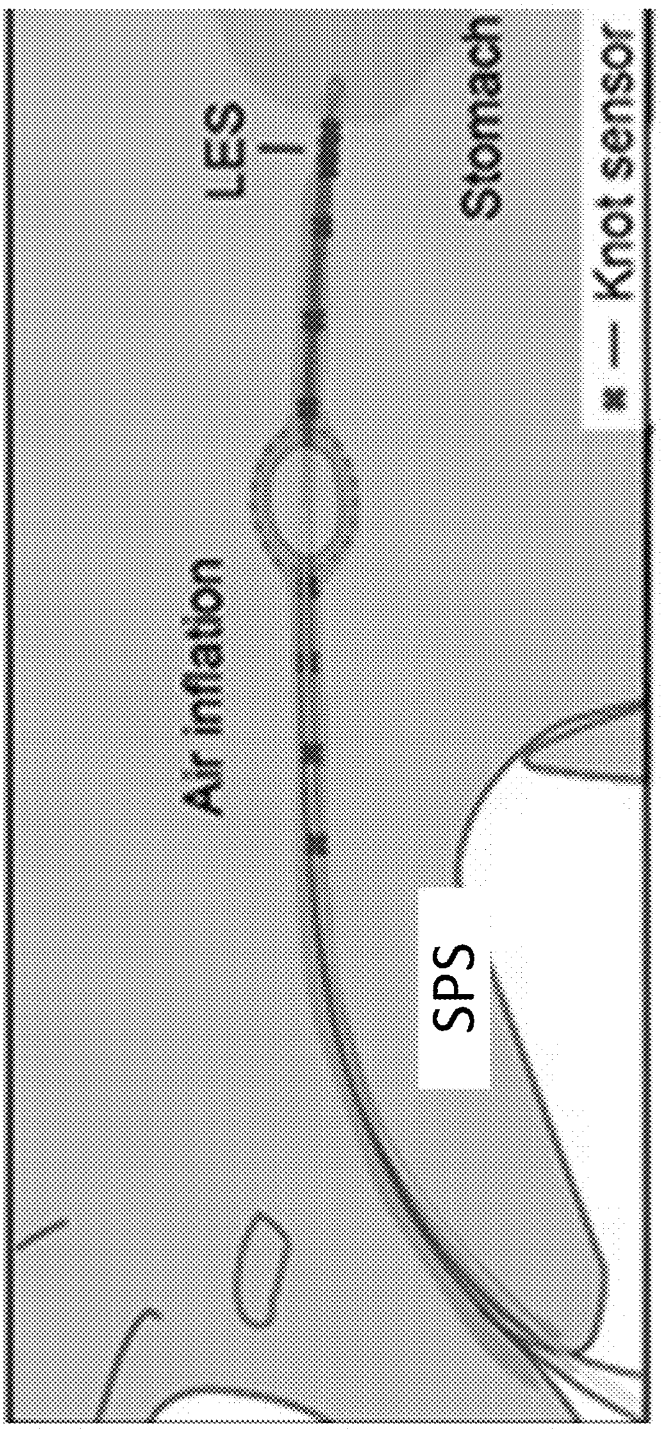
FIG. 69 is a schematic illustration of an experimental setup used for evaluation of distention-induced esophageal peristalsis (DIEP).
Figure 71:
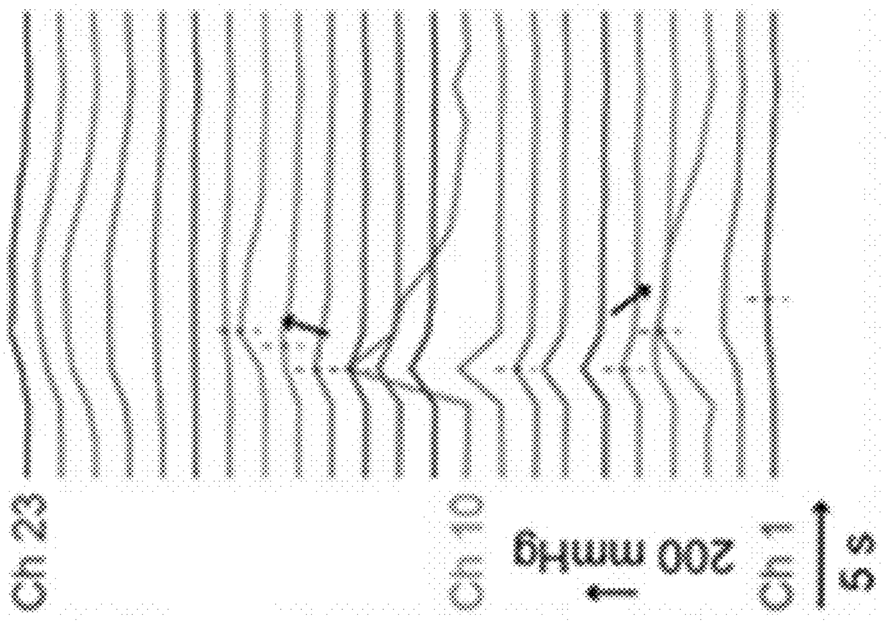
FIG. 71 is a detail view of the plot of FIG. 70 showing the first five seconds of the multi-channel pressure recording of DIEP.

Furthermore, we performed in vivo evaluations of HRM and the SPS using a female Yorkshire swine with a weight of approximately 39 kilograms. To mimic the overall dimensions and mechanical stiffness of HRM, we attached the SPS onto a polyurethane tube with similar outer diameter (e.g., approximately 4 millimeters) and radius of curvature (e.g., degree of bending, see FIG. 68). However, instead of passing the artificial bolus, we induced secondary peristalsis of the esophageal body in lightly anesthetized swine (e.g., using an approximately 1.8-percent to 2-percent isoflurane in oxygen for between 30 minutes and 60 minutes) by placing a balloon catheter transorally into the esophagus at a depth of approximately 60 centimeters and inflating with approximately 15 milliliters of air, as illustrated in FIG. 69.

Figure 70:
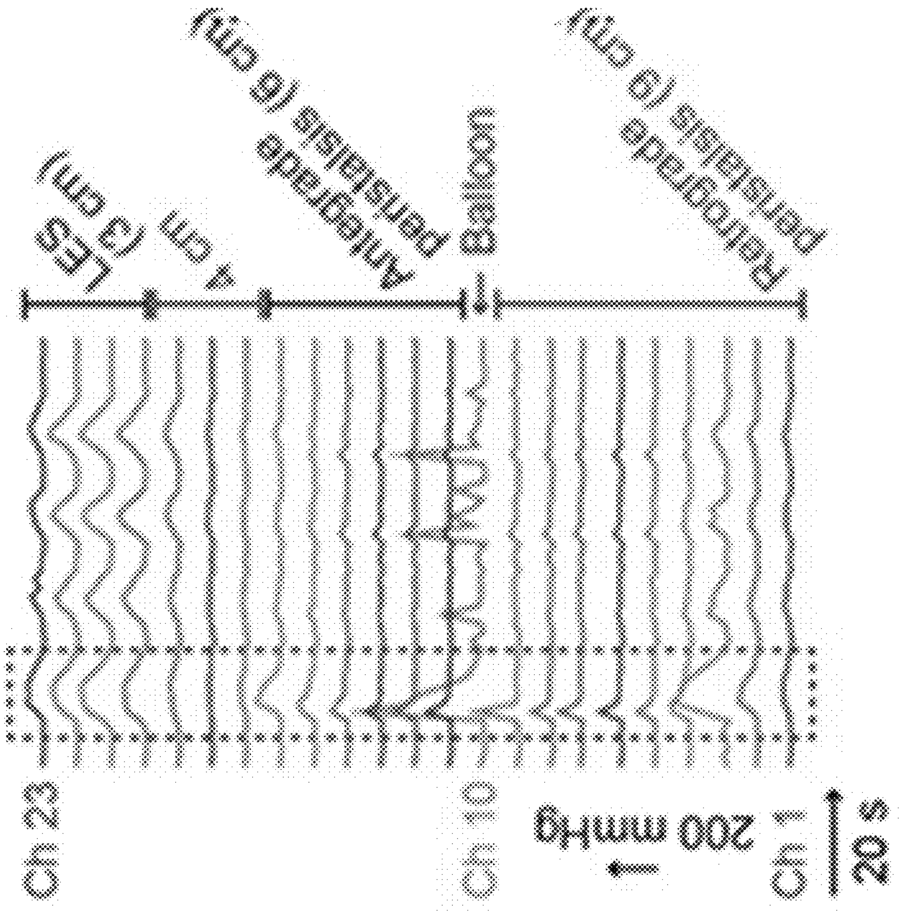
FIG. 70 is a plot illustrating a multi-channel pressure recording of DIEP obtained with the HRM of FIG. 68.

Using the HRM catheter placed transorally into the esophagus at a depth of approximately 85 centimeters, we recorded symmetric, bi-directional peristaltic waves initiated at the location of balloon inflation (see FIG. 70). Both antegrade and retrograde peristaltic waves were observed as the esophagus reflexively tried to push the inflated balloon upward or downward in efforts to dislodge it. The antegrade peristaltic wave culminated with a contraction in the lower esophageal sphincter (LES) approximately 10 centimeters away from the site of balloon inflation (see FIG. 70), likely representing the rebound contractions often seen in the human LES immediately at the end of a peristaltic swallow. Although details were elusive in the time domain (see FIG.

71) due to relatively poor temporal resolution (0.5 Hertz), the fine spatial resolution (e.g., approximately 1 centimeters) of HRM enabled pressure color plot of the esophageal motility (see FIG. 72) that resolved the essential components such as the antegrade and retrograde peristalsis and the LES contraction.

Figure 73:
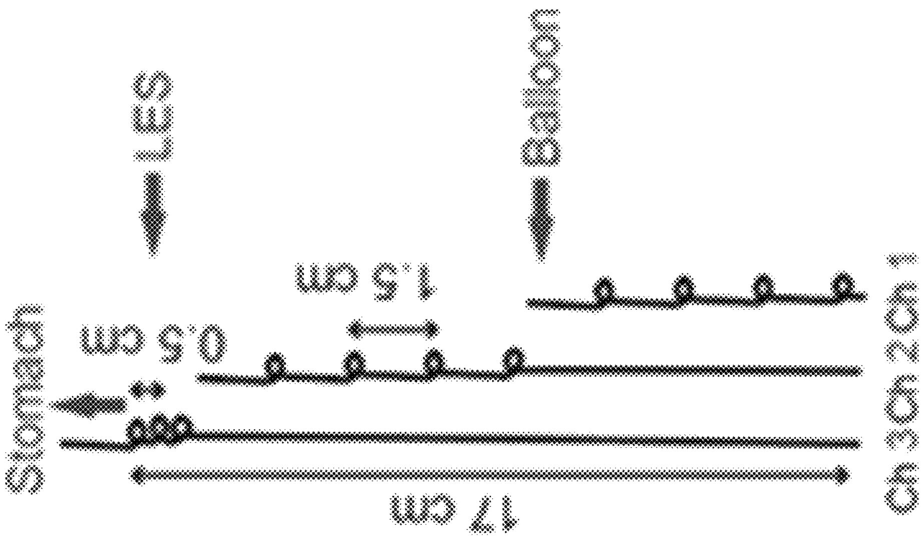
FIG. 73 is a schematic view illustrating a layout of knots and channels for measuring DIEP for the SPS of FIG. 68.
Figure 72:
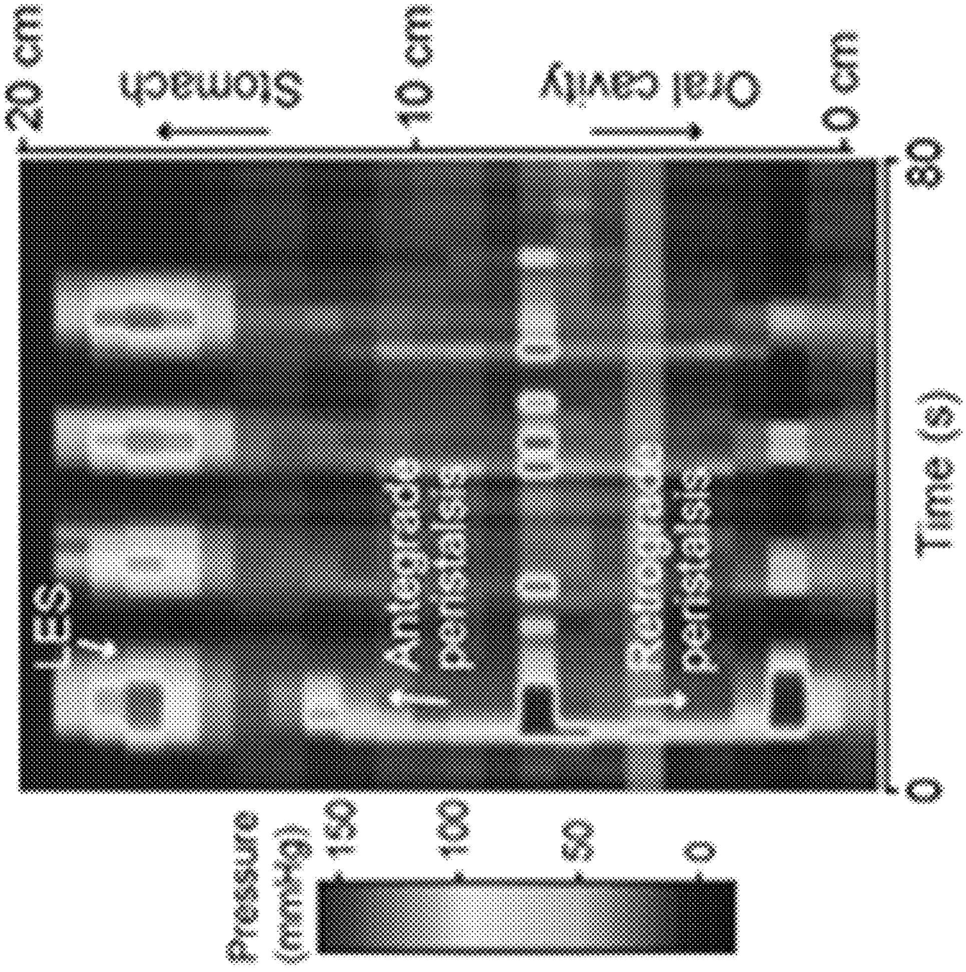
FIG. 72 is another plot illustrating the multi-channel pressure recording of DIEP of FIG. 70.
Figure 74:
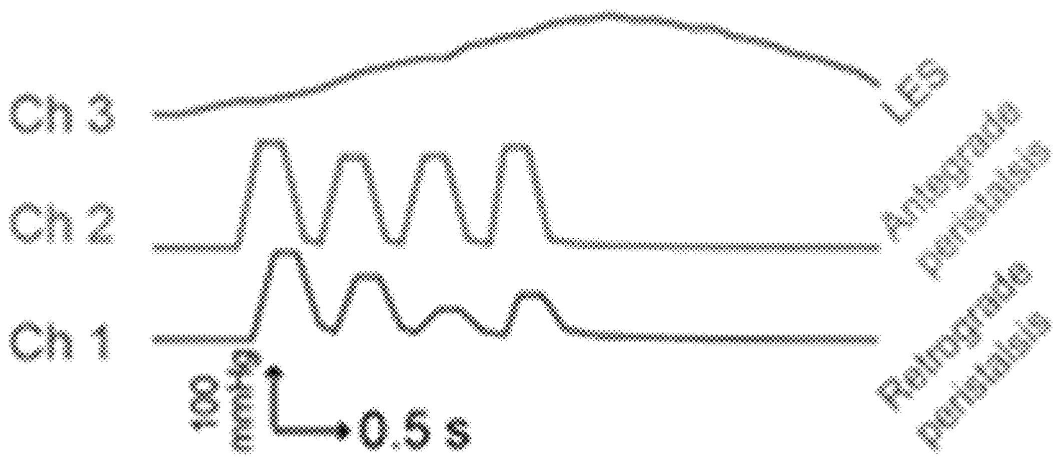
FIG. 74 is a plot illustrating a multi-channel pressure recording of DIEP obtained with the SPS of FIG. 68.
Figure 75:
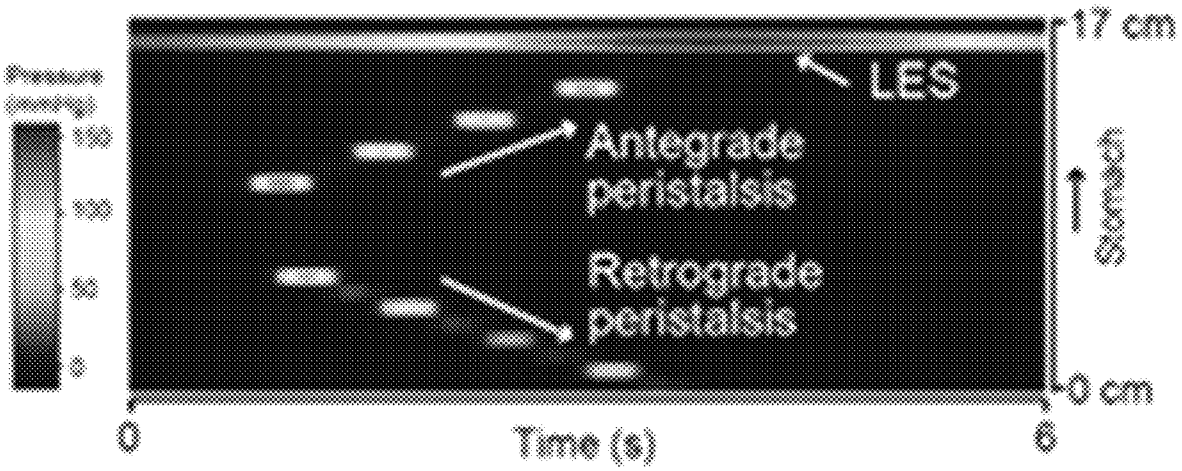
FIG. 75 is another plot illustrating the multi-channel pressure recording of DIEP of FIG. 74.
Figure 76:
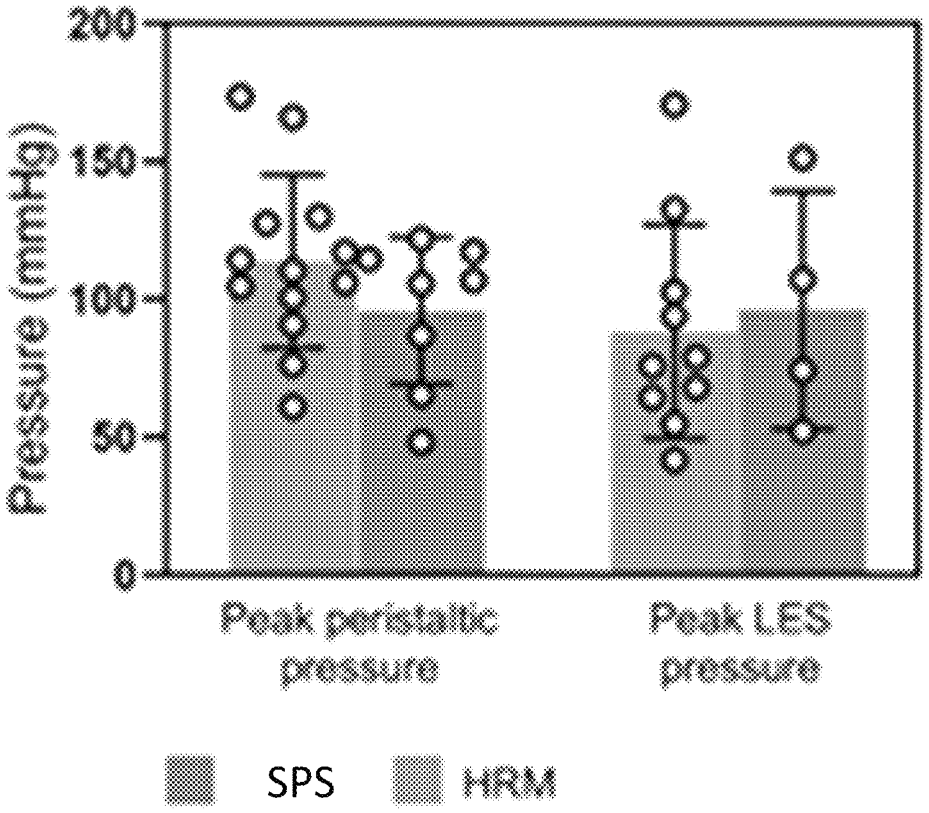
FIG. 76 is a plot comparing the peak peristaltic pressure and peak lower esophageal sphincter pressure measured using the SPS and HRM of FIG. 68.

Because the distention-induced peristaltic wave was bi-directional, we configured the SPS, as illustrated in FIG. 73, with three independent channels spanning a total length of approximately 17 centimeters to record the antegrade, retrograde, and LES pressure activities, respectively. Pressure spectra during a typical peristaltic event recorded by the SPS (see FIG. 74) revealed more features than those by HRM (see FIG. 72) due to the better temporal resolution (e.g., approximately 4 Hertz dictated by the recording hardware). The spacing between each sensory node of the SPS (e.g., approximately 1.5 centimeters) was slightly larger than that of HRM (e.g., approximately 1 centimeter), which resulted in lower spatial resolutions, but the resultant pressure color plot (see FIG. 75) was able to capture the essential information as shown in FIG. 72 obtained from HRM. Finally, we compared the peak pressure during the secondary peristalsis and during the contraction of LES recorded by HRM and the SPS (see FIG. 76), and found them to be within a twenty-percent difference with comparable error bars. These findings provide experimental support for benchmarking the SPS against the commercial HRM in evaluating certain GI motility patterns.

Together, these results show that the SPS can operate under in vivo conditions for at least two hours and extract real-time, spatially resolved information on GI motility across dynamic ranges consistent with human readings. The liquid metal-infused, knotting-based nature of sensor fabrication allows for a high degree of sensor reconfigurability tailored specifically for different application needs and budget considerations. For example, a variety of sensor configurations such as number of independent channels (e.g., 1 channel, 3 channels, 6 channel, and 8 channel), number of knots per channel (e.g., 1 knot, 3 knots, 4 knots, 7 knots, and 8 knots), knot spacing (e.g., 0.5 centimeters, 1 centimeter, 1.5 centimeters, 2 centimeters, and 5 centimeters), and total catheter lengths (e.g., 15 centimeters, 17 centimeters, 40 centimeters, 45 centimeters, and greater than 45 centimeters) has been exploited in this work to facilitate and accommodate different scenarios of pressure sensing both in vitro and in vivo, highlighting the ability of the SPS to customize and reconfigure.

The incorporation of multiple knots does not show interference or deterioration of signal quality, suggesting the possibility of further increasing node density to less than 1 centimeter spacing that may surpass the spatial resolution of state-of-the-art HRM (e.g., approximately 1 centimeter). Such level of spatial resolution may be useful to help identify physiologically distinct anatomical segments, such as the proximal (skeletal muscle) portion versus the distal (smooth muscle) portion on esophageal manometry. Additionally, it may be useful, from a machine-learning perspective, as the classification accuracy generally improves with the density of sensors. This implies that our approach can offer a simple and scalable approach towards unsupervised data analyses and diagnoses by achieving higher packing density of the sensors through knotting configurations.

From a sensor and design perspective, we highlight at least two key innovations that may be appealing to the biomedical community. The first innovation is the discovery of using basic knotting configurations to transform the otherwise insensitive silicone/eGaIn composites into devices capable of detecting small pressure changes within the human GI tract. This finding allows us to use low-cost, accessible materials and fabrication schemes while avoiding any complex materials or architectures that require lengthy preparation or expensive equipment, thereby providing cost-effective and disposable solutions that are in sharp contrast to the existing manometry systems. The second innovation is the introduction of multiplexing strategies by tying multiple knots onto a single conductor to minimize the number of channels without the need for complex and expensive multiplexer circuits. For conventional manometry catheters where each solid-state pressure transducer needs to be individually addressed using multiple wires, the total number of wires quickly multiplies to a degree that limits the maximum number of sensors that can be packed within one catheter, and thereby increasing the overall manufacturing challenge. The wire bundle also increases the diameter and mechanical stiffness of the catheter that can lead to increased patient discomfort and risk of injury.

Apart from the above, sensor accuracy and sensitivity can be further improved by optimizing the knot geometries to minimize directional heterogeneity, pursuing further miniaturization of the elastic tubing, and incorporating a robotic, knitting-based manufacturing process to allow circumferential packing of multiple knots into an integrated device.

An important consideration in potentially translating the SPS to a specific clinical use is the choice of the most appropriate sensing mode for each clinical indication. For example, spatial information is important for evaluating esophageal motility disorders, but may not be as crucial in the assessment of anal sphincter tone or squeeze pressure. The choice of the appropriate testing medium is also important for esophageal motility evaluations.

This represents a potentially cheap, convenient, and simple option for the evaluation of GI motility. From a practical standpoint, the availability of an ultra-low-cost manometry device for one-time use would allow expansion of this technology to regions with limited resources. Even in resource-rich regions or institutions, such disposable devices can further avoid the minimal risk of cross-contamination and increase the throughput of scheduled cases, as there would not be a need for built-in time in between cases for device decontamination. Other advantages of disposable catheters include avoiding the recurring maintenance and repair costs of the current expensive catheters, and minimizing the potential delay in clinical care when the multi-use catheters are out for repair.

Methods of Manufacture

Fabrication of the SPS is illustrated in FIG. 12. Fabrication started by trimming silicone tubing into the desired length, followed by injecting eGaIn (e.g., a conductive fluid) using a needle syringe. Electrical leads (e.g., copper wires) were inserted into both ends of the tubing to establish electrical connections, followed by sealing both ends using fast-drying silicone sealant (e.g., a quick-casting silicone sealant, sil-poxy rubber silicone adhesive from smooth-on, or any other commercially available adhesives that have good adhesion to silicone and low curing time). Subsequently, knots can be tied at designated positions directly by hand, or first by hand loosely, then by a mechanical stretcher (e.g., a Mark-10, model ES20 mechanical stretcher) using designated tensile force (e.g. approximately 0.1 newtons) and holding for approximately thirty seconds (see FIG. 24). For applications that require resistance to tensile stretching, a drop of UV curing adhesive (e.g., approximately 0.2 milliliters) can be applied onto the knots followed by curing using a hand-held UV lamp for a designated curing time (e.g., approximately 120 seconds, or more or less).

To fabricate the multichannel SPS for in vivo rectoanal evaluations, each channel was fabricated individually using the above procedures, then aligned and positioned. UV curing adhesive was applied at multiple locations along the device to secure individual tubing into one.

To fabricate the ribbon-like manometry device (SPS) for esophageal motility evaluations, slightly different procedures were used and illustrated in FIG. 47. Briefly, a meter-long silicone tubing was first filled with eGaIn, followed by cutting the tube into approximately 6 centimeter long segments. A knot was tied onto each segment using a mechanical stretcher, connected with copper wires at both ends and sealed using UV curing optical adhesive. The step was repeated eight times and the resulting segments were placed and adhered onto an approximately 45 centimeter long medical-grade silicone gel tape with approximately 5 centimeters spacing between adjacent knots. An approximately 13 micrometer thick, low-density polyethylene film was used to encapsulate the top surface, which completed the fabrication process.

Characterizing Pressure Sensitivity

A manual mechanical testing stage coupled with a force gauge was used to apply precisely controlled compressive force onto the SPS, which was then converted to pressure by dividing the applied force by the contact area perpendicular to the direction of the applied force. The channels were connected to a resistance measuring device (e.g., a source meter) for two-point resistance measurement, with a source direct current (DC) voltage set to 0.5 volts (see FIG. 11).

Numerical Simulations

All the simulations were carried out using a commercial Finite Element (FE) package, Abaqus 2017 (SIMULIA, Providence, RI). The Abaqus solver was employed for the simulations. Three-dimensional (3D) FE models of the elastomeric tubing were constructed using 8-node linear brick with reduced integration and hourglass control (e.g., Abaqus element type C3D8R). The material behavior of the elastomers was captured using a nearly-incompressible Neo-Hookean hyperelastic model (e.g., with a Poisson's ratio of v_0 or approximately 0.499 and a density of approximately 1000 kilograms per cubic meter) with directly imported uniaxial tension test data. The Dynamic Explicit solver (e.g., from the DYNAMIC module in Abaqus 2017) with a mass scaling factor of ten thousand (to facilitate convergence) was used. Optionally, a small damping factor can be used and, in some cases, can assist with maintaining quasi-static conditions. A simplified contact law (General Contact type interaction) was assigned to the models with a penalty friction coefficient of 0.3 for tangential behavior and hard contact for normal behavior. Two sets of analyses were performed:

Elastic Overhand Knot Formation

First, we created FE models of the bent tube similar to the loop configuration shown in FIG. 29. We kinematically tied the extremities of the tube to a pair of reference nodes positioned at the center of each of the extremities of the tube. To establish a knot configuration, we pulled the extremities of the tube via application of displacement, Δx/2, to the reference points along the ±x direction. The identical reaction forces at the reference points were recorded as a function of Δx. The sequence of progressively deformed shape of the elastic tube to form a knot were shown in FIG. 29.

Normal Compression of Elastic Knots

Following the elastic knot formation simulations, the response of the knots under normal compression was evaluated by subsequent compression of knots at different levels of Δx across a range of elastic moduli and wall thicknesses using a rigid plate. The plate was meshed using 4-node 3D bilinear rigid quadrilateral (Abaqus element type R3D4) and was initially positioned slightly above the knots, which were calculated from previous uniaxial tensile simulations. We performed dynamic explicit analysis by lowering the plate in the z direction until it compressed the knots down to a normalized height, Δz/H_0, of 0.6, where H_0 is the initial height of the given knot (FIG. 2F). The reaction force of the plate was recorded as a function of applied displacement in the normal direction, Δz (Movie S2).

The resultant SPS from the above strategy is simple and cheap to fabricate compared to existing GI manometry. The fabrication process may require only basic bench tools such as syringes, scissors, and fast-drying silicone sealants (FIG. 10), which can be completed by a moderately trained person in a short period of time (e.g., under an hour). In addition, a rudimentary digital multimeter suffices as the minimal requirement for data recording and display, as opposed to the bulky perfusion pumps or the catheter-specific dataloggers required by conventional GI manometry systems. The simple and robust fabrication procedures also allowed for quick customization of the sensor configurations and distributions without additional cost, and interfacing with various other tools and substrates to accommodate different portions of the GI tract with distinct anatomy and motility profiles, as were demonstrated in the in vivo implementations below. These and other features make SPS promising for deployment in less developed regions and non-hospital settings where state-of-the-art manufacturing equipment and external hardware may be limited.

As used in the claims, the phrase "at least one of A, B, and C" means at least one of A, at least one of B, and/or at least one of C, or any one of A, B, or C or combination of A, B, or C. A, B, and C are elements of a list, and A, B, and C may be anything contained in the Specification.

The present invention has been described in terms of one or more preferred embodiments, and it should be appreciated that many equivalents, alternatives, variations, and modifications, aside from those expressly stated, are possible and within the scope of the invention.

The invention claimed is:

1. A system for assessing a pressure profile of a gastrointestinal (GI) tract, the system comprising:
- a flexible tube defining a first lumen;
- an electrically-conductive liquid contained within the first lumen;
- at least one restriction formed on the flexible tube to constrict but not completely occlude the first lumen wherein the at least one restriction includes a knot; and
- a sensor system configured to monitor an electrical property of the electrically-conductive liquid within the flexible tube over time and generate a report of pressure changes in the GI tract by correlating changes in the electrical property with the pressure changes in the GI tract.

2. The system of claim 1, further comprising a sleeve formed over the at least one restriction.

3. The system of claim 2, wherein the sleeve is formed by an adhesive applied about the at least one restriction.

4. The system of claim 1, further comprising a plurality of restrictions arranged along the flexible tube to spatially resolve compression by the GI tract.

5. The system of claim 1, further comprising a plurality of flexible tubes with respective restrictions formed therein and configured to be spatially displaced from each other when in the GI tract.

6. The system of claim 5, wherein the sensor system is configured to monitor the electrical property of the electrically-conductive liquid in the plurality of flexible tubes and spatially resolve compression by the GI tract.

7. The system of claim 1, wherein the electrically-conductive liquid includes eutectic gallium-indium.

8. The system of claim 1, further comprising a first conductor extending into the first lumen at a first end and a second conductor extending into the first lumen at a second end located opposite the first end, and where the sensor system is configured to measure an electrical resistance between the first conductor and the second conductor.

9. The system of claim 1, wherein the at least one restriction is configured to create an approximately linear correlation between the electrical property and the pressure.

10. A manometry system for obtaining a pressure profile of a gastrointestinal (GI) tract, the manometry system comprising:

a catheter configured to be placed endoluminally into the GI tract, the catheter including a plurality of sealed flexible tubes, each of the plurality of sealed flexible tubes defining a lumen that is filled with an electrically-conductive fluid and defining at least one restriction to constrict but not completely occlude the lumen to be compressed by the GI tract to induce a change in an electrical resistance of the electrically-conductive fluid within a respective one of the plurality of sealed flexible tubes, wherein the at least one restriction of each of the plurality of sealed flexible tubes includes a knot;

a sensor configured to acquire electrical measurements of each of the plurality of sealed flexible tubes; and a processor configured to determine a pressure profile of the GI tract by correlating the electrical measurements of each of the plurality of sealed flexible tubes with a pressure in the GI tract.

11. The manometry system of claim 10, wherein the at least one restriction of each of the plurality of sealed flexible tubes are spatially displaced from each other when in the GI tract and at least one of the sensor or the processor multiplexes the electrical measurements to spatially resolve compression by the GI tract.

12. The manometry system of claim 10, wherein a sleeve is formed over the at least one restriction of each of the plurality of sealed flexible tubes, the sleeve being configured to control movement of the at least one restriction.

13. The manometry system of claim 10, wherein the catheter further includes an outer sleeve configured to surround the plurality of sealed flexible tubes.

14. The manometry system of claim 10, wherein each of the plurality of sealed flexible tubes includes a first conductor extending into the lumen at a first end and a second conductor extending into the lumen at a second end, and wherein the sensor is coupled to each of the first conductor and the second conductor.

15. The manometry system of claim 10, wherein each of the plurality of sealed flexible tubes are is formed of an elastic material and the electrically-conductive fluid includes eutectic gallium-indium.

16. A method of manufacturing a system for obtaining a pressure profile of a gastrointestinal (GI) tract, the method including steps comprising:

inserting a first conductor into a first end of a flexible tube defining a first lumen so that the first conductor extends between the first lumen and an exterior of the flexible tube;

sealing the first end of the flexible tube;

filling the flexible tube with a conductive fluid;

inserting a second conductor into a second end of the flexible tube to extend the second conductor between the first lumen and the exterior of the flexible tube;

sealing the second end of the flexible tube; and forming at least one restriction on the flexible tube, wherein the step of forming the at least one restriction on the flexible tube includes tying a knot with the flexible tube, the at least one restriction is configured to constrict but not completely occlude the first lumen and to be compressed by the GI tract to induce a change in an electrical resistance of the conductive fluid within the flexible tube that is correlated with a pressure at the at least one restriction.

17. The method of claim 16, further comprising enclosing the at least one restriction in a sleeve.

18. The method of claim 17, wherein the step of enclosing the at least one restriction in a sleeve includes applying an adhesive to the at least one restriction.

19. A flexible pressure sensor comprising:

a sealed flexible tube defining a lumen extending between a first end of the sealed flexible tube and a second end of the sealed flexible tube;

a conductive liquid contained within the lumen;

a first conductor extending into the lumen at the first end;

a second conductor extending into the lumen at the second end; and a restriction formed on the sealed flexible tube between the first end and the second end to constrict but not completely occlude the lumen, wherein the restriction includes a knot, the restriction being configured to be compressed to induce a change in an electrical resistance of the conductive liquid within the sealed flexible tube that is correlated with a pressure at the restriction.

* * * * *